(12) United States Patent
Balakrishnan et al.

(10) Patent No.: US 11,932,691 B2
(45) Date of Patent: Mar. 19, 2024

(54) ANTI-ROR1 ANTIBODIES AND USES THEREOF

(71) Applicant: Fred Hutchinson Cancer Center, Seattle, WA (US)

(72) Inventors: Ashwini Balakrishnan, Seattle, WA (US); Benjamin G. Hoffstrom, Seattle, WA (US); Julie Randolph-Habecker, Yakima, WA (US); Stanley R. Riddell, Sammamish, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 334 days.

(21) Appl. No.: 17/157,810

(22) Filed: Jan. 25, 2021

(65) Prior Publication Data

US 2021/0147540 A1    May 20, 2021

Related U.S. Application Data

(62) Division of application No. 16/074,737, filed as application No. PCT/US2017/016300 on Feb. 2, 2017, now Pat. No. 10,968,275.

(60) Provisional application No. 62/324,876, filed on Apr. 19, 2016, provisional application No. 62/290,337, filed on Feb. 2, 2016.

(51) Int. Cl.
  *C07K 16/28* (2006.01)
  *G01N 33/574* (2006.01)

(52) U.S. Cl.
  CPC ... *C07K 16/2803* (2013.01); *G01N 33/57492* (2013.01); *C07K 2317/24* (2013.01); *C07K 2317/33* (2013.01); *C07K 2317/34* (2013.01); *C07K 2317/622* (2013.01); *C07K 2317/92* (2013.01); *G01N 2333/70503* (2013.01)

(58) Field of Classification Search
  None
  See application file for complete search history.

(56) References Cited

U.S. PATENT DOCUMENTS

| | | | |
|---|---|---|---|
| 5,283,173 | A | 2/1994 | Fields et al. |
| 5,468,614 | A | 11/1995 | Fields et al. |
| 9,163,258 | B2 | 10/2015 | Riddell et al. |
| 10,968,275 | B2 | 4/2021 | Balakrishnan et al. |
| 2011/0129478 | A1 | 6/2011 | Okano et al. |
| 2012/0058051 | A1 | 3/2012 | Rader et al. |
| 2013/0202622 | A1 | 8/2013 | Riddell et al. |
| 2013/0251642 | A1 | 9/2013 | Rader et al. |
| 2015/0306141 | A1 | 10/2015 | Jensen et al. |
| 2016/0208018 | A1 | 7/2016 | Chen et al. |
| 2018/0200298 | A1 | 7/2018 | Jensen et al. |
| 2018/0265593 | A1 | 9/2018 | Chen et al. |
| 2020/0078405 | A1 | 3/2020 | Jensen et al. |

FOREIGN PATENT DOCUMENTS

| | | |
|---|---|---|
| WO | 02/02641 A1 | 1/2002 |
| WO | 03/085093 A2 | 10/2003 |
| WO | 2005/035732 A2 | 4/2005 |
| WO | 2005/037235 A2 | 4/2005 |
| WO | 2005/097184 A2 | 10/2005 |
| WO | 2010/005068 A1 | 1/2010 |
| WO | 2010/075238 A1 | 7/2010 |
| WO | 2010/124188 A1 | 10/2010 |
| WO | 2011/014469 A1 | 2/2011 |
| WO | 2011/159847 A2 | 12/2011 |
| WO | 2012/045085 A1 | 4/2012 |
| WO | 2012/076066 A1 | 6/2012 |
| WO | 2012/129514 A1 | 9/2012 |
| WO | 2013/022968 A1 | 2/2013 |
| WO | 2013/043933 A2 | 3/2013 |
| WO | 2014/031174 A1 | 2/2014 |
| WO | 2014/031687 A1 | 2/2014 |
| WO | 2014/164554 A1 | 10/2014 |
| WO | 2016/016344 A1 | 2/2016 |
| WO | 2016/069647 A1 | 5/2016 |
| WO | 2016/115559 A1 | 7/2016 |
| WO | 2016/187216 A1 | 11/2016 |
| WO | 2017/214207 A2 | 12/2017 |

OTHER PUBLICATIONS

Balakrishnan et al., Analysis of ROR1 Protein Expression in Human Cancer and Normal Tissues. Clin. Cancer Res. 23(12): 3061-71, Jun. 15, 2017.*
Alder et al., "Antibody responses of variable lymphocyte receptors in the lamprey," *Nature Immunology* 9(3):319-327, 2008.
Al-Lazikani et al., "Standard Conformations for the Canonical Structures of Immunoglobulins," *J. Mol. Biol.* 273:927-948, 1997.
Antibodies-online GmbH, "Anti-ROR1 antibody (Receptor Tyrosine Kinase-Like Orphan Receptor 1) (C-Term)," Datasheet for ABIN5539753, Sep. 1, 2008, Accessed Jan. 20, 2021, URL=https://www.antibodiesonline.com/productsheets/ABIN5539753.pdf (4 pages).
Antibodies-online, "ROR1 antibody (Receptor Tyrosine Kinase-Like Orphan Receptor 1) (C-Term)," Technical Data Sheet, Apr. 19, 2017, 4 pages.
Aviva Systems Biology, "ROR1 Antibody—C-terminal region (ARP63925_P050)," Product Data Sheet, Jan. 1, 2016, URL=http://www.avivasysbio.com/sd/tds/html_datasheet.php?sku=ARP63925_P050, download date Apr. 19, 2017, 2 pages.
Baral et al., "Experimental therapy of African trypanosomiasis with a nanobody-conjugated human trypanolytic factor," *Nature Medicine* 12(5):580-584, 2006.

(Continued)

*Primary Examiner* — Ruixiang Li
(74) *Attorney, Agent, or Firm* — Seed IP Law Group LLP

(57) ABSTRACT

The present disclosure relates to anti-ROR1 binding proteins, including those that bind to a ROR1 or portion thereof such as an intracellular C terminal portion of a ROR1 protein, and the use of such binding proteins in immunohistochemical and diagnostic methods. Related kits and methods of using the binding proteins are also provided, as are methods of treatment of subjects having diseases or conditions determined to be candidates for such treatments by the binding proteins or methods of this disclosure.

33 Claims, 47 Drawing Sheets
Specification includes a Sequence Listing.

(56) References Cited

OTHER PUBLICATIONS

Barthelemy et al., "Comprehensive Analysis of the Factors Contributing to the Stability and Solubility of Autonomous Human $V_H$ Domains," *The Journal of Biological Chemistry* 283(6):3639-3654, 2008 (17 pages).
Baskar et al., "Targeting malignant B cells with an immunotoxin against ROR1," *mAbs* 4(3):349-361, 2012.
Baskar et al., "Unique Cell Surface Expression of Receptor Tyrosine Kinase ROR1 in Human B-Cell Chronic Lymphocytic Leukemia," *Clinical Cancer Research* 14(2):396-404, 2008.
Berger et al., "Safety of Targeting ROR1 in Primates with Chimeric Antigen Receptor-Modified T Cells," *Cancer Immunol Res* 3(2):206-216, 2015 (12 pages).
Bridgeman et al., "Building Better Chimeric Antigen Receptors for Adoptive T Cell Therapy," *Current Gene Therapy* 10:77-90, 2010.
Brummell et al., "Probing the Combining Site of an Anti-Carbohydrate Antibody by Saturation-Mutagenesis: Role of the Heavy-Chain CDR3 Residues," *Biochemistry* 32:1180-1187, 1993.
Burks et al., "In vitro scanning saturation mutagenesis of an antibody binding pocket," *Proc. Natl. Acad. Sci. USA* 94:412-417, 1997.
Capon et al., "Designing CD4 immunoadhesins for AIDS therapy," *Nature* 337:525-531, 1989.
Cartellieri et al. "Chimeric Antigen Receptor-Engineered T Cells for Immunotherapy of Cancer," *Journal of Biomedicine and Biotechnology 2010*, Article ID 956304, 2010 (13 pages).
Casset et al., "A peptide mimetic of an anti-CD4 monoclonal antibody by rational design," *Biochemical and Biophysical Research Communications* 307:198-205, 2003.
Chen et al., "Cirmtuzumab blocks Wnt5a/ROR1 stimulation of NF-κB to repress autocrine STAT3 activation in chronic lymphocytic leukemia," *Blood* 134(13):1084-1094, 2019.
Chen et al., "Selection and Analysis of an Optimized Anti-VEGF Antibody: Crystal Structure of an Affinity-matured Fab in Complex with Antigen," *J. Mol. Biol.* 293:865-881, 1999.
Chien et al., "Expression of ROR1 has prognostic significance in triple negative breast cancer," *Virchows Arch.* 468(5):589-595, 2016.
Choi et al., "Phase I Trial: Cirmtuzumab Inhibits ROR1 Signaling and Stemness Signatures in Patients with Chronic Lymphocytic Leukemia," Cell Stem Cell 22(6):951-959, 2018 (13 pages).
Choi et al., "Pre-clinical Specificity and Safety of UC-961, a First-In-Class Monoclonal Antibody Targeting ROR1," *Clinical Lymphoma, Myeloma & Leukemia* 15(Suppl. 1):S167-S169, 2015.
ClinicalTrials.gov, "Autologous ROR1R-CAR-T Cells for Chronic Lymphocytic Leukemia (CLL)," *U.S. National Library of Medicine*, first posted Jul. 18, 2014, retrieved May 1, 2020, 8 pages.
ClinicalTrials.gov, "Genetically Modified T-Cell Therapy in Treating Patients With Advanced ROR1+ Malignancies," *U.S. National Library of Medicine*, first posted Mar. 11, 2016, retrieved May 1, 2020, 12 pages.
Colman, "Effects of amino acid sequence changes on antibody-antigen interactions," *Res Immunol.* 145:33-36, 1994.
Cortez-Retamozo et al., "Efficient Cancer Therapy with a Nanobody-Based Conjugate," *Cancer Research* 64:2853-2857, 2004.
Cui et al., "Targeting ROR1 Inhibits Epithelial-Mesenchymal Transition and Metastasis," *Cancer Research* 73(12):3649-3660, 2013.
Daneshmanesh et al., "Monoclonal antibodies against ROR1 induce apoptosis of chronic lymphocytic leukemia (CLL) cells," *Leukemia* 26:1348-1355, 2012.
Daneshmanesh et al., "Ror1, a cell surface receptor tyrosine kinase is expressed in chronic lymphocytic leukemia and may serve as a putative target for therapy," *Int. J. Cancer* 123:1190-1195, 2008.
Dave et al., "Restricted Cell Surface Expression of Receptor Tyrosine Kinase ROR1 in Pediatric B-Lineage Acute Lymphoblastic Leukemia Suggests Targetability with Therapeutic Monoclonal Antibodies," *PLoS ONE* 7(12):e52655, 2012. (12 pages).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," *The Journal of Immunology* 169:3076-3084, 2002.
Fukuda et al., "Antisera induced by infusions of autologous Ad-CD154-leukemia B cells identify ROR1 as an oncofetal antigen and receptor for Wnt5a," *PNAS* 105(8):3047-3052, 2008.
Ghahroudi et al., "Selection and identification of single domain antibody fragments from camel heavy-chain antibodies," *FEBS Letters* 414:521-526, 1997.
Hamers-Casterman et al., "Naturally occurring antibodies devoid of light chains," *Nature* 363:446-448, 1993.
Hassan et al., "Phase I Study of SS1P, a Recombinant Anti-Mesothelin Immunotoxin Given as a Bolus I.V. Infusion to Patients with Mesothelin-Expressing Mesothelioma, Ovarian, and Pancreatic Cancers," *Clin Cancer Res* 13(17):5144-5149, 2007 (7 pages).
Herrin et al., "Structure and specificity of lamprey monoclonal antibodies," *PNAS* 105(6):2040-2045, 2008.
Hojjat-Farsangi et al., "Inhibition of the Receptor Tyrosine Kinase ROR1 by Anti-ROR1 Monoclonal Antibodies and siRNA Induced Apoptosis of Melanoma Cells," *PLOS ONE* 8(4):e61167, 2013 (10 pages).
Holm et al., "Functional mapping and single chain construction of the anti-cytokeratin 8 monoclonal antibody TS1," *Molecular Immunology* 44:1075-1084, 2007.
Honegger et al., "Yet Another Numbering Scheme for Immunoglobulin Variable Domains: An Automatic Modeling and Analysis Tool," *J. Mol. Biol.* 309:657-670, 2001.
Hudecek et al., "Naïve CD4+ T Cells Modified to Express a ROR1-Specific CAR Mediate Anti-Tumor Activity and Provide Superior Help to CD8+ ROR1-CAR T Cells," *Blood* 118(21):643, 2011 (6 pages) (Abstract only).
Hudecek et al., "The Anti-Tumor Reactivity of ROR1-CAR Modified T Cells Depends on the Targeted Epitope, CAR-Affinity and Design of the CAR Extracellular Domain," *Clinical Lymphoma, Myeloma & Leukemia Supplement* 11(Supplement 2):S280-S281, 2011 (2 pages) (Abstract only).
Hudecek et al., "Receptor affinity and extracellular domain modifications affect tumor recognition by ROR1-specific chimeric antigen receptor T-cells," *Clin. Cancer Res.* 19(12):3153-3164, 2013. (13 pages).
Hudecek et al., "The B-cell tumor-associated antigen ROR1 can be targeted with T cells modified to express a ROR1-specific chimeric antigen receptor," *Blood* 116(22):4532-4541, 2010. (18 pages).
Jespers et al., "Aggregation-resistant domain antibodies selected on phage by heat denaturation," *Nature Biotechnology* 22(9):1161-1165, 2004.
Karachaliou et al., "ROR1 as a novel therapeutic target for EGFR-mutant non-small-cell lung cancer patients with the EGFR T790M mutation," *Translational Lung Cancer Research* 3(3):122-130, 2014.
Kaucká et al., "Post-translational modifications regulate signalling by Ror1," *Acta Physiol* 203:351-362, 2011.
Kim et al., "High Cleavage Efficiency of a 2A Peptide Derived from Porcine Teschovirus-1 in Human Cell Lines, Zebrafish and Mice," *PLoS ONE* 6(4):e18556, 2011 (8 pages).
Kobayashi et al., "Tryptophan H33 plays an important role in pyrimidine (6-4) pyrimidone photoproduct binding by a high-affinity antibody," *Protein Engineering* 12(10):879-884, 1999.
Kumar et al., "Molecular Cloning and Expression of the Fabs of Human Autoantibodies in *Escherichia coli*," *The Journal of Biological Chemistry* 275(45):35129-35136, 2000.
Lamers et al., "Treatment of Metastatic Renal Cell Carcinoma With CAIX CAR-engineered T cells: Clinical Evaluation and Management of On-target Toxicity," *Molecular Therapy* 21(4):904-912, 2013.
Lefranc et al., "IMGT unique numbering for immunoglobulin and T cell receptor variable domains and Ig superfamily V-like domains," *Developmental and Comparative Immunology* 27:55-77, 2003.
Leisegang et al., "Enhanced functionality of T cell receptor-redirected T cells is defined by the transgene cassette," *J Mol Med* 86:573-583, 2008.

(56) References Cited

OTHER PUBLICATIONS

Liu et al., "Silencing of Receptor Tyrosine Kinase ROR1 Inhibits Tumor-Cell Proliferation via PI3K/AKT/mTOR Signaling Pathway in Lung Adenocarcinoma," *PLoS ONE* 10(5):e0127092, 2015. (14 pages).
MacCallum et al., "Antibody-antigen Interactions: Contact Analysis and Binding Site Topography," *J. Mol. Biol.* 262:732-745, 1996.
Morgan et al., "Case Report of a Serious Adverse Event Following the Administration of T Cells Transduced With a Chimeric Antigen Receptor Recognizing ERBB2," *Molecular Therapy* 18(4):843-851, 2010.
Nguyen et al., "Heavy-chain antibodies in Camelidae; a case of evolutionary innovation" *Immunogenetics* 54:39-47, 2002.
Nguyen et al., "The Specific Variable Domain of Camel Heavy-chain Antibodies is Encoded in the Germline," J. Mol. Biol. 275:413-418, 1998.
Roux et al., "Structural analysis of the nurse shark (new) antigen receptor (NAR): Molecular convergence of NAR and unusual mammalian immunoglobulins," Proc. Natl. Acad. Sci. USA 95:11804-11809, 1998.
Scatchard, "The Attractions of Proteins for Small Molecules and Ions," *Annals of the New York Academy of Sciences* 51(4):660-672, 1949 (17 pages).
Scholten et al., "Codon modification of T cell receptors allows enhanced functional expression in transgenic human T cells," *Clinical Immunology* 119:135-145, 2006.
Smith-Gill et al., "Contributions of Immunoglobulin Heavy and Light Chains to Antibody Specificity for Lysozyme and Two Haptens," *The Journal of Immunology* 139(12):4135-4144, 1997.
Song et al., "Light Chain of Natural Antibody Plays a Dominant Role in Protein Antigen Binding," *Biochemical and Biophysical Research Communications* 258:390-394, 2000.
Specht et al., "Phase I study of immunotherapy for advanced ROR1+ malignancies with autologous ROR1-specific chimeric antigen receptor-modified (CAR)-T cells," *Journal of Clinical Oncology* 36(5 Suppl):TPS79, 2018 (4 pages).
UniProtKB No. Q9Z139-1, Apr. 27, 2001 (14 pages).
UniProtKB, "Inactive tyrosine-protein kinase transmembrane receptor ROR1," Accession No. Q01973-1, created Apr. 27, 2001, last modified Apr. 22, 2020, 12 pages.
UniProtKB, "Inactive tyrosine-protein kinase transmembrane receptor ROR1," Accession No. Q01973-2, Isoform 2, created Apr. 27, 2001, last modified Jun. 17, 2020, 11 pages.
UniProtKB, "Inactive tyrosine-protein kinase transmembrane receptor ROR1," Accession No. Q01973-3, Isoform 3, created Apr. 27, 2001, last modified Jun. 17, 2020, 11 pages.
Unpublished U.S. Appl. No. 17/015,955, filed Sep. 9, 2020.
Vajdos et al., "Comprehensive Functional Maps of the Antigen-binding Site of an Anti-ErbB2 Antibody Obtained with Shotgun Scanning Mutagenesis," *J. Mol. Biol.* 320:415-428, 2002.
Vincke et al., "General Strategy to Humanize a Camelid Single-domain Antibody and Identification of a Universal Humanized Nanobody Scaffold," *The Journal of Biological Chemistry* 284(5):3273-3284, 2009 (13 pages).
Ward et al., "Binding activities of a repertoire of single immunoglobulin variable domains secreted from *Escherichia coli,*" *Nature* 341:544-546, 1989.
Wilson, "Analyzing Biomolecular Interactions," *Science* 295(5562):2103-2105, 2002 (3 pages).
Wolff et al., "Monoclonal Antibody Homodimers: Enhanced Antitumor Activity in Nude Mice," *Cancer Research* 53:2560-2565, 1993 (7 pages).
Wu et al., "Humanization of a Murine Monoclonal Antibody by Simultaneous Optimization of Framework and CDR Residues," *J. Mol. Biol.* 294:151-162, 1999.
Yamaguchi et al., "NKX2-1/TITF1/TTF-1-Induced ROR1 Is Required to Sustain EGFR Survival Signaling in Lung Adenocarcinoma," *Cancer Cell* 21(3):348-361, 2012.
Yang et al., "Therapeutic Potential and Challenges of Targeting Receptor Tyrosine Kinase ROR1 with Monoclonal Antibodies in B-Cell Malignancies," *PLoS ONE* 6(6):e21018, 2011. (15 pages).
Yu et al., "Cirmtuzumab inhibits Wnt5a-induced Rac1 activation in chronic lymphocytic leukemia treated with ibrutinib," *Leukemia* 31(6):1333-1339, 2017.
Zaritskaya et al., "New flow cytometric assays for monitoring cell-mediated cytotoxicity," *Expert Rev Vaccines* 9(6):601-616, 2010 (NIH Public Access Author Manuscript, available in PMC Apr. 1, 2011) (26 pages).
Zhang et al., "ROR1 expression correlated with poor clinical outcome in human ovarian cancer," *Scientific Reports* 4:5811, 2014. (7 pages).
Zhang et al., "ROR1 Is Expressed in Human Breast Cancer and Associated with Enhanced Tumor-Cell Growth," *PloS ONE* 7(3):e31127, 2012. (12 pages).
Zhang et al., "The Onco-Embryonic Antigen ROR1 Is Expressed by a Variety of Human Cancers," *The American Journal of Pathology* 181(6):1903-1910, 2012.

* cited by examiner

FIG. 5

```
Human   NPRYPNYMFPSQGITPQGQIAGFIGPPPIP   SEQ ID NO:3
Mouse   .....F..........................A....   SEQ ID NO:57
Rhesus  ...........I............................   SEQ ID NO:59
```

*FIG. 23A*

SEQUENCE LISTING

```
<160> NUMBER OF SEQ ID NOS: 59

<210> SEQ ID NO 1
<211> LENGTH: 937
<212> TYPE: PRT
<213> ORGANISM: Homo sapiens

<400> SEQUENCE: 1

Met His Arg Pro Arg Arg Arg Gly Thr Arg Pro Pro Leu Leu Ala Leu
1               5                   10                  15

Leu Ala Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140
```

-continued

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
            165                 170                 175

Ala Cys Arg Phe Ile Gly Asn Arg Thr Val Tyr Met Glu Ser Leu
        180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
            245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
            325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
            405                 410                 415

Ala Ile Ala Leu Leu Phe Phe Phe Ile Cys Val Cys Arg Asn Asn Gln
        420                 425                 430

Lys Ser Ser Ser Ala Pro Val Gln Arg Gln Pro Lys His Val Arg Gly
        435                 440                 445

Gln Asn Val Glu Met Ser Met Leu Asn Ala Tyr Lys Pro Lys Ser Lys
    450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
            485                 490                 495

Met Asp His Ala Gln Leu Val Ala Ile Lys Thr Leu Lys Asp Tyr Asn
        500                 505                 510

Asn Pro Gln Gln Trp Thr Glu Phe Gln Gln Glu Ala Ser Leu Met Ala
        515                 520                 525

Glu Leu His His Pro Asn Ile Val Cys Leu Leu Gly Ala Val Thr Gln
        530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser 565                 570                 575
Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
            595                 600                 605

His Phe Val His Lys Asp Leu Ala Arg Asn Ile Leu Ile Gly
            610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
            645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
            675                 680                 685

Gly Leu Gln Pro Tyr Tyr Gly Phe Ser Asn Gln Glu Val Ile Glu Met
            690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
            725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
            755                 760                 765

Gln Thr Thr Ser Leu Ser Ala Ser Pro Val Ser Asn Leu Ser Asn Pro
            770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
            805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
            835                 840                 845

Pro Pro Pro Lys Ser Arg Ser Pro Ser Ser Ala Ser Gly Ser Thr Ser
            850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
            885                 890                 895

Met Gly Ile Thr Val Phe Gly Asn Lys Ser Gln Lys Pro Tyr Lys Ile
            900                 905                 910

Asp Ser Lys Gln Ala Ser Leu Leu Gly Asp Ala Asn Ile His Gly His
            915                 920                 925

Thr Glu Ser Met Ile Ser Ala Glu Leu
            930                 935

<210> SEQ ID NO 2
<211> LENGTH: 19
<212> TYPE: PRT
<213> ORGANISM: Artificial Sequence
<220> FEATURE:
<223> OTHER INFORMATION: fragment of human ROR1

-continued

```
<400> SEQUENCE: 2

Asn Gln Lys Ser Ser Ser Ala Pro Val Gln Arg Gln Pro Lys His Val
1               5                   10                  15

Arg Gly Gln

<210> SEQ ID NO 3
<211> LENGTH: 29
<212> TYPE: PRT
<213> ORGANISM: Artificial Sequence
<220> FEATURE:
<223> OTHER INFORMATION: fragment of human ROR1

<400> SEQUENCE: 3

Asn Pro Arg Tyr Pro Asn Tyr Met Phe Pro Ser Gln Gly Ile Thr Pro
1               5                   10                  15

Gln Gly Gln Ile Ala Gly Phe Ile Gly Pro Pro Ile Pro
            20                  25

<210> SEQ ID NO 4
<211> LENGTH: 19
<212> TYPE: PRT
<213> ORGANISM: Artificial Sequence
<220> FEATURE:
<223> OTHER INFORMATION: fragment of human ROR1

<400> SEQUENCE: 4

Gln Glu Ala Asn Ile Pro Leu Leu Pro His Met Ser Ile Pro Asn His
1               5                   10                  15

Pro Gly Gly

<210> SEQ ID NO 5
<211> LENGTH: 18
<212> TYPE: PRT
<213> ORGANISM: Artificial Sequence
<220> FEATURE:
<223> OTHER INFORMATION: fragment of human ROR1

<400> SEQUENCE: 5

Lys Ile Asp Ser Lys Gln Ala Ser Leu Leu Gly Asp Ala Asn Ile His
1               5                   10                  15

Gly His

<210> SEQ ID NO 6
<211> LENGTH: 8
<212> TYPE: PRT
<213> ORGANISM: Artificial Sequence
<220> FEATURE:
<223> OTHER INFORMATION: fragment of human 6D4 antibody

<400> SEQUENCE: 6

Gly Tyr Thr Phe Thr Asp Tyr Tyr
1               5

<210> SEQ ID NO 7
<211> LENGTH: 8
<212> TYPE: PRT
<213> ORGANISM: Artificial Sequence
<220> FEATURE:
<223> OTHER INFORMATION: fragment of human 6D4 antibody

<400> SEQUENCE: 7

Val Asn Pro Ser Asn Gly Asn Thr
1               5
```

<210> SEQ ID NO 8
<211> LENGTH: 7
<212> TYPE: PRT
<213> ORGANISM: Artificial Sequence
<220> FEATURE:
<223> OTHER INFORMATION: fragment of human 6D4 antibody

<400> SEQUENCE: 8

Cys Gly Arg Leu Ala Tyr Trp
1               5

<210> SEQ ID NO 9
<211> LENGTH: 10
<212> TYPE: PRT
<213> ORGANISM: Artificial Sequence
<220> FEATURE:
<223> OTHER INFORMATION: fragment of human 6D4 antibody

<400> SEQUENCE: 9

Gln Ser Val Asp Tyr Asp Gly Glu Thr Tyr
1               5                   10

<210> SEQ ID NO 10
<211> LENGTH: 3
<212> TYPE: PRT
<213> ORGANISM: Artificial Sequence
<220> FEATURE:
<223> OTHER INFORMATION: fragment of human 6D4 antibody

<400> SEQUENCE: 10

Ala Ala Ser
1

<210> SEQ ID NO 11
<211> LENGTH: 11
<212> TYPE: PRT
<213> ORGANISM: Artificial Sequence
<220> FEATURE:
<223> OTHER INFORMATION: fragment of human 6D4 antibody

<400> SEQUENCE: 11

Cys Leu Gln Thr Leu Lys Asn Pro Tyr Thr Phe
1               5                   10

<210> SEQ ID NO 12
<211> LENGTH: 112
<212> TYPE: PRT
<213> ORGANISM: Artificial Sequence
<220> FEATURE:
<223> OTHER INFORMATION: fragment of antibody

<400> SEQUENCE: 12

Glu Val Lys Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Thr His Gly Lys Asn Leu Glu Trp Ile
        35                  40                  45

Gly Arg Val Asn Pro Ser Asn Gly Asn Thr Asp Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Ser Ser Leu Thr Ser Glu Asp Ser Ala Val Tyr Tyr Cys
                85                  90                  95

```
Gly Arg Leu Ala Tyr Trp Gly Gln Gly Ser Leu Val Thr Val Ser Ala
            100                 105                 110
```

<210> SEQ ID NO 13
<211> LENGTH: 112
<212> TYPE: PRT
<213> ORGANISM: Artificial Sequence
<220> FEATURE:
<223> OTHER INFORMATION: fragment of antibody

<400> SEQUENCE: 13

```
Gln Val Gln Leu Gln Glu Ser Gly Pro Glu Leu Val Lys Pro Gly Thr
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Thr His Gly Lys Asn Leu Glu Trp Ile
        35                  40                  45

Gly Arg Val Asn Pro Ser Asn Gly Asn Thr Asp Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Ser Ser Leu Thr Ser Glu Asp Ser Ala Val Tyr Tyr Cys
                85                  90                  95

Gly Arg Leu Ala Tyr Trp Gly Gln Gly Ser Leu Val Thr Val Ser Ala
            100                 105                 110
```

<210> SEQ ID NO 14
<211> LENGTH: 112
<212> TYPE: PRT
<213> ORGANISM: Artificial Sequence
<220> FEATURE:
<223> OTHER INFORMATION: fragment of antibody

<400> SEQUENCE: 14

```
Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Thr His Gly Lys Asn Leu Glu Trp Ile
        35                  40                  45

Gly Arg Val Asn Pro Ser Asn Gly Asn Thr Asp Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Ser Ser Leu Thr Ser Glu Asp Ser Ala Val Tyr Tyr Cys
                85                  90                  95

Gly Arg Leu Ala Tyr Trp Gly Gln Gly Ser Leu Val Thr Val Ser Ala
            100                 105                 110
```

<210> SEQ ID NO 15
<211> LENGTH: 111
<212> TYPE: PRT
<213> ORGANISM: Artificial Sequence
<220> FEATURE:
<223> OTHER INFORMATION: fragment of antibody

<400> SEQUENCE: 15

```
Asp Ile Val Leu Thr Gln Ser Pro Ala Ser Leu Ala Val Ser Pro Gly
1               5                   10                  15
```

Gln Arg Ala Thr Ile Ser Cys Lys Ala Ser Gln Ser Val Asp Tyr Asp
            20                  25                  30

Gly Glu Thr Tyr Met Asn Trp Tyr Gln Gln Lys Ser Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Leu Gln Thr Leu
                85                  90                  95

Lys Asn Pro Tyr Thr Phe Gly Gly Gly Thr Lys Leu Glu Ile Lys
            100                 105                 110

<210> SEQ ID NO 16
<211> LENGTH: 111
<212> TYPE: PRT
<213> ORGANISM: Artificial Sequence
<220> FEATURE:
<223> OTHER INFORMATION: fragment of antibody

<400> SEQUENCE: 16

Asp Ile Leu Leu Thr Gln Ser Pro Ala Ser Leu Ala Val Ser Pro Gly
1               5                   10                  15

Gln Arg Ala Thr Ile Ser Cys Lys Ala Ser Gln Ser Val Asp Tyr Asp
            20                  25                  30

Gly Glu Thr Tyr Met Asn Trp Tyr Gln Gln Lys Ser Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Leu Gln Thr Leu
                85                  90                  95

Lys Asn Pro Tyr Thr Phe Gly Gly Gly Thr Lys Leu Glu Ile Lys
            100                 105                 110

<210> SEQ ID NO 17
<211> LENGTH: 22
<212> TYPE: PRT
<213> ORGANISM: Artificial Sequence
<220> FEATURE:
<223> OTHER INFORMATION: P2A fragment

<400> SEQUENCE: 17

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 18
<211> LENGTH: 21
<212> TYPE: PRT
<213> ORGANISM: Artificial Sequence
<220> FEATURE:
<223> OTHER INFORMATION: T2A fragment

<400> SEQUENCE: 18

Gly Ser Gly Glu Gly Arg Gly Ser Leu Leu Thr Cys Gly Asp Val Glu
1               5                   10                  15

Glu Asn Pro Gly Pro

```
                        20

<210> SEQ ID NO 19
<211> LENGTH: 23
<212> TYPE: PRT
<213> ORGANISM: Artificial Sequence
<220> FEATURE:
<223> OTHER INFORMATION: E2A fragment

<400> SEQUENCE: 19

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 20
<211> LENGTH: 25
<212> TYPE: PRT
<213> ORGANISM: Artificial Sequence
<220> FEATURE:
<223> OTHER INFORMATION: F2A fragment

<400> SEQUENCE: 20

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 21
<211> LENGTH: 7
<212> TYPE: PRT
<213> ORGANISM: Artificial Sequence
<220> FEATURE:
<223> OTHER INFORMATION: fragment of antibody

<400> SEQUENCE: 21

Gly Tyr Thr Phe Thr Asp Tyr
1               5

<210> SEQ ID NO 22
<211> LENGTH: 10
<212> TYPE: PRT
<213> ORGANISM: Artificial Sequence
<220> FEATURE:
<223> OTHER INFORMATION: fragment of antibody

<400> SEQUENCE: 22

Gly Tyr Thr Phe Thr Asp Tyr Tyr Met Asn
1               5                   10

<210> SEQ ID NO 23
<211> LENGTH: 5
<212> TYPE: PRT
<213> ORGANISM: Artificial Sequence
<220> FEATURE:
<223> OTHER INFORMATION: fragment of antibody

<400> SEQUENCE: 23

Asp Tyr Tyr Met Asn
1               5

<210> SEQ ID NO 24
<211> LENGTH: 6
<212> TYPE: PRT
<213> ORGANISM: Artificial Sequence
<220> FEATURE:
```

<223> OTHER INFORMATION: fragment of antibody

<400> SEQUENCE: 24

Thr Asp Tyr Tyr Met Asn
1               5

<210> SEQ ID NO 25
<211> LENGTH: 6
<212> TYPE: PRT
<213> ORGANISM: Artificial Sequence
<220> FEATURE:
<223> OTHER INFORMATION: fragment of antibody

<400> SEQUENCE: 25

Asn Pro Ser Asn Gly Asn
1               5

<210> SEQ ID NO 26
<211> LENGTH: 10
<212> TYPE: PRT
<213> ORGANISM: Artificial Sequence
<220> FEATURE:
<223> OTHER INFORMATION: fragment of antibody

<400> SEQUENCE: 26

Arg Val Asn Pro Ser Asn Gly Asn Thr Asp
1               5                   10

<210> SEQ ID NO 27
<211> LENGTH: 17
<212> TYPE: PRT
<213> ORGANISM: Artificial Sequence
<220> FEATURE:
<223> OTHER INFORMATION: fragment of antibody

<400> SEQUENCE: 27

Arg Val Asn Pro Ser Asn Gly Asn Thr Asp Tyr Asn Gln Lys Phe Lys
1               5                   10                  15

Gly

<210> SEQ ID NO 28
<211> LENGTH: 13
<212> TYPE: PRT
<213> ORGANISM: Artificial Sequence
<220> FEATURE:
<223> OTHER INFORMATION: fragment of antibody

<400> SEQUENCE: 28

Trp Ile Gly Arg Val Asn Pro Ser Asn Gly Asn Thr Asp
1               5                   10

<210> SEQ ID NO 29
<211> LENGTH: 3
<212> TYPE: PRT
<213> ORGANISM: Artificial Sequence
<220> FEATURE:
<223> OTHER INFORMATION: fragment of antibody

<400> SEQUENCE: 29

Leu Ala Tyr
1

<210> SEQ ID NO 30
<211> LENGTH: 4
<212> TYPE: PRT
<213> ORGANISM: Artificial Sequence

```
<220> FEATURE:
<223> OTHER INFORMATION: fragment of antibody

<400> SEQUENCE: 30

Gly Arg Leu Ala
1

<210> SEQ ID NO 31
<211> LENGTH: 15
<212> TYPE: PRT
<213> ORGANISM: Artificial Sequence
<220> FEATURE:
<223> OTHER INFORMATION: fragment of antibody

<400> SEQUENCE: 31

Lys Ala Ser Gln Ser Val Asp Tyr Asp Gly Glu Thr Tyr Met Asn
1               5                   10                  15

<210> SEQ ID NO 32
<211> LENGTH: 11
<212> TYPE: PRT
<213> ORGANISM: Artificial Sequence
<220> FEATURE:
<223> OTHER INFORMATION: fragment of antibody

<400> SEQUENCE: 32

Asp Tyr Asp Gly Glu Thr Tyr Met Asn Trp Tyr
1               5                   10

<210> SEQ ID NO 33
<211> LENGTH: 7
<212> TYPE: PRT
<213> ORGANISM: Artificial Sequence
<220> FEATURE:
<223> OTHER INFORMATION: fragment of antibody

<400> SEQUENCE: 33

Ala Ala Ser Asn Leu Glu Ser
1               5

<210> SEQ ID NO 34
<211> LENGTH: 10
<212> TYPE: PRT
<213> ORGANISM: Artificial Sequence
<220> FEATURE:
<223> OTHER INFORMATION: fragment of antibody

<400> SEQUENCE: 34

Leu Leu Ile Tyr Ala Ala Ser Asn Leu Glu
1               5                   10

<210> SEQ ID NO 35
<211> LENGTH: 9
<212> TYPE: PRT
<213> ORGANISM: Artificial Sequence
<220> FEATURE:
<223> OTHER INFORMATION: fragment of antibody

<400> SEQUENCE: 35

Leu Gln Thr Leu Lys Asn Pro Tyr Thr
1               5

<210> SEQ ID NO 36
<211> LENGTH: 8
<212> TYPE: PRT
<213> ORGANISM: Artificial Sequence
<220> FEATURE:
```

<223> OTHER INFORMATION: fragment of antibody

<400> SEQUENCE: 36

Leu Gln Thr Leu Lys Asn Pro Tyr
1               5

<210> SEQ ID NO 37
<211> LENGTH: 106
<212> TYPE: PRT
<213> ORGANISM: Artificial Sequence
<220> FEATURE:
<223> OTHER INFORMATION: fragment of antibody

<400> SEQUENCE: 37

Ser Gly Pro Glu Leu Val Lys Pro Gly Thr Ser Val Lys Met Ser Cys
1               5                   10                  15

Lys Ala Ser Gly Tyr Thr Phe Thr Asp Tyr Tyr Met Asn Trp Val Lys
            20                  25                  30

Gln Thr His Gly Lys Asn Leu Glu Trp Ile Gly Arg Val Asn Pro Ser
        35                  40                  45

Asn Gly Asn Thr Asp Tyr Asn Gln Lys Phe Lys Gly Lys Ala Thr Leu
    50                  55                  60

Thr Val Asp Lys Ser Leu Ser Thr Ala Tyr Met Gln Leu Ser Ser Leu
65                  70                  75                  80

Thr Ser Glu Asp Ser Ala Val Tyr Tyr Cys Gly Arg Leu Ala Tyr Trp
                85                  90                  95

Gly Gln Gly Ser Leu Val Thr Val Ser Ala
            100                 105

<210> SEQ ID NO 38
<211> LENGTH: 108
<212> TYPE: PRT
<213> ORGANISM: Artificial Sequence
<220> FEATURE:
<223> OTHER INFORMATION: fragment of antibody

<400> SEQUENCE: 38

Leu Thr Gln Ser Pro Ala Ser Leu Ala Val Ser Pro Gly Gln Arg Ala
1               5                   10                  15

Thr Ile Ser Cys Lys Ala Ser Gln Ser Val Asp Tyr Asp Gly Glu Thr
            20                  25                  30

Tyr Met Asn Trp Tyr Gln Gln Lys Ser Gly Gln Pro Pro Lys Leu Leu
        35                  40                  45

Ile Tyr Ala Ala Ser Asn Leu Glu Ser Gly Ile Pro Ala Arg Phe Ser
    50                  55                  60

Gly Ser Gly Ser Gly Thr Asp Phe Thr Leu Asn Ile His Pro Val Glu
65                  70                  75                  80

Glu Glu Asp Ala Ala Thr Tyr Tyr Cys Leu Gln Thr Leu Lys Asn Pro
                85                  90                  95

Tyr Thr Phe Gly Gly Gly Thr Lys Leu Glu Ile Lys
            100                 105

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
agcgtgcgat tcaaaggatt                                                    20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
gactggtgcc gacgatgact                                                    20

<210> SEQ ID NO 41
<211> LENGTH: 19
<212> TYPE: DNA
<213> ORGANISM: Artificial Sequence
<220> FEATURE:
<223> OTHER INFORMATION: primer

<400> SEQUENCE: 41
gaaggtgaag gtcggagtc                                                     19

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
gaagatggtg atgggatttc                                                    20

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
tgcacaggag ccaagagtga a                                                  21

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
cacatcacag ctccccacca                                                    20

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
agcttgcgat tcaaaggatt                                                    20

<210> SEQ ID NO 46
<211> LENGTH: 20
<212> TYPE: DNA
<213> ORGANISM: Artificial Sequence

```
<220> FEATURE:
<223> OTHER INFORMATION: primer

<400> SEQUENCE: 46
gactggtggt gatgatgact                                                     20

<210> SEQ ID NO 47
<211> LENGTH: 19
<212> TYPE: DNA
<213> ORGANISM: Artificial Sequence
<220> FEATURE:
<223> OTHER INFORMATION: primer

<400> SEQUENCE: 47
gaaggtgaag gtcggagtc                                                      19

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
gaagatggtg atgggcttc                                                      20

<210> SEQ ID NO 49
<211> LENGTH: 21
<212> TYPE: DNA
<213> ORGANISM: Artificial Sequence
<220> FEATURE:
<223> OTHER INFORMATION: primer

<400> SEQUENCE: 49
tgcacaggag ccaagagtga a                                                   21

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
cacatcacag ctccccacca                                                     20

<210> SEQ ID NO 51
<211> LENGTH: 534
<212> TYPE: PRT
<213> ORGANISM: Artificial Sequence
<220> FEATURE:
<223> OTHER INFORMATION: fragment of human ROR1

<400> SEQUENCE: 51
```

Ile Leu Tyr Ile Leu Val Pro Ser Val Ala Ile Pro Leu Ala Ile Ala
 1               5                  10                  15

Leu Leu Phe Phe Phe Ile Cys Val Cys Arg Asn Asn Gln Lys Ser Ser
                20                  25                  30

Ser Ala Pro Val Gln Arg Gln Pro Lys His Val Arg Gly Gln Asn Val
            35                  40                  45

Glu Met Ser Met Leu Asn Ala Tyr Lys Pro Lys Ser Lys Ala Lys Glu
        50                  55                  60

Leu Pro Leu Ser Ala Val Arg Phe Met Glu Glu Leu Gly Glu Cys Ala
65                  70                  75                  80

```
Phe Gly Lys Ile Tyr Lys Gly His Leu Tyr Leu Pro Gly Met Asp His
                85                  90                  95

Ala Gln Leu Val Ala Ile Lys Thr Leu Lys Asp Tyr Asn Asn Pro Gln
            100                 105                 110

Gln Trp Thr Glu Phe Gln Gln Glu Ala Ser Leu Met Ala Glu Leu His
        115                 120                 125

His Pro Asn Ile Val Cys Leu Leu Gly Ala Val Thr Gln Glu Gln Pro
    130                 135                 140

Val Cys Met Leu Phe Glu Tyr Ile Asn Gln Gly Asp Leu His Glu Phe
145                 150                 155                 160

Leu Ile Met Arg Ser Pro His Ser Asp Val Gly Cys Ser Ser Asp Glu
                165                 170                 175

Asp Gly Thr Val Lys Ser Ser Leu Asp His Gly Asp Phe Leu His Ile
            180                 185                 190

Ala Ile Gln Ile Ala Ala Gly Met Glu Tyr Leu Ser Ser His Phe Phe
        195                 200                 205

Val His Lys Asp Leu Ala Ala Arg Asn Ile Leu Ile Gly Glu Gln Leu
    210                 215                 220

His Val Lys Ile Ser Asp Leu Gly Leu Ser Arg Glu Ile Tyr Ser Ala
225                 230                 235                 240

Asp Tyr Tyr Arg Val Gln Ser Lys Ser Leu Leu Pro Ile Arg Trp Met
                245                 250                 255

Pro Pro Glu Ala Ile Met Tyr Gly Lys Phe Ser Ser Asp Ser Asp Ile
            260                 265                 270

Trp Ser Phe Gly Val Val Leu Trp Glu Ile Phe Ser Phe Gly Leu Gln
        275                 280                 285

Pro Tyr Tyr Gly Phe Ser Asn Gln Glu Val Ile Glu Met Val Arg Lys
    290                 295                 300

Arg Gln Leu Leu Pro Cys Ser Glu Asp Cys Pro Pro Arg Met Tyr Ser
305                 310                 315                 320

Leu Met Thr Glu Cys Trp Asn Glu Ile Pro Ser Arg Arg Pro Arg Phe
                325                 330                 335

Lys Asp Ile His Val Arg Leu Arg Ser Trp Glu Gly Leu Ser Ser His
            340                 345                 350

Thr Ser Ser Thr Thr Pro Ser Gly Gly Asn Ala Thr Thr Gln Thr Thr
        355                 360                 365

Ser Leu Ser Ala Ser Pro Val Ser Asn Leu Ser Asn Pro Arg Tyr Pro
370                 375                 380

Asn Tyr Met Phe Pro Ser Gln Gly Ile Thr Pro Gln Gly Gln Ile Ala
385                 390                 395                 400

Gly Phe Ile Gly Pro Pro Ile Pro Gln Asn Gln Arg Phe Ile Pro Ile
                405                 410                 415

Asn Gly Tyr Pro Ile Pro Pro Gly Tyr Ala Ala Phe Pro Ala Ala His
            420                 425                 430

Tyr Gln Pro Thr Gly Pro Pro Arg Val Ile Gln His Cys Pro Pro Pro
        435                 440                 445

Lys Ser Arg Ser Pro Ser Ser Ala Ser Gly Ser Thr Ser Thr Gly His
    450                 455                 460

Val Thr Ser Leu Pro Ser Ser Gly Ser Asn Gln Glu Ala Asn Ile Pro
465                 470                 475                 480

Leu Leu Pro His Met Ser Ile Pro Asn His Pro Gly Gly Met Gly Ile
                485                 490                 495
```

```
Thr Val Phe Gly Asn Lys Ser Gln Lys Pro Tyr Lys Ile Asp Ser Lys
            500                 505                 510

Gln Ala Ser Leu Leu Gly Asp Ala Asn Ile His Gly Thr His Thr Glu Ser
            515                 520                     525

Met Ile Ser Ala Glu Leu
        530
```

<210> SEQ ID NO 52
<211> LENGTH: 937
<212> TYPE: PRT
<213> ORGANISM: Mus musculus

<400> SEQUENCE: 52

```
Met His Arg Pro Arg Arg Gly Thr Arg Pro Pro Leu Ala Leu
1               5                   10                  15

Leu Ala Ala Leu Leu Ala Ala Arg Gly Ala Asp Ala Gln Glu Thr
            20                  25                  30

Glu Leu Ser Val Ser Ala Glu Leu Val Pro Thr Ser Ser Trp Asn Thr
            35                  40                      45

Ser Ser Glu Ile Asp Lys Gly Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Ser Ile Arg Trp Phe Lys Asn Asp Ala
                85                  90                  95

Pro Val Val Gln Glu Pro Arg Arg Ile Ser Phe Arg Ala Thr Asn Tyr
            100                 105                 110

Gly Ser Arg Leu Arg Ile Arg Asn Leu Asp Thr Thr Asp Thr Gly Tyr
            115                 120                 125

Phe Gln Cys Val Ala Thr Asn Gly Lys Lys Val Val Ser Thr Thr Gly
    130                 135                 140

Val Leu Phe Val Lys Phe Gly Pro Pro Thr Ala Ser Pro Gly Ser
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Val Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335
```

```
Trp Asn Ser Gln Tyr Pro His Thr His Ser Phe Thr Ala Leu Arg Phe
            340                 345                 350
Pro Glu Leu Asn Gly Gly His Ser Tyr Cys Arg Asn Pro Gly Asn Gln
            355                 360                 365
Lys Glu Ala Pro Trp Cys Phe Thr Leu Asp Glu Asn Phe Lys Ser Asp
            370                 375                 380
Leu Cys Asp Ile Pro Ala Cys Asp Ser Lys Asp Ser Lys Glu Lys Asn
385                 390                 395                 400
Lys Met Glu Ile Leu Tyr Ile Leu Val Pro Ser Val Ala Ile Pro Leu
            405                 410                 415
Ala Ile Ala Phe Leu Phe Phe Phe Ile Cys Val Cys Arg Asn Asn Gln
            420                 425                 430
Lys Ser Ser Ser Pro Pro Val Gln Arg Gln Pro Lys Pro Val Arg Gly
            435                 440                 445
Gln Asn Val Glu Met Ser Met Leu Asn Ala Tyr Lys Pro Lys Ser Lys
            450                 455                 460
Ala Lys Glu Leu Pro Leu Ser Ala Val Arg Phe Met Glu Glu Leu Gly
465                 470                 475                 480
Glu Cys Thr Phe Gly Lys Ile Tyr Lys Gly His Leu Tyr Leu Pro Gly
            485                 490                 495
Met Asp His Ala Gln Leu Val Ala Ile Lys Thr Leu Lys Asp Tyr Asn
            500                 505                 510
Asn Pro Gln Gln Trp Thr Glu Phe Gln Gln Glu Ala Ser Leu Met Ala
            515                 520                 525
Glu Leu His His Pro Asn Ile Val Cys Leu Leu Gly Ala Val Thr Gln
            530                 535                 540
Glu Gln Pro Val Cys Met Leu Phe Glu Tyr Met Asn Gln Gly Asp Leu
545                 550                 555                 560
His Glu Phe Leu Ile Met Arg Ser Pro His Ser Asp Val Gly Cys Ser
            565                 570                 575
Ser Asp Glu Asp Gly Thr Val Lys Ser Ser Leu Asp His Gly Asp Phe
            580                 585                 590
Leu His Ile Ala Ile Gln Ile Ala Ala Gly Met Glu Tyr Leu Ser Ser
            595                 600                 605
His Phe Phe Val His Lys Asp Leu Ala Ala Arg Asn Ile Leu Ile Gly
            610                 615                 620
Glu Gln Leu His Val Lys Ile Ser Asp Leu Gly Leu Ser Arg Glu Ile
625                 630                 635                 640
Tyr Ser Ala Asp Tyr Tyr Arg Val Gln Ser Lys Ser Ser Leu Pro Ile
            645                 650                 655
Arg Trp Met Pro Pro Glu Ala Ile Met Tyr Gly Lys Phe Ser Ser Asp
            660                 665                 670
Ser Asp Ile Trp Ser Phe Gly Val Val Leu Trp Glu Ile Phe Ser Phe
            675                 680                 685
Gly Leu Gln Pro Tyr Tyr Gly Phe Ser Asn Gln Glu Val Ile Glu Met
            690                 695                 700
Val Arg Lys Arg Gln Leu Leu Pro Cys Ser Glu Asp Cys Pro Pro Arg
705                 710                 715                 720
Met Tyr Ser Leu Met Thr Glu Cys Trp Asn Glu Ile Pro Ser Arg Arg
            725                 730                 735
Pro Arg Phe Lys Asp Ile His Val Arg Leu Arg Ser Trp Glu Gly Leu
            740                 745                 750
```

```
Ser Ser His Thr Ser Ser Thr Thr Pro Ser Gly Gly Asn Ala Thr Thr
            755                 760                 765

Gln Thr Thr Ser Leu Ser Ala Ser Pro Val Ser Asn Leu Ser Asn Pro
    770                 775                 780

Arg Phe Pro Asn Tyr Met Phe Pro Ser Gln Gly Ile Thr Pro Gln Gly
785                 790                 795                 800

Gln Ile Ala Gly Phe Ile Gly Pro Ala Ile Pro Gln Asn Gln Arg Phe
                805                 810                 815

Ile Pro Ile Asn Gly Tyr Pro Ile Pro Pro Gly Tyr Ala Ala Phe Pro
                820                 825                 830

Ala Ala His Tyr Gln Pro Ala Gly Pro Pro Arg Val Ile Gln His Cys
            835                 840                 845

Pro Pro Pro Lys Ser Arg Ser Pro Ser Ser Ala Ser Gly Ser Thr Ser
    850                 855                 860

Thr Gly His Val Ala Ser Leu Pro Ser Ser Gly Ser Asn Gln Glu Ala
865                 870                 875                 880

Asn Val Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
            900                 905                 910

Asp Ser Lys Gln Ser Ser Leu Leu Gly Asp Ser His Ile His Gly His
    915                 920                 925

Thr Glu Ser Met Ile Ser Ala Glu Val
    930                 935

<210> SEQ ID NO 53
<211> LENGTH: 534
<212> TYPE: PRT
<213> ORGANISM: Artificial Sequence
<220> FEATURE:
<223> OTHER INFORMATION: fragment of mouse ROR1

<400> SEQUENCE: 53

Ile Leu Tyr Ile Leu Val Pro Ser Val Ala Ile Pro Leu Ala Ile Ala
1               5                   10                  15

Phe Leu Phe Phe Phe Ile Cys Val Cys Arg Asn Asn Gln Lys Ser Ser
            20                  25                  30

Ser Pro Pro Val Gln Arg Gln Pro Lys Pro Val Arg Gly Gln Asn Val
        35                  40                  45

Glu Met Ser Met Leu Asn Ala Tyr Lys Pro Lys Ser Lys Ala Lys Glu
    50                  55                  60

Leu Pro Leu Ser Ala Val Arg Phe Met Glu Glu Leu Gly Glu Cys Thr
65                  70                  75                  80

Phe Gly Lys Ile Tyr Lys Gly His Leu Tyr Leu Pro Gly Met Asp His
                85                  90                  95

Ala Gln Leu Val Ala Ile Lys Thr Leu Lys Asp Tyr Asn Asn Pro Gln
            100                 105                 110

Gln Trp Thr Glu Phe Gln Gln Glu Ala Ser Leu Met Ala Glu Leu His
        115                 120                 125

His Pro Asn Ile Val Cys Leu Leu Gly Ala Val Thr Gln Glu Gln Pro
    130                 135                 140

Val Cys Met Leu Phe Glu Tyr Met Asn Gln Gly Asp Leu His Glu Phe
145                 150                 155                 160

Leu Ile Met Arg Ser Pro His Ser Asp Val Gly Cys Ser Ser Asp Glu
                165                 170                 175
```

-continued

Asp Gly Thr Val Lys Ser Ser Leu Asp His Gly Asp Phe Leu His Ile
            180                 185                 190

Ala Ile Gln Ile Ala Ala Gly Met Glu Tyr Leu Ser Ser His Phe Phe
        195                 200                 205

Val His Lys Asp Leu Ala Ala Arg Asn Ile Leu Ile Gly Glu Gln Leu
    210                 215                 220

His Val Lys Ile Ser Asp Leu Gly Leu Ser Arg Glu Ile Tyr Ser Ala
225                 230                 235                 240

Asp Tyr Tyr Arg Val Gln Ser Lys Ser Leu Pro Ile Arg Trp Met
                245                 250                 255

Pro Pro Glu Ala Ile Met Tyr Gly Lys Phe Ser Ser Asp Ser Asp Ile
            260                 265                 270

Trp Ser Phe Gly Val Val Leu Trp Glu Ile Phe Ser Phe Gly Leu Gln
        275                 280                 285

Pro Tyr Tyr Gly Phe Ser Asn Gln Glu Val Ile Glu Met Val Arg Lys
    290                 295                 300

Arg Gln Leu Leu Pro Cys Ser Glu Asp Cys Pro Pro Arg Met Tyr Ser
305                 310                 315                 320

Leu Met Thr Glu Cys Trp Asn Glu Ile Pro Ser Arg Arg Pro Arg Phe
                325                 330                 335

Lys Asp Ile His Val Arg Leu Arg Ser Trp Glu Gly Leu Ser Ser His
            340                 345                 350

Thr Ser Ser Thr Thr Pro Ser Gly Gly Asn Ala Thr Thr Gln Thr Thr
        355                 360                 365

Ser Leu Ser Ala Ser Pro Val Ser Asn Leu Ser Asn Pro Arg Phe Pro
    370                 375                 380

Asn Tyr Met Phe Pro Ser Gln Gly Ile Thr Pro Gln Gly Gln Ile Ala
385                 390                 395                 400

Gly Phe Ile Gly Pro Ala Ile Pro Gln Asn Gln Arg Phe Ile Pro Ile
                405                 410                 415

Asn Gly Tyr Pro Ile Pro Pro Gly Tyr Ala Ala Phe Pro Ala Ala His
            420                 425                 430

Tyr Gln Pro Ala Gly Pro Pro Arg Val Ile Gln His Cys Pro Pro Pro
        435                 440                 445

Lys Ser Arg Ser Pro Ser Ser Ala Ser Gly Ser Thr Ser Thr Gly His
    450                 455                 460

Val Ala Ser Leu Pro Ser Ser Gly Ser Asn Gln Glu Ala Asn Val Pro
465                 470                 475                 480

Leu Leu Pro His Met Ser Ile Pro Asn His Pro Gly Gly Met Gly Ile
                485                 490                 495

Thr Val Phe Gly Asn Lys Ser Gln Lys Pro Tyr Lys Ile Asp Ser Lys
            500                 505                 510

Gln Ser Ser Leu Leu Gly Asp Ser His Ile His Gly His Thr Glu Ser
        515                 520                 525

Met Ile Ser Ala Glu Val
    530

<210> SEQ ID NO 54
<211> LENGTH: 17
<212> TYPE: PRT
<213> ORGANISM: Artificial Sequence
<220> FEATURE:
<223> OTHER INFORMATION: fragment of human ROR1

<400> SEQUENCE: 54

Glu Ala Asn Ile Pro Leu Leu Pro His Met Ser Ile Pro Asn His Pro
1               5                   10                  15

Gly

<210> SEQ ID NO 55
<211> LENGTH: 16
<212> TYPE: PRT
<213> ORGANISM: Artificial Sequence
<220> FEATURE:
<223> OTHER INFORMATION: fragment of human ROR1

<400> SEQUENCE: 55

Ile Asp Ser Lys Gln Ala Ser Leu Leu Gly Asp Ala Asn Ile His Gly
1               5                   10                  15

<210> SEQ ID NO 56
<211> LENGTH: 943
<212> TYPE: PRT
<213> ORGANISM: Homo sapiens

<400> SEQUENCE: 56

Met Ala Arg Gly Ser Ala Leu Pro Arg Pro Leu Leu Cys Ile Pro
1               5                   10                  15

Ala Val Trp Ala Ala Ala Leu Leu Leu Ser Val Ser Arg Thr Ser
                20                  25                  30

Gly Glu Val Glu Val Leu Asp Pro Asn Asp Pro Leu Gly Pro Leu Asp
                35                  40                  45

Gly Gln Asp Gly Pro Ile Pro Thr Leu Lys Gly Tyr Phe Leu Asn Phe
            50                  55                  60

Leu Glu Pro Val Asn Asn Ile Thr Ile Val Gln Gly Gln Thr Ala Ile
65              70                  75                  80

Leu His Cys Lys Val Ala Gly Asn Pro Pro Asn Val Arg Trp Leu
                85                  90                  95

Lys Asn Asp Ala Pro Val Val Gln Glu Pro Arg Arg Ile Ile Ile Arg
                100                 105                 110

Lys Thr Glu Tyr Gly Ser Arg Leu Arg Ile Gln Asp Leu Asp Thr Thr
                115                 120                 125

Asp Thr Gly Tyr Tyr Gln Cys Val Ala Thr Asn Gly Met Lys Thr Ile
            130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
                180                 185                 190

Val Asp Ser Leu Gln Met Gln Gly Glu Ile Glu Asn Arg Ile Thr Ala
            195                 200                 205

Ala Phe Thr Met Ile Gly Thr Ser Thr His Leu Ser Asp Gln Cys Ser
        210                 215                 220

Gln Phe Ala Ile Pro Ser Phe Cys His Phe Val Phe Pro Leu Cys Asp
225                 230                 235                 240

Ala Arg Ser Arg Thr Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
                260                 265                 270

Ser Asn Pro Leu Ile Leu Met Arg Leu Gln Leu Pro Lys Cys Glu Ala
            275                 280                 285

```
Leu Pro Met Pro Glu Ser Pro Asp Ala Ala Asn Cys Met Arg Ile Gly
    290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
                325                 330                 335

Cys Gln Pro Trp Ala Leu Gln His Pro His Ser His His Leu Ser Ser
                340                 345                 350

Thr Asp Phe Pro Glu Leu Gly Gly His Ala Tyr Cys Arg Asn Pro
            355                 360                 365

Gly Gly Gln Met Glu Gly Pro Trp Cys Phe Thr Gln Asn Lys Asn Val
370                 375                 380

Arg Met Glu Leu Cys Asp Val Pro Ser Cys Ser Pro Arg Asp Ser Ser
385                 390                 395                 400

Lys Met Gly Ile Leu Tyr Ile Leu Val Pro Ser Ile Ala Ile Pro Leu
                405                 410                 415

Val Ile Ala Cys Leu Phe Phe Leu Val Cys Met Cys Arg Asn Lys Gln
                420                 425                 430

Lys Ala Ser Ala Ser Thr Pro Gln Arg Arg Gln Leu Met Ala Ser Pro
            435                 440                 445

Ser Gln Asp Met Glu Met Pro Leu Ile Asn Gln His Lys Gln Ala Lys
450                 455                 460

Leu Lys Glu Ile Ser Leu Ser Ala Val Arg Phe Met Glu Glu Leu Gly
465                 470                 475                 480

Glu Asp Arg Phe Gly Lys Val Tyr Lys Gly His Leu Phe Gly Pro Ala
                485                 490                 495

Pro Gly Glu Gln Thr Gln Ala Val Ala Ile Lys Thr Leu Lys Asp Lys
            500                 505                 510

Ala Glu Gly Pro Leu Arg Glu Glu Phe Arg His Glu Ala Met Leu Arg
            515                 520                 525

Ala Arg Leu Gln His Pro Asn Val Val Cys Leu Leu Gly Val Val Thr
            530                 535                 540

Lys Asp Gln Pro Leu Ser Met Ile Phe Ser Tyr Cys Ser His Gly Asp
545                 550                 555                 560

Leu His Glu Phe Leu Val Met Arg Ser Pro His Ser Asp Val Gly Ser
                565                 570                 575

Thr Asp Asp Asp Arg Thr Val Lys Ser Ala Leu Glu Pro Pro Asp Phe
            580                 585                 590

Val His Leu Val Ala Gln Ile Ala Ala Gly Met Glu Tyr Leu Ser Ser
            595                 600                 605

His His Val Val His Lys Asp Leu Ala Thr Arg Asn Val Leu Val Tyr
610                 615                 620

Asp Lys Leu Asn Val Lys Ile Ser Asp Leu Gly Leu Phe Arg Glu Val
625                 630                 635                 640

Tyr Ala Ala Asp Tyr Tyr Lys Leu Leu Gly Asn Ser Leu Leu Pro Ile
                645                 650                 655

Arg Trp Met Ala Pro Glu Ala Ile Met Tyr Gly Lys Phe Ser Ile Asp
            660                 665                 670

Ser Asp Ile Trp Ser Tyr Gly Val Val Leu Trp Glu Val Phe Ser Tyr
            675                 680                 685

Gly Leu Gln Pro Tyr Cys Gly Tyr Ser Asn Gln Asp Val Val Glu Met
    690                 695                 700
```

```
Ile Arg Asn Arg Gln Val Leu Pro Cys Pro Asp Cys Pro Ala Trp
705                 710                 715                 720

Val Tyr Ala Leu Met Ile Glu Cys Trp Asn Glu Phe Pro Ser Arg Arg
            725                 730                 735

Pro Arg Phe Lys Asp Ile His Ser Arg Leu Arg Ala Trp Gly Asn Leu
                740                 745                 750

Ser Asn Tyr Asn Ser Ser Ala Gln Thr Ser Gly Ala Ser Asn Thr Thr
            755                 760                 765

Gln Thr Ser Ser Leu Ser Thr Ser Pro Val Ser Asn Val Ser Asn Ala
    770                 775                 780

Arg Tyr Val Gly Pro Lys Gln Lys Ala Pro Pro Phe Pro Gln Pro Gln
785                 790                 795                 800

Phe Ile Pro Met Lys Gly Gln Ile Arg Pro Met Val Pro Pro Pro Gln
                805                 810                 815

Leu Tyr Val Pro Val Asn Gly Tyr Gln Pro Val Pro Ala Tyr Gly Ala
                820                 825                 830

Tyr Leu Pro Asn Phe Tyr Pro Val Gln Ile Pro Met Gln Met Ala Pro
            835                 840                 845

Gln Gln Val Pro Pro Gln Met Val Pro Lys Pro Ser Ser His His Ser
    850                 855                 860

Gly Ser Gly Ser Thr Ser Thr Gly Tyr Val Thr Thr Ala Pro Ser Asn
865                 870                 875                 880

Thr Ser Met Ala Asp Arg Ala Ala Leu Leu Ser Glu Gly Ala Asp Asp
                885                 890                 895

Thr Gln Asn Ala Pro Glu Asp Gly Ala Gln Ser Thr Val Gln Glu Ala
            900                 905                 910

Glu Glu Glu Glu Glu Gly Ser Val Pro Glu Thr Glu Leu Leu Gly Asp
            915                 920                 925

Cys Asp Thr Leu Gln Val Asp Glu Ala Gln Val Gln Leu Glu Ala
            930                 935                 940

<210> SEQ ID NO 57
<211> LENGTH: 29
<212> TYPE: PRT
<213> ORGANISM: Artificial Sequence
<220> FEATURE:
<223> OTHER INFORMATION: fragment of mouse ROR1

<400> SEQUENCE: 57

Asn Pro Arg Phe Pro Asn Tyr Met Phe Pro Ser Gln Gly Ile Thr Pro
1               5                   10                  15

Gln Gly Gln Ile Ala Gly Phe Ile Gly Pro Ala Ile Pro
            20                  25

<210> SEQ ID NO 58
<211> LENGTH: 937
<212> TYPE: PRT
<213> ORGANISM: Macacca mulatta

<400> SEQUENCE: 58

Met His Arg Pro Arg Arg Arg Gly Thr Arg Pro Pro Leu Leu Ala Leu
1               5                   10                  15

Leu Ala Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
```

```
            50                  55                  60
Asn Asn Ile Thr Thr Ser Leu Gly Gln Thr Ala Glu Leu His Cys Lys
 65                  70                  75                  80

Val Ser Gly Asn Pro Pro Thr Ile Arg Trp Phe Lys Asn Asp Ala
                 85                  90                  95

Pro Val Val Gln Glu Pro Arg Arg Leu Ser Phe Arg Ser Thr Ile Tyr
                100                 105                 110

Gly Ser Arg Leu Arg Ile Arg Asn Leu Asp Thr Thr Asp Thr Gly Tyr
                115                 120                 125

Phe Gln Cys Val Ala Thr Asn Gly Lys Glu Val Val Ser Ser Thr Gly
130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
                180                 185                 190

His Met Gln Gly Glu Ile Glu Asn Gln Ile Thr Ala Ala Phe Thr Met
                195                 200                 205

Ile Gly Thr Ser Ser His Leu Ser Asp Lys Cys Ser Gln Phe Ala Ile
210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
                260                 265                 270

Ile Leu Met Arg Leu Lys Leu Pro Asn Cys Glu Asp Leu Pro Gln Pro
                275                 280                 285

Glu Ser Pro Glu Ala Ala Asn Cys Ile Arg Ile Gly Ile Pro Met Ala
                290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
                340                 345                 350

Pro Glu Leu Asn Gly Gly His Ser Tyr Cys Arg Asn Pro Gly Asn Gln
                355                 360                 365

Lys Glu Ala Pro Trp Cys Phe Thr Leu Asp Glu Asn Phe Lys Ser Asp
                370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
                420                 425                 430

Lys Ser Ser Ser Pro Pro Val Gln Arg Gln Pro Lys His Val Arg Gly
                435                 440                 445

Gln Asn Val Glu Met Ser Met Leu Asn Ala Tyr Lys Pro Lys Ser Lys
                450                 455                 460

Ala Lys Glu Leu Pro Leu Ser Ala Val Arg Phe Met Glu Glu Leu Gly
465                 470                 475                 480
```

```
Glu Cys Ala Phe Gly Lys Ile Tyr Lys Gly His Leu Tyr Leu Pro Gly
            485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
            515                 520                 525

Glu Leu His His Pro Asn Ile Val Cys Leu Leu Gly Ala Val Thr Gln
            530                 535                 540

Glu Gln Pro Val Cys Met Leu Phe Glu Tyr Met Asn Gln Gly Asp Leu
545                 550                 555                 560

His Glu Phe Leu Ile Met Arg Ser Pro His Ser Asp Val Gly Cys Ser
            565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
            595                 600                 605

His Phe Phe Val His Lys Asp Leu Ala Ala Arg Asn Ile Leu Ile Gly
            610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
            645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
            675                 680                 685

Gly Leu Gln Pro Tyr Tyr Gly Phe Ser Asn Gln Glu Val Ile Glu Met
            690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
            725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
            755                 760                 765

Gln Thr Thr Ser Leu Ser Ala Ser Pro Val Ser Asn Leu Ser Asn Pro
            770                 775                 780

Arg Tyr Pro Asn Tyr Ile Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
            805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
            835                 840                 845

Pro Pro Pro Lys Ser Arg Ser Pro Ser Ser Ala Ser Gly Ser Thr Ser
            850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
            885                 890                 895
```

-continued

```
Met Gly Ile Thr Val Phe Gly Asn Lys Ser Gln Lys Pro Tyr Lys Ile
            900                 905                 910

Asp Ala Lys Gln Ala Ser Leu Leu Gly Asp Ala Asn Ile His Gly His
        915                 920                 925

Thr Glu Ser Met Ile Ser Ala Glu Leu
    930                 935

<210> SEQ ID NO 59
<211> LENGTH: 29
<212> TYPE: PRT
<213> ORGANISM: Artificial Sequence
<220> FEATURE:
<223> OTHER INFORMATION: fragment of rhesus ROR1

<400> SEQUENCE: 59

Asn Pro Arg Tyr Pro Asn Tyr Ile Phe Pro Ser Gln Gly Ile Thr Pro
1               5                   10                  15

Gln Gly Gln Ile Ala Gly Phe Ile Gly Pro Pro Ile Pro
            20                  25
```

ANTI-ROR1 ANTIBODIES AND USES THEREOF

STATEMENT OF GOVERNMENT INTEREST

This invention was made with government support under CA114536 and CA138293 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056 437_D1_SEQUENCE_LISTING. The text file is 52.2 KB, was created on Jan. 25, 2021, and is being submitted electronically via EFS-Web.

BACKGROUND

The receptor tyrosine kinase ROR1 is an oncofetal antigen that is overexpressed in a wide variety of tumors, yet overexpressed in very few normal tissues. ROR1 is highly expressed in B-cell chronic lymphocytic leukemia (CLL), mantle cell lymphoma (MCL), and in some epithelial cancers. Human ROR1 is encoded by the gene Ror1, which encodes two putative splice variants: a 937 amino acid full-length isoform that localizes to the cell surface (ROR1_v1), and a short (truncated) 393 amino acid isoform containing primarily the N-terminal portion of full-length ROR1 that remains localized intracellularly (ROR1_v2) (Hudecek et al., *Blood* 116:4532, 2010).

Based on high expression of ROR1 on the cell surface of tumors and minimal ROR1 expression in normal tissues, ROR1 is a good tumor-specific or tumor-associated antigen to target with therapeutics. For example, T cells expressing a chimeric antigen receptor (CAR) have been designed to target ROR1-expressing tumors (Hudecek et al., *Blood* 116: 4532-41, 2010). To determine whether a patient has a malignancy that expresses ROR1 and is suitable for a ROR1-specific therapy, it is important to have a diagnostic reagent capable of detecting expression of endogenous ROR1 in cells of the subject, such as those in a sample obtained from the subject, e.g., a form of ROR1 that is expressed on the cell surface, such as cell-surface-expressed, full-length ROR1 molecules, in, for example, histologic sections.

Immunohistochemistry (IHC) is a common technique used in medical diagnostics for determining the presence or absence of proteins in tissues. Tumor tissues are routinely formalin-fixed-and-paraffin-embedded (FFPE tissues) before they are subjected to IHC analysis. Accordingly, a ROR1 diagnostic antibody should be able to detect endogenously expressed ROR1 in histologic samples. Commercially available anti-ROR1 antibodies do not effectively detect endogenous ROR1 in FFPE tissues. Furthermore, most commercial antibodies target the N-terminal portion of ROR1 and may not detect the difference between full-length ROR1 and the short ROR1 isoform containing only the amino-terminal portion of full-length ROR1.

Therefore, there remains a need for antibodies useful for detecting and quantifying endogenously expressed ROR1. The present disclosure meets such needs, and further provides other related advantages.

BRIEF SUMMARY

In certain aspects, the present disclosure is directed to a binding protein that specifically binds to a portion of a ROR1 that is C-terminal to an intracellular protein kinase domain of the ROR1, wherein the binding protein optionally is an immunoglobulin-like binding protein and/or is or comprises an antibody or antigen-binding fragment thereof.

In other aspects, the present disclosure provides a binding protein that specifically binds to (i) a peptide comprising SEQ ID NO.:3, wherein the peptide optionally consists of SEQ ID NO.:3, and/or (ii) an epitope of a ROR1 protein, which epitope (a) is within the amino acid sequence set forth in SEQ ID NO.:3 and/or (b) comprises one or more amino acids within the amino acid sequence set forth in SEQ ID NO.:3.

In still other aspects, a binding protein comprising an antibody or fragment thereof is provided, comprising a light chain variable domain ($V_L$) that is at least 90% identical to an amino acid sequence as set forth in SEQ ID NO.:15 or 16, and a heavy chain variable domain ($V_H$) that is at least 90% identical to an amino acid sequence as set forth in SEQ ID NO.:12, 13, or 14, wherein the antibody optionally specifically binds to (i) a peptide comprising SEQ ID NO.:3, wherein the peptide optionally consists of SEQ ID NO.:3, and/or (ii) an epitope of a ROR1 protein, which epitope (a) is within the amino acid sequence set forth in SEQ ID NO.:3 and/or (b) comprises one or more amino acids within the amino acid sequence set forth in SEQ ID NO.:3.

In still other aspects, the present disclosure provides a binding protein that competes with a reference binding protein or immunoglobulin like binding protein for specific binding to an ROR1 epitope located C terminal to an intracellular protein kinase domain of ROR1. In some embodiments, the present disclosure provides a binding protein that competes with a reference protein for binding to a peptide of SEQ ID NO: 3.

In certain aspects, the present disclosure is directed to a composition comprising a binding protein as described herein.

In certain aspects, the present disclosure is directed to a polynucleotide encoding a binding protein as described herein.

In certain aspects, the present disclosure is directed to an expression construct comprising a polynucleotide that encodes a binding protein as described herein.

In certain other aspects, the present disclosure is directed to a host cell comprising an expression construct, or a polynucleotide provided by an expression construct, as described herein.

In certain other aspects, a process for making a binding protein according to the disclosure is provided, comprising culturing a host cell comprising an expression construct, or a polynucleotide provided by an expression construct, under suitable conditions to express the binding protein, and optionally isolating the binding protein from the culture.

In certain other aspects, a method for identifying a cell that expresses full-length ROR1 is provided, comprising contacting a cell with a binding protein as disclosed herein and detecting specific binding of the binding protein to the cell, thereby identifying the cells that express full length ROR1.

In certain other aspects, the present disclosure provides a detection method, comprising (a) contacting a biological sample with a binding protein or composition as disclosed herein; and (b) detecting specific binding of the binding protein to a peptide or epitope in the sample, or lack thereof, wherein the method thereby detects the presence or absence of a ROR1 or a ROR1 epitope in the sample.

In certain other aspects, the present disclosure provides a method for identifying the presence of a ROR1 in a tissue sample, comprising contacting a tissue sample with a binding protein as disclosed herein and detecting specific binding of the binding protein to the tissue, thereby identifying tissue that expresses the ROR1, which optionally is full-length and/or cell-surface ROR1.

In certain other aspects, a method for identifying a subject having or at risk of having a disease associated with cells expressing full-length ROR1 is provided, comprising contacting a tissue sample from the subject with a binding protein and detecting specific binding of the binding protein to the tissue, thereby identifying a subject having or at risk of having a disease associated with cells expressing full-length ROR1.

In certain other aspects, a method for identifying whether a subject having a hyperproliferative disease or condition would benefit from an ROR1-specific treatment is provided, comprising contacting a tissue sample from the subject with a binding protein as disclosed herein and detecting specific binding of the binding protein to the tissue, thereby identifying whether or not the subject would benefit from an ROR1-specific treatment.

In certain other aspects, a method for identifying whether a subject having a hyperproliferative disease or condition would benefit from an ROR1-specific treatment is provided, comprising contacting a tissue sample from the subject with a binding protein as disclosed herein and detecting specific binding of the binding protein to the tissue, thereby identifying whether or not the subject would benefit from an ROR1-specific treatment.

In certain other aspects, a method for determining the prognosis of a subject having a hyperproliferative disease or condition associated with cells expressing full-length ROR1 is provided, comprising contacting a tissue sample from the subject with a binding protein as disclosed herein and detecting specific binding of the binding protein to the tissue, wherein detecting specific binding identifies the subject as having a poor prognosis in the absence of an ROR1-specific treatment.

In certain other aspects, a method of treatment is provided, comprising administering to a subject having a disease or condition an anti-ROR1 therapy, wherein a tissue or sample of the disease or condition in subject has been identified as having uniform or homogeneous expression of surface-expressed ROR1. In some embodiments, the determination has been carried out by a method disclosed above.

In another aspect, the present disclosure provides a kit, the kit comprising a binding protein or immunoglobulin-like binding protein, or composition, as disclosed herein.

BRIEF DESCRIPTION OF THE DRAWINGS

FIG. 5 shows the location of peptides in the C-terminal portion of ROR1 (amino acids 404-937) that were used for immunization of mice. The C-terminal amino acid sequences depicted in FIG. 5 (for human, SEQ ID NO.:51, and mouse, SEQ ID NO.:53, respectively) are present only in full-length ROR1 (ROR1_v1) (e.g., a full-length ROR1 corresponding to SEQ ID NO.:1 for human, or SEQ ID NO.:52 for mouse). The locations and sequences of the peptides used to immunize mice for human ROR1 antibody production are indicated by boxes (corresponding to SEQ ID NOS.:2, 3, 54, and 55).

FIGS. 23A through 23D illustrate similarity between human and rhesus ROR1 and show binding of mAb 6D4 to rhesus ROR1. (A) Alignment of the human (SEQ ID NO.:3), mouse (SEQ ID NO.:57), and rhesus (SEQ ID NO.:59) ROR1 sequence recognized by mAb 6D4. (B) Binding of antibody 6D4 against rhesus ROR1. Antibody 6D4 was tested against (A) K562 (ROR1−) cells and (B) K562 cells expressing rhesus ROR1 by IHC. Antibody 6D4 was also tested against (C) rhesus T cells (ROR1−) and (D) rhesus T cells transfected with rhesus ROR1. Antibody 6D4 exhibited clear cell-surface staining of full-length rhesus ROR1 when overexpressed in either K562 cells or rhesus T cells. (C) ROR1 staining in rhesus parathyroid and pancreatic islets. Regions in squares in middle panels are magnified 10× in right panels. (D) Representative IHC images of ROR1 staining in different regions of the macaque gastrointestinal tract. Regions in squares in middle panels are magnified 10× in right panels. Scale bar represents 100 µm.

DETAILED DESCRIPTION

Figure 1:
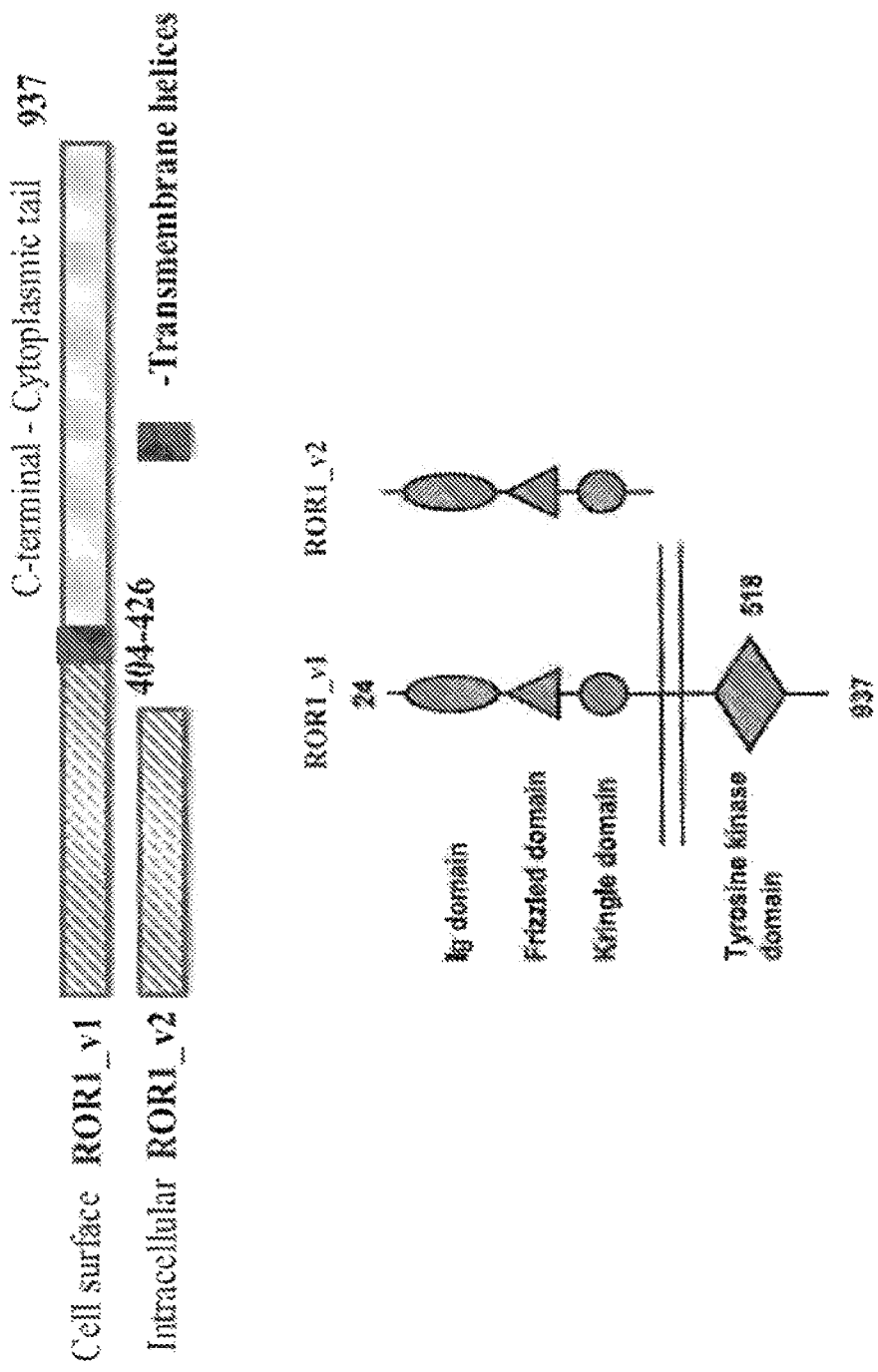
FIG. 1 shows a schematic of ROR1 splice variants. Ror1 is expressed as two splice variants as follows: a full-length 937 amino acid isoform of ROR1 that localizes to the cell surface (referred to herein as "ROR1_v1"); and a truncated 393 amino acid splice isoform that only includes the extracellular N-terminal portion of ROR1_v1 (i.e., lacks the transmembrane domain and intracellular C-terminal portion containing the tyrosine kinase domain) and, therefore, did not localize to the cell membrane (referred to herein as "ROR1_v2").

The present disclosure provides binding proteins, such as immunoglobulin-like binding proteins, e.g., antibodies (including antigen-binding fragments thereof) that are specific to, e.g., that specifically bind to, ROR1 or epitopes thereof or ROR-1 derived peptides, such as surface-expressed, endogenous, and/or full-length ROR1. Also provided are nucleic acids encoding those binding proteins, host cells expressing those binding proteins, and methods for using the same. The binding proteins provided herein in some aspects specifically bind to a C-terminal portion of ROR1 and, thus, can be used to detect expression of the full-length isoform of ROR1, which is found located on a cell surface, and in some embodiments, without binding to the truncated ROR1 isoform that lacks its C-terminal portion, which generally is localized intracellularly. Additionally, the immunoglobulin-like binding proteins in some aspects can be used to detect expression of full-length ROR1 in, for example, formalin-fixed-paraffin-embedded (FFPE) cells or tissues and, therefore, are useful as a diagnostic tool or as a companion diagnostic with an ROR1 therapeutic agent or regimen. For example, immunoglobulin-like binding proteins provided herein can be used to determine whether a subject would benefit from a ROR1-specific therapy, whether such therapy should be administered, continued, or adjusted, and/or whether a particular tumor type should be so-treated. Examples of therapies for use in any of the provided embodiments are immunotherapies, such as an antibody therapy and/or adoptive immunotherapy, and/or those comprising ROR1-specific chimeric antigen receptor (CAR)-modified cells, e.g., T cells.

Also provided are therapeutic methods, such as those involving administration of ROR1-specific therapies, such as immunotherapies. In certain embodiments, the therapy is or comprises an anti-ROR1 antibody or fragment thereof, such as a CAR comprising such an antibody fragment. In further embodiments, the therapy is or includes a CAR-modified cell in which the CAR specifically binds to a ROR1, such as an extracellular portion of a human ROR1. In some embodiments, the CAR binds to the ROR1 via a binding domain comprising an antibody fragment, such as an scFv. In some aspects, the CAR further comprises a spacer, such as one or more antibody constant regions and/or a hinge region; in some aspects, it further comprises a transmembrane domain and one or more, generally more than one, intracellular signaling domains, such as a CD3zeta-derived or other primary signaling domain and/or a costimulatory signaling domain, such as one derived from CD28 and/or 41BB.

In some embodiments, a CAR and/or antibody is, comprises, or shares epitope-specificity and/or competes for binding with the anti-ROR1 IgG1 antibody designated R12 (which is disclosed, e.g., Yang et al., *PloS ONE*, 6:e21018, 2011; Hudecek et al., *Clin. Cancer Res*, 19:3153, 2013; U.S. Patent Application No. US 2013/0251642), and/or an antigen-binding portion thereof, such as an scFv, and/or an antibody containing the CDRs thereof. A chimeric antigen receptor (CAR) containing an antigen-binding scFv fragment of R12 has been demonstrated to effectively promote antitumor reactivity in a CAR therapy (Hudecek et al., 2013; International PCT Publication No. WO 2014/031687).

In some embodiments, the disease or condition is or includes a tumor, which may be primary or metastatic. In some aspects, it is a hematologic tumor, which is optionally CLL or MCL, and/or is a solid tumor, which optionally is a breast cancer, lung cancer, ovarian cancer, or pancreatic cancer tumor, which optionally is a lung adenocarcinoma, adenocarcinoma, squamous cell carcinoma, small cell carcinoma, atypical carcinoid, or triple-negative breast cancer. In some aspects, at least 50%, at least 60%, at least 70%, at least 80%, or at least 90% of cells in the disease or condition, or of a tissue associated therewith, express ROR1 or an epitope or peptide thereof recognized by the therapy and/or such protein or epitope or peptide is uniformly or homogenously expressed therein. In some aspects, such expression has been determined using the provided antibodies and/or detection methods used therewith.

Prior to setting forth this disclosure in more detail, it may be helpful to an understanding thereof to provide definitions of certain terms used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated.

As used herein, the term "about" means ±20% of the indicated range, value, or structure, unless otherwise indicated.

It should be understood that the terms "a" and "an" as used herein refer to "one or more" of the enumerated components. The use of the alternative (e.g., "or") should be understood to mean either one, both, or any combination thereof of the alternatives.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

As used herein, the terms "include," "have," and "comprise" are used synonymously, which terms and variants thereof are intended to be construed as non-limiting.

The term "consisting essentially of" limits the scope of a claim to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, "ROR1" or "receptor tyrosine kinase-like orphan receptor 1" is a mammalian receptor tyrosine kinase polypeptide having homology to the human reference amino acid sequence of any one of UniProtKB Nos. Q01973-1, Q01973-2, or Q01973-3, or a consensus sequence of the reference amino acid sequences, or an isoform or variant or fragment thereof. An exemplary homolog is the mouse amino acid sequence of UniProtKB No. Q9Z139-1. In its full-length form, ROR1 comprises (1) an extracellular portion that contains an immunoglobulin-like domain, a Frizzled domain, and a Kringle domain; (2) a transmembrane portion; and (3) an intracellular portion containing a tyrosine kinase domain (FIG. 1), referred to herein as "full-length ROR1" or "ROR1_v1." In certain embodiments, full-length ROR1 is human full-length ROR1, e.g., comprising the amino acid sequence as set forth in SEQ ID NO.:1. ROR1 can also be found as an intracellular isoform comprising the N-terminal portion of the full-length ROR1, and lacking the transmembrane and intracellular portions of the full-length ROR1 (Hudecek et al., *Blood* 116:4532, 2010), referred to herein as "truncated ROR1" or "short isoform ROR1" or "ROR1 v2."

The term "polypeptide" as used herein refers to a compound made up of amino acid residues that are linked by peptide bonds. The term "protein" may be synonymous with the term "polypeptide" or may refer, in addition, to a complex of two or more polypeptides. A polypeptide may further contain other components (e.g., covalently bound), such as a tag, a label, a bioactive molecule, or any combination thereof. In certain embodiments, a polypeptide may be a fragment. As used herein, a "fragment" means a polypeptide that is lacking one or more amino acids that are found in a reference sequence. A fragment can comprise a binding domain, antigen, or epitope found in a reference sequence. A fragment of a reference polypeptide can have at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more of amino acids of the amino acid sequence of the reference sequence.

As described herein, a "variant" polypeptide species has one or more non-natural amino acids, one or more amino acid substitutions, one or more amino acid insertions, one or more amino acid deletions, or any combination thereof at one or more sites relative to a reference polypeptide as presented herein. In certain embodiments, "variant" means a polypeptide having a substantially similar activity (e.g., enzymatic function, immunogenicity) or structure relative to a reference polypeptide). A variant of a reference polypeptide can have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity to the amino acid sequence for the reference polypeptide as determined by sequence alignment programs and parameters known in the art. The variant can result from, for example, a genetic polymorphism or human manipulation. Conservative substitutions of amino acids are well known and may occur naturally or may be introduced when a protein is recombinantly produced. Amino acid substitutions, deletions, and additions may be introduced into a protein using mutagenesis methods known in the art (see, e.g., Sambrook et al., *Molecular Cloning: A Laboratory Manual*, 3d ed., Cold Spring Harbor Laboratory Press, NY, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare polypeptide variants (see, e.g., Sambrook et al., supra).

The terms "identical" or "percent identity," in the context of two or more polypeptide or nucleic acid molecule sequences, means two or more sequences or subsequences that are the same or have a specified percentage of amino acid residues or nucleotides that are the same over a specified region (e.g., 60%, 65%, 70%, 75%, 80%, 85%, 90%, 91%, 92%, 93%, 94%, 95%, 96%, 97%, 98%, 99%, or 100% identity), when compared and aligned for maximum correspondence over a comparison window, or designated region, as measured using methods known in the art, such as a sequence comparison algorithm, by manual alignment, or by visual inspection. For example, preferred algorithms suitable for determining percent sequence identity and sequence similarity are the BLAST and BLAST 2.0 algorithms, which are described in Altschul et al. (*Nucleic Acids Res.* 25: 3389, 1977) and Altschul et al. (*J. Mol. Biol.* 215: 403, 1990) respectively.

As used herein, a "fusion protein" comprises a single chain polypeptide having at least two distinct domains, wherein the domains are not naturally found together in a protein. A nucleic acid molecule encoding a fusion protein may be constructed using PCR, recombinantly engineered, or the like, or such fusion proteins can be made synthetically. A fusion protein may further contain other components (e.g., covalently bound), such as a tag or bioactive molecule.

A "nucleic acid molecule" or "polynucleotide" refers to a single- or double-stranded linear or circular polynucleotide containing either deoxyribonucleotides or ribonucleotides that are linked by 3'-5'-phosphodiester bonds. A nucleic acid molecule includes RNA, DNA, genomic DNA, mitochondrial DNA, cDNA, or vector DNA.

Variants of the polynucleotides of this disclosure are also contemplated. Variant polynucleotides are at least 80%, 85%, 90%, 95%, 99%, or 99.9% identical to a reference polynucleotide as described herein, or that hybridizes to a reference polynucleotide of defined sequence under stringent hybridization conditions of 0.015M sodium chloride, 0.0015M sodium citrate at about 65°-68° C. or 0.015M sodium chloride, 0.0015M sodium citrate, and 50% formamide at about 42° C. The polynucleotide variants retain the capacity to encode an immunoglobulin-like binding protein or antigen-binding fragment thereof having the functionality described herein.

The term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the co-existing materials in the natural system, is isolated. Such polynucleotide could be part of a vector and/or such polynucleotide or polypeptide could be part of a composition (e.g., a cell lysate), and still be isolated in that such vector or composition is not part of the natural environment for the nucleic acid or polypeptide.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

As used herein, "heterologous" or "exogenous" nucleic acid molecule, construct or sequence refers to a nucleic acid molecule or portion of a nucleic acid molecule that is not native to a host cell, but may be homologous to a nucleic acid molecule or portion of a nucleic acid molecule from the host cell. The source of the heterologous or exogenous nucleic acid molecule, construct or sequence may be from a different genus or species. In certain embodiments, a heterologous or exogenous nucleic acid molecule is added (i.e., not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, "heterologous" refers to a non-native enzyme, protein, or other activity encoded by an exogenous nucleic acid molecule introduced into the host cell, even if the host cell encodes a homologous protein or activity.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

"Immunohistochemistry" (IHC) means a technique used to detect the presence of an antigen in histology samples, such as cells and tissue samples, using an antibody specific to the antigen. The cells or tissue samples may be any tissue or cell obtained from a subject or a biological source. A "subject" or "biological source" may be, for example, a human or non-human animal, a primary cell, cell culture or culture adapted cell line, including genetically engineered cell lines that may contain chromosomally integrated or episomal recombinant or heterologous nucleic acid molecules, somatic cell hybrid cell lines, immortalized or immortalizable cells or cell lines, differentiated or differentiatable cells or cell lines, transformed cells or cell lines, or the like. In certain embodiments, a biological sample is from a human. "Human patient" is intended mean a human subject who is afflicted with, or at risk of developing or relapsing with, any disease or condition associated with expression or overexpression of ROR1, such as full-length ROR1.

"Immunoblot" or "immunoblotting" (also referred to as Western blot) means a technique used to detect the presence of an antigen (e.g., ROR1) in a sample of tissue homogenate or extract, using gel electrophoresis to separate proteins and staining the separated proteins with antibodies, or fragment or variants thereof, specific for the antigen.

Binding Proteins Specific For ROR1

Provided are binding proteins, such as ROR1 binding proteins, which generally specifically bind to ROR1 protein and/or a portion thereof. The binding proteins include binding domains and binding proteins disclosed herein in some embodiments specifically detect full-length ROR1 since they bind to a C-terminal portion of ROR1, which is present in the full-length ROR1 isoform and absent in the truncated ROR1 isoform. In contrast, most commercially available and published anti-ROR1 antibodies are directed against the N-terminal portion of ROR1, which is present in both the full-length ROR1 (ROR1_v1) and the truncated ROR1 (ROR1_v2) forms. Accordingly, the immunoglobulin binding domains and immunoglobulin-like proteins of this disclosure can be used to identify cells and tissues that express (e.g., endogenous) full-length ROR1 with a high degree of specificity.

Moreover, the immunoglobulin binding domains and proteins of this disclosure are capable of detecting full-length ROR1 endogenously expressed by, for example, cancer cells. In addition, immunoglobulin-like binding proteins disclosed herein are useful for detecting endogenous expression of full-length ROR1 in histology samples, such as in formalin-fixed paraffin-embedded (FFPE) tissue samples. By comparison, commercially available and published anti-ROR1 antibodies inconsistently bind, weakly detect, or generally fail to detect endogenously expressed ROR1 in histology samples. For example, such commercial antibodies do not detect endogenous ROR1 expression in histological samples that have been fixed in formalin and embedded in paraffin. Hence, the immunoglobulin binding domains and proteins disclosed herein also exhibit greater sensitivity (in addition to greater specificity) to detecting endogenously expressed ROR1 as compared to known anti-ROR1 antibodies.

A "binding domain" or "binding region," as used herein, refers to a protein, polypeptide, oligopeptide, or peptide (e.g., antibody, receptor) or portion thereof that possesses the ability to specifically recognize and bind to a target (e.g., antigen, ligand). A binding domain includes any naturally occurring, synthetic, semi-synthetic, or recombinantly produced binding partner for a biological molecule or another target of interest. Exemplary binding domains include immunoglobulin light and heavy chain variable regions (e.g., domain antibodies, sFv, single chain Fv fragment (scFv), Fab, F(ab')$_2$), receptor ectodomains, or ligands. Immunoglobulin variable domains (e.g., scFv, Fab) are referred to herein as "immunoglobulin binding domains." A variety of assays are known for identifying binding domains of the present disclosure that specifically bind a particular target, including Western blot, ELISA, and Biacore® analysis.

In certain embodiments, a binding domain is part of a larger polypeptide or protein and is referred to as a "binding protein." An "immunoglobulin binding protein" or "immunoglobulin-like binding protein" refers to a polypeptide containing one or more immunoglobulin binding domains, wherein the polypeptide may be in the form of any of a variety of immunoglobulin-related protein scaffolds or structures, such as an antibody or an antigen binding fragment thereof, a scFv-Fc fusion protein, or a fusion protein comprising two or more of such immunoglobulin binding domains or other binding domains.

A binding domain or protein that binds "C-terminal" to a specified domain refers to the binding domain or protein binding to an epitope located within the specified domain or closer to the C terminus of the protein relative to the specified domain. For example, binding "C-terminal to an intracellular protein kinase domain of ROR1" refers to binding to a portion of ROR1 located within the intracellular protein kinase domain, located adjacent to (next to or within about 10 to about 15 amino acids) and closer to the C-terminus of ROR1 relative to the intracellular protein kinase domain, or located between the C-terminus and the intracellular protein kinase domain of ROR1.

In certain aspects, the present disclosure provides a binding protein that specifically binds a C-terminal portion of ROR1. In some embodiments, a binding protein specifically binds C-terminal to an intracellular protein kinase domain of ROR1. In particular embodiments, a binding protein is an immunoglobulin-like binding protein. In further embodiments, a binding protein is or comprises an antibody or antigen binding fragment thereof. In any of the aforementioned embodiments, the ROR1 may be a human ROR1. For example, in some embodiments, the antibody or antigen binding fragment thereof is a monoclonal antibody or an antigen binding fragment thereof, such as 6D4 or antigen binding fragment thereof, such as one comprising a sequence set forth as SEQ ID NO: 37 and/or 38, or an antibody comprising one or more CDRs thereof or that competes with such an antibody for binding to a ROR1 or a ROR1 peptide.

The term "epitope" includes any amino acid sequence or protein determinant capable of specific binding to an immunoglobulin, receptor, or other binding domain or binding protein. Epitopic determinants generally contain chemically active surface groupings of molecules, such as amino acids or sugar side chains, and can have specific three dimensional structural characteristics, as well as specific charge characteristics.

In certain embodiments, an immunoglobulin-like binding protein of this disclosure can specifically bind to an epitope located within the amino acid sequence that is at least 90%, at least 91%, at least 92%, at least 93%, at least 94%, at least 95%, at least 96%, at least 97%, at least 98%, at least 99%, at least 99.5%, or 100% identical to the amino acid sequence set forth in SEQ ID NO.:2, 3, 4, 5, 54, or 55. In further embodiments, an immunoglobulin-like binding protein of this disclosure can specifically bind to an epitope located within the amino acid sequence that is at least 90%, at least 91%, at least 92%, at least 93%, at least 94%, at least 95%, at least 96%, at least 97%, at least 98%, at least 99%, at least 99.5%, or 100% identical to the amino acid sequence set forth in SEQ ID NO.:2, 3, 54, or 55. In further embodiments, an immunoglobulin-like binding protein of this disclosure specifically binds to an epitope located within the amino acid sequence of N-NPRYPNYMFPSQGITPQGQIAGFIGPPIP-C (SEQ ID NO.:3).

In certain embodiments, a binding protein of this disclosure specifically binds to (i) a peptide comprising SEQ ID NO.:3, wherein the peptide optionally consists of SEQ ID NO.:3, and/or (ii) an epitope of a ROR1 protein, which epitope (a) is within the amino acid sequence set forth in SEQ ID NO.:3 and/or (b) comprises one or more amino acids within the amino acid sequence set forth in SEQ ID NO.:3.

In specific embodiments, a binding protein of this disclosure binds an epitope located within an amino acid sequence at least 90% identical to an amino acid sequence set forth in SEQ ID NO.:3.

Sources of binding domains include antibody variable regions from various species (which can be formatted as antibodies, sFvs, scFvs, Fabs, or soluble $V_H$ domain or domain antibodies), including human, rodent, avian, leporine, and ovine. Additional sources of binding domains include variable regions of antibodies from other species, such as camelid (from camels, dromedaries, or llamas; Ghahroudi et al., *FEBS Letters* 414: 521, 1997; Vincke et al., *J. Biol. Chem.* 284: 3273, 2009; Hamers-Casterman et al., *Nature* 363: 446, 1993 and Nguyen et al., *J. Mol. Biol.* 275: 413, 1998), nurse sharks (Roux et al., *Proc. Nat'l. Acad. Sci. (USA)* 95: 11804, 1998), spotted ratfish (Nguyen et al., *Immunogenetics* 54: 39, 2002), or lamprey (Herrin et al., *Proc. Nat'l. Acad. Sci. (USA)* 105: 2040,2008 and Alder et al., *Nature Immunol.* 9: 319, 2008). These antibodies can apparently form antigen-binding regions using only heavy chain variable region, i.e., these functional antibodies are homodimers of heavy chains only (referred to as "heavy chain antibodies") (Jespers et al., *Nature Biotechnol.* 22: 1161, 2004; Cortez-Retamozo et al., *Cancer Res.* 64: 2853, 2004; Baral et al., *Nature Med.* 12: 580, 2006; and Barthelemy et al., *J. Biol. Chem.* 283: 3639, 2008).

Terms understood by those in the art of antibody technology are each given the meaning acquired in the art, unless expressly defined differently herein. The term "antibody" refers to an intact antibody comprising at least two heavy (H) chains and two light (L) chains inter-connected by disulfide bonds, as well as any antigen-binding portion or fragment of an intact antibody that has or retains the ability to bind to the antigen target molecule recognized by the intact antibody, such as an scFv, Fab, or Fab'2 fragment. Thus, the term "antibody" herein is used in the broadest sense and includes polyclonal and monoclonal antibodies, including intact antibodies and functional (antigen-binding) antibody fragments thereof, including fragment antigen binding (Fab) fragments, F(ab')$_2$ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

A monoclonal antibody or antigen-binding portion thereof may be non-human, chimeric, humanized, or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988).

For example, the terms "$V_L$" and "$V_H$" refer to the variable binding region from an antibody light and heavy chain, respectively. The variable binding regions are made up of discrete, well-defined sub-regions known as "complementarity determining regions" (CDRs) and "framework regions" (FRs). The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 of the heavy chain linked to the light chain via an inter-chain disulfide bond.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al., "Sequences of Proteins of Immunological Interest," (5th Ed. Public Health Service, National Institutes of Health, Bethesda, MD, 1991) ("Kabat" numbering scheme), Al-Lazikani et al. (J. Mol. Biol. 273:927-948, 1997) ("Chothia" numbering scheme), MacCallum et al. (J. Mol. Biol. 262: 732-745, 1996) ("Contact" numbering scheme), Lefranc M P et al. (Dev. Comp. Immunol. 7:55-77, 2003) ("IMGT" numbering scheme), and Honegger A and Plückthun A (J. Mol. Biol. 309:657-70, 2001) ("Aho" numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table 1, below, lists exemplary position boundaries of CDR-L1, CDR-L2, CDR-L3 and CDR-H1, CDR-H2, CDR-H3 as identified by Kabat, Chothia, and Contact schemes, respectively. For CDR-H1, residue numbering is listed using both the Kabat and Chothia numbering schemes. FRs are located between CDRs, for example, with FR-L1 located between CDR-L1 and CDR-L2, and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

Exemplary CDR Position Boundaries

| CDR | Kabat | Chothia | Contact |
|---|---|---|---|
| CDR-L1 | L24 - - - L34 | L24 - - - L34 | L30 - - - L36 |
| CDR-L2 | L50 - - - L56 | L50 - - - L56 | L46 - - - L55 |
| CDR-L3 | L89 - - - L97 | L89 - - - L97 | L89 - - - L96 |
| CDR-H1 (Kabat Numbering[1]) | H31 - - - H35B | H26 - - - H32 . . . 34 | H30 - - - H35B |
| CDR-H1 (Chothia Numbering[2]) | H31 - - - H35 | H26 - - - H32 | H30 - - - H35 |
| CDR-H2 | H50 - - - H65 | H52 - - - H56 | H47 - - - H58 |
| CDR-H3 | H95 - - - H102 | H95 - - - H102 | H93 - - - H101 |

[1]Kabat et al., "Sequences of Proteins of Immunological Interest," 5th Ed. Public Health Service, National Institutes of Health, Bethesda, MD, 1991.
[2]Al-Lazikani et al., J. Mol. Biol. 273: 927-948, 1997.

Thus, unless otherwise specified, a "CDR" or "complementary determining region," or individual specified CDRs (e.g., CDR-H1, CDR-H2), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given $V_H$ or $V_L$ amino acid sequence, it is understood that such a CDR has a sequence of the corresponding CDR (e.g., CDR-H3) within the variable region, as defined by any of the aforementioned schemes. In some embodiments, specified CDR sequences are specified. Likewise, unless otherwise specified, a FR or individual specified FR(s) (e.g., FR-H1, FR-H2), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, or Contact method. In other cases, the particular amino acid sequence of a CDR or FR is given.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. In particular embodiments, antibodies are single-chain antibody fragments comprising a variable heavy chain region, a variable light chain region or both, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, such as, for example, proteolytic digestion of an intact antibody and production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

As used herein, "Fc region portion" refers to the heavy chain constant region segment of the Fc fragment (the "fragment crystallizable" region or Fc region) from an antibody, which can in include one or more constant domains, such as CH2, CH3, CH4, or any combination thereof. In certain embodiments, an Fc region portion includes the CH2 and CH3 domains of an IgG, IgA, or IgD antibody or any combination thereof, or the CH3 and CH4 domains of an IgM or IgE antibody and any combination thereof. In other embodiments, a CH2CH3 or a CH3CH4 structure has sub-region domains from the same antibody isotype and are human, such as human IgG1, IgG2, IgG3, IgG4, IgA1, IgA2, IgD, IgE, or IgM (e.g., CH2CH3 from human IgG1). By way of background, an Fc region is responsible for the effector functions of an immunoglobulin, such as ADCC (antibody-dependent cell-mediated cytotoxicity), CDC (complement-dependent cytotoxicity) and complement fixation, binding to Fc receptors (e.g., CD16, CD32, FcRn), greater half-life in vivo relative to a polypeptide lacking an Fc region, protein A binding, and perhaps even placental transfer (see Capon et al., Nature 337: 525, 1989). In certain embodiments, an Fc region portion found in immunoglobulin-like binding proteins of the present disclosure will be capable of mediating one or more of these effector functions, or will lack one or more or all of these activities by way of, for example, one or more mutations known in the art.

In addition, antibodies have a hinge sequence that is typically situated between the Fab and Fc region (but a lower section of the hinge may include an amino-terminal portion of the Fc region). By way of background, an immunoglobulin hinge acts as a flexible spacer to allow the Fab portion to move freely in space. In contrast to the constant regions, hinges are structurally diverse, varying in both sequence and length between immunoglobulin classes and even among subclasses. For example, a human IgG1 hinge region is freely flexible, which allows the Fab fragments to rotate about their axes of symmetry and move within a sphere centered at the first of two inter-heavy chain disulfide bridges. By comparison, a human IgG2 hinge is relatively short and contains a rigid poly-proline double helix stabilized by four inter-heavy chain disulfide bridges, which restricts the flexibility. A human IgG3 hinge differs from the other subclasses by its unique extended hinge region (about four times as long as the IgG1 hinge), containing 62 amino acids (including 21 prolines and 11 cysteines), forming an inflexible poly-proline double helix and providing greater flexibility because the Fab fragments are relatively far away from the Fc fragment. A human IgG4 hinge is shorter than IgG1 but has the same length as IgG2, and its flexibility is intermediate between that of IgG1 and IgG2.

As used herein, unless otherwise provided, a position of an amino acid residue in the constant region of human IgG1 heavy chain is numbered assuming that the variable region of human IgG1 is composed of 128 amino acid residues according to the Kabat numbering convention. The numbered constant region of human IgG1 heavy chain is then used as a reference for numbering amino acid residues in constant regions of other immunoglobulin heavy chains. A position of an amino acid residue of interest in a constant region of an immunoglobulin heavy chain other than human IgG1 heavy chain is the position of the amino acid residue in human IgG1 heavy chain with which the amino acid residue of interest aligns. Alignments between constant regions of human IgG1 heavy chain and other immunoglobulin heavy chains may be performed using software programs known in the art, such as the Megalign program (DNASTAR Inc.) using the Clustal W method with default parameters. According to the numbering system described herein, for example, although human IgG2 $C_{H2}$ region may have an amino acid deletion near its amino-terminus compared with other $C_{H2}$ regions, the position of the "N" located at 296 in human IgG2 $C_{H2}$ is still considered position 297 because this residue aligns with "N" at position 297 in human IgG1 $C_{H2}$.

In some embodiments, an immunoglobulin-like binding protein is an antibody or an antigen-binding fragment thereof. For example, a binding protein comprises an antibody, and the antibody is a monoclonal antibody or an antigen-binding fragment thereof. In certain embodiments, an immunoglobulin-like binding protein is monoclonal antibody 6D4 or an antigen-binding fragment thereof.

In certain embodiments, a binding protein of this disclosure, e.g., an antibody or a binding fragment thereof, contains a heavy chain or portion thereof comprising sequences set forth SEQ ID NOS.:6, 7, and 8. In some embodiments, a heavy chain or portion thereof comprises amino acid sequences (e.g., CDR sequences) set forth as SEQ ID NOS.:21, 25, and 29; and/or 22, 26 and 29; and/or 23, 27, and 29; and/or 24, 28, and 30. In some embodiments, a heavy chain or portion thereof comprises SEQ ID NO.:37 or a sequence having at least 90, 95, 96, 97, 98, or 99% identity thereto, and/or comprises at least 90, 95, 96, 97, 98, or 99% identity or 100% identity to a sequence set forth as SEQ ID NO.:12, 13 or 14. In some embodiments, the antibody comprises the sequence of SEQ ID NO.:8, 29 or 30 and the sequence of SEQ ID NO.:11, 35 or 36. In certain embodiments, the binding protein, e.g., antibody or fragment thereof, contains a light chain or portion thereof comprising the sequences set forth as SEQ ID NO.:9, 10, and 11. In some embodiments, the light chain or portion thereof comprises amino acid sequences (e.g., CDR sequences) set forth as SEQ ID NOS.:31, 33 and 35; and/or 32, 34 and 36. In some embodiments, the light chain or portion thereof comprises SEQ ID NO.:38 or a sequence having at least 90, 95, 96, 97, 98, or 99% identity thereto, and/or comprises at least 90, 95, 96, 97, 98, or 99% identity or 100% identity to a sequence set forth as SEQ ID NO.:15 or 16. In some embodiments the heavy chain or portion thereof is or comprises a $V_H$ and in some embodiments the light chain or portion thereof is or comprises a $V_L$.

In certain embodiments, a binding protein comprises (a) a heavy chain CDR1 amino acid sequence as set forth in SEQ ID NO.:6, or a variant of SEQ ID NO.:6 having 1 or 2 amino acid substitutions; (b) a heavy chain CDR2 amino acid sequence shown in SEQ ID NO.:7, or a variant of SEQ ID NO.:7 having 1 or 2 amino acid substitutions; and (c) a heavy chain CDR3 amino acid sequence shown in SEQ ID NO.:8, or a variant of SEQ ID NO.:8 having 1 or 2 amino acid substitutions. In other embodiments, an immunoglobulin-like binding protein of this disclosure comprises (a) a light chain CDR1 amino acid sequence shown in SEQ ID NO.:9, or a variant of SEQ ID NO.:9 having 1 or 2 amino acid substitutions; (b) a light chain CDR2 amino acid sequence shown in SEQ ID NO.:10, or a variant of SEQ ID NO.:10 having 1 or 2 amino acid substitutions; and (c) a light chain CDR3 amino acid sequence shown in SEQ ID NO.:11, or a variant of SEQ ID NO.:11 having 1 or 2 amino acid substitutions. In further embodiments, an immunoglobulin-like binding protein of this disclosure, such as an antibody or antigen binding fragment thereof, comprises a light chain variable domain ($V_L$) that is at least 90% identical to an amino acid sequence as set forth in SEQ ID NO.:15 or 16, and a heavy chain variable domain ($V_H$) that is at least 90% identical to an amino acid sequence as set forth in SEQ ID NO.:12, 13, or 14. In any of the aforementioned embodiments, an immunoglobulin-like binding protein is an antibody or antigen binding fragment thereof, such as a monoclonal antibody or an engineered monoclonal antibody or binding fragments thereof.

In certain embodiments, a binding protein disclosed herein comprises (i) a heavy chain CDR3, having the amino acid sequence of a CDR3 within the heavy chain variable domain ($V_H$) sequence set forth in SEQ ID NO.:12, 13, or 14; and/or (ii) a light chain CDR3, having the amino acid sequence of a CDR3 within the light chain variable domain ($V_L$) sequence set forth in SEQ ID NO.:15 or 16. In further embodiments, the heavy chain CDR3 comprises the sequence set forth as SEQ ID NO.:29 or SEQ ID NO.:30 and/or the light chain CDR3 comprises the sequence set forth as SEQ ID NO.:35 or SEQ ID NO.:36. In such embodiments, the binding protein may further comprise a heavy chain CDR1 and/or a heavy chain CDR2 having the amino acid sequences of a CDR1 and/or a CDR2, respectively, within the heavy chain variable domain ($V_H$) sequence set forth in SEQ ID NO.:12, 13, or 14; and/or (ii)

a light chain CDR1 and/or a light chain CDR2, respectively, having the amino acid sequence of a CDR3 within the light chain variable domain ($V_L$) sequence set forth in SEQ ID NO.:15 or 16. In particular embodiments, the heavy chain CDR1 comprises the sequence set forth as SEQ ID NO.:21, 22, 23, or 24, and/or the heavy chain CDR2 comprises the sequence set forth as SEQ ID NO.:25, 26, 27, or 28; and/or the light chain CDR1 comprises the sequence set forth as SEQ ID NO.:31 or 32 and the light chain CDR2 comprises the sequence set forth as SEQ ID NO.:33 or 34.

In certain embodiments, a binding protein of the disclosure comprises a light chain variable domain ($V_L$) that is at least 90% identical to an amino acid sequence as set forth in SEQ ID NO.:15 or 16, and a heavy chain variable domain ($V_H$) that is at least 90% identical to an amino acid sequence as set forth in SEQ ID NO.:12, 13, or 14; and/or wherein the binding protein comprises a $V_H$ comprising SEQ ID NO.:37 and/or a $V_L$ comprising SEQ ID NO.:38.

In certain other embodiments, a binding protein comprises an antigen binding fragment of an antibody, such as an scFv (a heavy chain variable domain ($V_H$) and a light chain variable domain ($V_L$), connected by a short peptide linker). For example, an immunoglobulin-like binding protein of this disclosure comprises an scFv having a light chain variable domain ($V_L$) that is at least 90% identical to an amino acid sequence as set forth in SEQ ID NO.:15 or 16, or comprises a sequence of SEQ ID NO.:38, and a heavy chain variable domain ($V_H$) that is at least 90% identical to an amino acid sequence as set forth in SEQ ID NO.:12, 13, or 14, or comprises a sequence of SEQ ID NO:37, or a sequence having at least 95, 96, 97, 98, or 99% identity therewith. In certain embodiments, an scFv comprises a $V_H$ having an amino acid sequence as set forth in SEQ ID NO.:12, 13 or 14, or comprises a sequence of SEQ ID NO:37, or a sequence having at least 95, 96, 97, 98, or 99% identity therewith, and a $V_L$ having an amino acid sequence as set forth in SEQ ID NO.:15 or 16, or comprises a sequence of SEQ ID NO.:38, or a sequence having at least 95, 96, 97, 98, or 99% identity therewith. In particular embodiments, a binding protein of this disclosure comprises an scFv having variable domains $V_L$ and $V_H$ of monoclonal antibody 6D4 or a binding fragment thereof.

In still further embodiments, a binding protein of this disclosure comprises an antibody or fragment thereof comprising a light chain variable domain ($V_L$) that is at least 90% identical to an amino acid sequence as set forth in SEQ ID NO.:15 or 16, and a heavy chain variable domain ($V_H$) that is at least 90% identical to an amino acid sequence as set forth in SEQ ID NO.:12, 13, or 14, wherein the antibody optionally specifically binds to (i) a peptide comprising SEQ ID NO.:3, wherein the peptide optionally consists of SEQ ID NO.:3, and/or (ii) an epitope of a ROR1 protein, which epitope (a) is within the amino acid sequence set forth in SEQ ID NO.:3 and/or (b) comprises one or more amino acids within the amino acid sequence set forth in SEQ ID NO.:3.

In still further embodiments, a binding protein of the present disclosure does not bind ROR2.

As used herein, "specifically binds" or "specific for" may in some embodiments refer to an association or union of a binding protein (e.g., an anti-ROR1 antibody) or a binding domain (or fusion protein thereof) to a target molecule with an affinity or $K_a$ (i.e., an equilibrium association constant of a particular binding interaction with units of 1/M) equal to or greater than $10^5$ M$^{-1}$ (which equals the ratio of the on-rate [$k_{on}$] to the off-rate [$k_{off}$] for this association reaction), while not significantly associating or uniting with any other molecules or components in a sample. Binding domains (or fusion proteins thereof) may be classified as "high affinity" binding domains (or fusion proteins thereof) and "low affinity" binding domains (or fusion proteins thereof). "High affinity" binding domains refer to those binding domains with a $K_a$ of at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, or at least $10^{13}$ M$^{-1}$, preferably at least $10^8$ M$^{-1}$ or at least $10^9$ M$^{-1}$. "Low affinity" binding domains refer to those binding domains with a $K_a$ of up to $10^8$ M$^{-1}$, up to $10^7$ M$^{-1}$, up to $10^6$ M$^{-1}$, up to $10^5$ M$^{-1}$. Alternatively, affinity may be defined as an equilibrium dissociation constant ($K_d$) of a particular binding interaction with units of M (e.g., $10^{-5}$ M to $10^{-13}$ M).

A variety of assays are known for identifying binding domains of the present disclosure that specifically bind a particular target, as well as determining binding domain or fusion protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent).

In certain embodiments, any of the aforementioned binding proteins bind to ROR1, such as human ROR1, with high affinity. For example, an immunoglobulin-like binding protein having high affinity to human ROR1 binds with a $K_d$ of $1 \times 10^{-7}$ M or less.

In any of the aforementioned embodiments, a binding protein may bind to human ROR1, and in some aspects does not bind to or does not bind specifically to a ROR1 of another species, such as a murine ROR1 and/or does bind to a ROR1 of yet another species, such as rhesus macaque.

In still further embodiments, the present disclosure provides a binding protein (e.g., immunoglobulin-like binding protein, antibody or antigen-binding fragment thereof, or fusion binding protein) for that competes with a reference binding protein (e.g., immunoglobulin-like binding protein, antibody or antigen-binding fragment thereof, or fusion binding protein) for specific binding to an ROR1 epitope located C-terminal to an intracellular protein kinase domain of ROR1. The term "compete" when used in the context of immunoglobulin-like binding proteins or antibodies or binding fragments thereof that compete for the same epitope means competition between immunoglobulin-like binding proteins determined by an assay in which the immunoglobulin binding protein or antibody or binding fragment thereof being tested prevents or inhibits specific binding of a reference immunoglobulin-like binding protein or antibody or binding fragment thereof to the ROR1 epitope. For example, a test antibody that binds the same epitope or an overlapping epitope that is recognized by antibody 6D4 or a binding fragment thereof will be able to compete for binding to the target protein (ROR1) or fragment thereof containing the epitope. Competitive binding assays are known in the art, and include radioimmunoassays (RIA), competitive enzyme immunoassays (EIAs), and sandwich competition assays. In some embodiments, a binding protein of the present disclosure competes for binding to ROR1 and/or to a peptide of SEQ ID NO: 3, and/or binds to the same or an overlapping epitope of ROR1 with a reference protein as disclosed herein. In some embodiments, a reference binding protein comprises a heavy chain CDR1 amino acid sequence as set forth in SEQ ID NO.:6, a heavy chain CDR2 amino acid sequence as set forth in SEQ ID NO.:7, a heavy chain CDR3 amino acid sequence as set forth in SEQ ID NO.:8, a light chain CDR1 amino acid sequence as set forth in SEQ ID NO.:9, a light chain CDR2 amino acid sequence as set forth in SEQ ID NO.:10, and a light chain CDR3 amino acid sequence as set forth in SEQ ID NO.:11. In certain embodiments, an immunoglobulin-like binding protein competes with a reference immunoglobulin binding protein for specific binding to an ROR1 epitope located C-terminal to an intracellular protein kinase domain of ROR1, wherein the reference binding protein comprises a light chain variable domain ($V_L$) that is at least 90% identical to an amino acid sequence as set forth in SEQ ID NO.:15 or 16, and a heavy chain variable domain ($V_H$) that is at least 90% identical to an amino acid sequence as set forth in SEQ ID NO.:12, 13, or 14. In some embodiments, a reference binding protein comprises a light chain variable domain ($V_L$) that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:15, 16, or 38, and a heavy chain variable domain ($V_H$) that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:12, 13, 14, or 37. In particular embodiments, a reference binding protein comprises monoclonal antibody 6D4 or a binding fragment thereof.

In more embodiments, a binding protein, a reference binding protein or both is each individually an antibody or an antigen-binding fragment thereof. For example, a binding protein, a reference binding protein, or both may comprise an antibody, which may be a monoclonal antibody. In particular embodiments, for example, the reference binding protein is monoclonal antibody 6D4. In some embodiments, a binding protein, a reference binding protein, or both may each individually comprise a chimeric or humanized antibody. In still further embodiments, a binding protein, a reference binding protein, or both comprise an antigen-binding fragment of an antibody, and the antigen-binding fragment is an scFv. In still further embodiments, a binding protein, a reference binding protein, or both is a fusion protein comprising an antigen-binding domain (e.g., scFv from monoclonal antibody 6D4), wherein the antigen is ROR1, such as mammalian or human ROR1. In certain embodiments, an antigen-binding domain of the fusion protein is an antigen-binding fragment of an antibody. For example, a fusion protein may comprise an antigen-binding fragment of an antibody, wherein the antigen-binding fragment is an scFv specific for ROR1, such as mammalian or human ROR1.

In some embodiments, a binding protein or an immunoglobulin-like binding protein as disclosed herein further comprises a marker, such as an enzyme, a dye, a fluorescent label, a DNA barcode (e.g., ranging from five up to 75 nucleotides long), or a tag. As used herein, "peptide tag" or "protein tag" refers to a unique peptide sequence that is affixed to, fused to, or part of a protein of interest and is specifically bound by a heterologous or non-endogenous cognate binding molecule, which binding properties can be used to detect, identify, isolate or purify, track, enrich for, or target a tagged peptide or protein or cells expressing a tagged peptide or protein, particularly when a tagged peptide or protein is part of a heterogeneous population of proteins or other material, or when cells expressing a tagged peptide or protein are part of a heterogeneous population of cells (e.g., biological sample).

In certain embodiments, a marker comprises a fluorescent label, such as a cyanine dye, a coumarin, a rhodamine, a xanthene, a fluorescein, or sulfonated derivatives thereof, or a fluorescent protein. Alternately, a binding protein or an immunoglobulin-like binding protein can comprise a chromogenic reporter enzyme, such as horseradish peroxidase (HRP) or an alkaline phosphatase (AP). In other embodiments, a marker may be a tag molecule. In some embodiments, a marker may be a tag used for in vitro imaging. In further embodiments, a marker may be a tag used to isolate a binding protein or an immunoglobulin-like binding protein. In still further embodiments, a marker is a peptide tag or protein tag, such as, for example, a Myc tag, His tag, or Strep tag®.

In any of the aforementioned embodiments, the binding protein (a) may be capable of specifically binding to the protein, the ROR1 and/or an epitope that is endogenously present in a cell of a biological sample, which sample optionally comprises a formalin-fixed or frozen tissue section and/or permeablized cell and/or is optionally derived from a tumor of a subject. In some embodiments, the sample is derived from a tumor tissue, which is selected from the group consisting of hematologic malignancies and solid tumors. In particular embodiments, the sample is (a) derived from CLL or MCL or (b) is derived from an ovarian cancer, a lung cancer, which optionally is selected from among lung adenocarcinoma, adenocarcinoma, squamous cell carcinoma, small cell carcinoma, and atypical carcinoid, or a breast cancer, which optionally is a triple-negative breast cancer. In still other embodiments, the sample is derived from a normal tissue selected from the group consisting of bone marrow, adipose tissue, parathyroid, esophagus, and pancreas.

In any of the aforementioned embodiments, the binding protein optionally specifically binds to a full-length ROR1.

In any of the aforementioned embodiments, the binding protein may be capable of detecting endogenous expression of ROR1 under conditions under which a reference antibody does not detect said endogenous expression, which reference antibody is optionally selected from the group consisting of a polyclonal ROR1 antibody, a ROR1 antibody recognizing an N-terminal portion of ROR1, ab135669, an anti-human ROR1 goat polyclonal antibody, an anti-human ROR1 rabbit polyclonal antibody, an anti-ROR1 4A5, and anti-human ROR1 2A2.

In another aspect, the present disclosure provides a composition comprising a binding protein or an immunoglobulin-like binding protein or an antibody or a binding fragment thereof as described herein and a pharmaceutically acceptable carrier, diluent, or excipient. Pharmaceutically acceptable carriers for diagnostic and therapeutic use are well known in the pharmaceutical art, and are described, for example, in *Remington's Pharmaceutical Sciences*, Mack Publishing Co. (A. R. Gennaro (Ed.), 18$^{th}$ Edition, 1990) and in *CRC Handbook of Food, Drug, and Cosmetic Excipients*, CRC Press LLC (S. C. Smolinski, ed., 1992). Exemplary pharmaceutically acceptable carriers include any adjuvant, carrier, excipient, glidant, diluent, preservative, dye/colorant, surfactant, wetting agent, dispersing agent, suspending agent, stabilizer, isotonic agent, solvent, emulsifier, or any combination thereof. For example, sterile saline and phosphate buffered saline at physiological pH can be suitable pharmaceutically acceptable carriers. Preservatives, stabilizers, dyes or the like may also be provided in the pharmaceutical composition. In addition, antioxidants and suspending agents may also be used. Pharmaceutical compositions may also contain diluents such as water, buffers, antioxidants such as ascorbic acid, low molecular weight polypeptides (less than about 10 residues), proteins, amino acids, carbohydrates (e.g., glucose, sucrose, dextrins), chelating agents (e.g., EDTA), glutathione, and other stabilizers and excipients. Neutral buffered saline or saline mixed with nonspecific serum albumin are exemplary diluents.

Use of Anti-ROR1 Binding Proteins

In another aspect, the present disclosure provides methods for identifying cells that express full-length ROR1. In some embodiments, a method for identifying cells expressing ROR1 on their cell surface and/or that express the ROR1, comprises contacting a cell with a binding protein or an immunoglobulin-like binding protein as described herein, and detecting specific binding of the binding protein or immunoglobulin-like binding protein to the cell, thereby identifying the cells that express full-length ROR1. In certain embodiments, full-length ROR1 being detected is ROR1 normally expressed or endogenously by the cell. In further embodiments, a cell that is being contacted has been genetically engineered to overexpress an endogenous or heterologous ROR1. In certain embodiments, a cell is formalin fixed and embedded in paraffin. In other embodiments, a cell is frozen and embedded in Optimal Cutting Temperature compound (OCT). For example, such prepared cells or tissue are probed for the presence of full-length ROR1 in the cell by immunohistochemistry. In still other embodiments, the presence of full-length ROR1 in the cell is detected by immunoblot conducted by probing a lysate obtained from the cell.

In yet another aspect, a detection method is provided, the detection method comprising (a) contacting a biological sample with a binding protein or an immunoglobulin like binding protein as described herein; and (b) detecting specific binding of the binding protein or immunoglobulin-like binding protein to a peptide or epitope in the sample, or lack thereof, wherein the method thereby detects the presence or absence of a ROR1 or a ROR1 epitope in the sample. In some embodiments, the detection method further comprises comparing a level of the specific binding detected in (b) to a reference level, wherein an increased level of binding as compared to the reference level indicates the presence of ROR1 or ROR1 epitope in the sample. In particular embodiments, the sample is obtained from a subject. In further embodiments, the sample comprises a tissue section and/or a cell. In certain embodiments, the sample comprises a formalin-fixed or frozen tissue section and/or permeablized cell and/or the sample is derived from a tumor, which tumor selected from the group consisting of hematologic malignancies and solid tumors; and/or is derived from a normal tissue. For example, in particular embodiments, the sample is (a) derived from CLL or MCL or (b) is derived from an ovarian cancer, a lung cancer, which optionally is selected from among lung adenocarcinoma, adenocarcinoma, squamous cell carcinoma, small cell carcinoma, and atypical carcinoid, or a breast cancer, which optionally is a triple-negative breast cancer; or (c) is derived from a normal tissue selected from the group consisting of bone marrow, adipose tissue, parathyroid, esophagus, and pancreas. In some embodiments, a sample comprises a cell that is formalin fixed and embedded in paraffin, or the cell is frozen and embedded in Optimal Cutting Temperature compound (OCT). In some embodiments, the presence of full-length ROR1 in the cell is detected by immunohistochemistry or immunoblotting.

In yet another aspect, the present disclosure provides methods for identifying the presence of a ROR1 in a tissue sample. In some embodiments, a method comprises contacting a tissue sample with a binding protein or an immunoglobulin-like binding protein as described herein, and detecting specific binding to the tissue, thereby identifying tissue that expresses the ROR1, which optionally is full-length and/or cell-surface ROR1. In certain embodiments, a tissue sample is formalin fixed and embedded in paraffin. In other embodiments, a tissue sample is frozen and embedded in Optimal Cutting Temperature compound (OCT). In further embodiments, the presence of full-length ROR1 in the tissue sample is detected by immunohistochemistry. In still further embodiments, the presence of full-length ROR1 in the tissue sample is detected by immunoblot conducted by probing a cell lysate.

In some embodiments, a method for quantifying the amount of full-length ROR1 in a cell or tissue sample is provided. In certain embodiments, a method comprises contacting a cell or tissue with a binding protein or an immunoglobulin-like binding protein as described herein, and quantifying specific binding of the binding protein or immunoglobulin-like binding protein to the cell, thereby quantifying the amount of full-length ROR1 of a cell or tissue. In some embodiments the full-length ROR1 expressed by the cell is ROR1 normally expressed endogenously. In other embodiments, a cell has been genetically engineered to overexpress ROR1. In further embodiments, a cell or tissue sample is formalin fixed and embedded in paraffin. In other embodiments, a cell or tissue sample is frozen and embedded in Optimal Cutting Temperature compound (OCT). In still further embodiments, the amount of full-length ROR1 in the cell or tissue sample is detected by immunohistochemistry. In yet other embodiments, the amount of full-length ROR1 in the cell is detected by immunoblot conducted by probing a cell lysate.

In still another aspect of the present disclosure is a method for identifying a subject having, or at risk of having, a disease associated with cells expressing full-length ROR1. In certain embodiments of this disclosure, a subject or biological source may be suspected of having or at risk for having a disease, disorder, or condition, including a malignant disease, disorder, or condition. As used herein, "risk" is the likelihood (probability) of a subject developing a specified disease or condition. Risk is a representation of the likelihood that subject will develop a disease within a period of time (such as 1, 2, 3, 4, or 5 years). A "high risk" indicates a greater than 50% chance that the subject will develop a specified disease or condition. Conversely, a "low risk" indicates a less than 50% chance that the subject will develop a specified disease or condition. In some embodiments, the method for identifying a subject having, or being at risk of having, a disease associated with cells expressing full-length ROR1 comprises contacting a tissue sample from the subject with a binding protein or an immunoglobulin-like binding protein as described herein and detecting specific binding of the binding protein or immunoglobulin-like binding protein to the tissue, and thereby identifying a subject having, or at risk of having, a disease associated with cells expressing ROR1 or full-length ROR1.

For example, a subject may be identified as having, or at risk of having, a disease associated with cells expressing full-length ROR1 if a test sample of cells or tissue taken from the subject has detectable or an increased level of full-length ROR1 as compared to a control sample. In certain instances, a subject may be identified as having, or at risk of having, a disease associated with cells expressing full-length ROR1 when full-length ROR1 is present in a test sample but is absent or undetectable in a control. In further examples, the difference between test and control levels may be about 2-fold, about 2.5-fold, about 3-fold, about 3.5-fold, about 4-fold, about 4.5-fold, about 5-fold, about 5.5-fold, about 6-fold, about 6.5-fold, about 7-fold, about 7.5-fold, about 8-fold, about 8.5-fold, about 9-fold, about 9.5-fold, about 10-fold, about 15-fold, about 20-fold, about 30-fold, or more. A biological sample is referred to as a "test sample" when being tested or compared to a "control." A "control," as used herein, refers to an undiseased sample from the same patient and same tissue, a sample from a subject not having or suspected of having the disease of interest, a pool of samples (e.g., including samples from two to about 100,000 subjects) from various subjects not having or suspected of having the disease of interest, or data from one or more subjects not having or suspected of having the disease of interest (e.g., a database containing information on biomarker levels from one to about 5,000 to about 10,000 to about 100,000 to about 1,000,000 or more subjects). In certain embodiments, a "test sample" is analyzed and the results (i.e., expression of ROR1) compared to a "control" comprising an average or certain identified baseline level calculated from a database having data derived from a plurality of analyzed undiseased or normal samples.

In some embodiments, a "reference" or "standard" may optionally be included in an assay, which provides a measure of a standard or known baseline level of a target molecule (e.g., "normal" level). In certain embodiments, a reference sample is a pool of samples (e.g., 2, 3, 4, 5, 6, 7, 8, 9, 10, or more samples combined) from healthy individuals (i.e., not having or suspected of having the disease of interest). In certain instances, a "test sample" and a "control sample" will be examined in an assay along with a reference sample. In these instances, the "test" and "control" samples may be collectively referred to as the "target samples" since they are being compared to a reference sample.

In certain embodiments, a subject may be suspected of having or being at risk for having a disease associated with cells expressing full-length ROR1, and in certain other embodiments of this disclosure the subject may be known to be free of a risk or presence of such disease. In some embodiments, a subject is suspected of having or being at risk because the subject belongs to a subpopulation identified by specific characteristics, such as age, gender, diet, ethnicity, family history, or a combination thereof. In some embodiments, the subject is suspected of being at risk if the subject has a mutation in a gene or heritable disease. In some embodiments, a disease associated with cells expressing full-length ROR1 is a hyperproliferative disease or condition. For example, in certain embodiments, a hyperproliferative disease or condition is a tumor. In some embodiments, a tumor may be a hematologic tumor, such as CLL or MCL. In further embodiments, a tumor may be a solid tumor, such as a breast cancer, lung cancer, ovarian cancer, or pancreatic cancer tumor. For example, in some embodiments, a cancer is an adenocarcinoma, a squamous cell carcinoma, a small cell carcinoma, or an atypical carcinoid. In certain embodiments, a lung cancer is a lung adenocarcinoma. In certain other embodiments, a breast cancer is a triple-negative breast cancer. In some embodiments, the tumor comprises a primary tumor, a metastatic tumor, or both.

In any of the aforementioned methods comprising detecting specific binding of the binding protein, the method further comprises identifying the subject or sample as a candidate for treatment with an anti-ROR1 therapy (e.g., an immunotherapy, such as an adoptive cell therapy) if the specific binding is detected in at least 50%, at least 60%, at least 70%, at least 80%, or at least 90% of the surface area of the tissue or of the cells in the tissue, are determined by the method to express the ROR1 or epitope.

In the aforementioned methods comprising detecting specific binding of the binding protein, the method further comprises identifying the subject or sample as a candidate for treatment with an anti-ROR1 therapy (e.g., an immunotherapy, such as an adoptive cell therapy) if the tissue from which the sample is derived is found to uniformly or homogenously express the ROR1 or epitope thereof, as determined by the method.

In yet other aspects of the present disclosure, provided is a method for identifying whether a subject having a hyperproliferative disease or condition would benefit from an ROR1-specific treatment, comprising contacting a tissue sample from the subject with a binding protein as described herein and detecting specific binding of the binding protein to the tissue, thereby identifying a subject that would benefit from an ROR1-specific treatment. In some embodiments, a ROR1-specific treatment is an immunotherapy, such as a T cell therapy comprising administering T cells expressing a ROR1 CAR, such as the ROR1 CAR described in Hudecek et al. (*Blood* 116: 4532-41, 2010). Exemplary ROR1 CARs target the extracellular portion of ROR1, and therefore target the full-length ROR1 isoform but not the intracellular isoform. Accordingly, in some embodiments, a method for identifying a subject that would benefit from a ROR1 CAR T cell therapy is provided, wherein expression of full-length ROR1, as indicated by specific binding of the binding protein or immunoglobulin-like binding protein to the tissue, identifies a subject as being able to benefit from the therapy. In certain embodiments, the treatment is an immunotherapy, which optionally is an adoptive cell therapy, which optionally comprises a chimeric antigen receptor comprising an anti-ROR1 antibody, which optionally is or competes for binding with the antibody designated as R12. Antibody R12 is disclosed in Yang et al. (*PLoSONE* 6:e21018, 2011) and Hudecek et al. (*Clin. Cancer Res.* 19:3153, 2013), which antibody and antigen-binding fragments thereof are incorporated herein by reference. In some embodiments, a subject is identified as a subject that would benefit from the ROR1-specific treatment if the specific binding is detected in at least 40%, at least 50%, at least 60%, at least 70%, at least 75%, at least 80%, at least 85%, at least 90%, or at least 95% or ranges from at least 60% to at least 85% or at least 50% to at least 90% of the surface area of the tissue or of the cells in the tissue, are determined by the method to express the ROR1 or epitope thereof. In some embodiments, the subject is identified as a subject that would benefit from the ROR1-specific treatment if the tissue from which the sample is derived is determined by the method to uniformly or homogenously express the ROR1 or epitope thereof. In particular embodiments, the ROR1-specific treatment is an immunotherapy, such as an adoptive cell therapy. In any of the aforementioned embodiments, the ROR1-specific treatment comprises a chimeric antigen receptor comprising an anti-ROR1 binding protein or antibody, such as an antibody that is the antibody designated as R12 or is a binding protein or antibody that competes for binding with the R12 antibody.

In still more aspects of the invention, there is provided a method for determining the prognosis of a subject having a hyperproliferative disease or condition associated with cells expressing full-length ROR1, comprising contacting a tissue sample from the subject with a binding protein as described herein, and detecting specific binding of the binding protein to the tissue, wherein detecting specific binding to full-length ROR1 in tissue identifies the subject as having a poor prognosis in the absence of an ROR1-specific treatment. As used herein, "prognosis" is the likelihood of the clinical outcome for a subject afflicted with a specific disease, disorder, or condition. With regard to cancer, the prognosis is a representation of the likelihood (probability) that the subject will survive (such as for 1, 2, 3, 4, or 5 years) or the likelihood that the tumor will metastasize. A "poor prognosis" indicates a greater than 50% chance that the subject will not survive to a specified time point (such as 1, 2, 3, 4, or 5 years), or a greater than 50% chance that the tumor will metastasize. Conversely, a "good prognosis" indicates a greater than 50% chance that the subject will survive to a specified time point (such as 1, 2, 3, 4, or 5 years), or a greater than 50% chance that the tumor will not metastasize.

In some embodiments, detecting full-length ROR1, indicated by specific binding of the binding protein to a tissue, identifies the subject as having a tumor, tumor metastasis, or both. In some embodiments, a method for determining the prognosis of a subject having a hyperproliferative disease or condition associated with cells expressing full-length ROR1 comprises contacting a tissue sample from the subject with a binding protein as described herein, and detecting specific binding of the binding protein to the tissue, wherein detecting full-length ROR1 in the tissue identifies the subject as having a poor prognosis in the absence of an ROR1-specific treatment. In any of these embodiments, the tissue sample is formalin fixed and embedded in paraffin, or the tissue sample is frozen and embedded in OCT. In certain embodiments, the presence of full-length ROR1 in a tissue sample is detected by immunohistochemistry or immunoblotting.

In any of the aforementioned embodiments comprising detecting specific binding of the binding protein, the method further comprises treating the subject with an anti-ROR1 therapy, such as an immunotherapy. In certain embodiments, the immunotherapy comprises an adoptive cell therapy. In any of these embodiments, the anti-ROR1 therapy comprises a chimeric antigen receptor specific for ROR1, wherein the chimeric antigen receptor specific for ROR1 comprises an anti-ROR1 antibody binding protein or binding domain. In certain embodiments, the chimeric antigen receptor specific for ROR1 comprises the binding domain from the antibody designated as R12 or comprises a binding domain that competes for binding with the R12 antibody.

In certain embodiments, provided herein are methods of evaluating the efficacy of a therapy in a human subject by administering the therapy and determining the efficacy of the therapy. "Efficacy" is a measure of how well a therapy treats or reduces disease burden, such as tumor size or number. A reduction in detectable ROR1 is an indication of reduction in disease burden and good efficacy. No change in detectable ROR1 levels or a reduced rate of detectable ROR1 levels can be an indication that a therapy is tumorostatic. No effect on a statistically significant rate of increase in detectable ROR1 levels is an indication of poor efficacy, minimal efficacy, or a lack of efficacy. In certain embodiments, efficacy can be correlated with survival time. For example, therapy that increases survival time in patients in a statistically significant manner as compared to a control is correlated with higher efficacy. Conversely, a therapy that does not increase survival time in a statistically significant manner as compared to control is correlated with poor, minimal, or no efficacy.

In some embodiments, the efficacy of a therapy is assessed by measuring the expression of full-length ROR1 in a cell or tissue sample compared to a control or to previously measured levels. In some embodiments, the cell or tissue sample is formalin fixed and embedded in paraffin, or the cell is frozen and embedded in Optimal Cutting Temperature compound (OCT). The level of full-length ROR1 in the sample is measured by detecting the amount of binding protein or immunoglobulin-like binding protein that specifically binds to full-length ROR1. In some embodiments, specific binding of a binding protein or an immunoglobulin-like binding protein to a cell or tissue is detected by immunohistochemistry or immunoblotting. In some aspects of the method, the therapy being evaluated is surgery, chemotherapy, cytotoxic therapy, immune mediated therapy, targeted therapies, radiation therapy, or chemoradiotherapy, or any combination thereof. In some embodiments, the therapy treats a hyperproliferative disorder or condition, such as cancer. In some embodiments, the therapy is an immunotherapy, such as a T cell therapy comprising administering T cells expressing a ROR1 CAR, such as the ROR1 CAR described in Hudecek et al. (*Blood* 116: 4532-41, 2010).

In further aspects, the present disclosure provides methods of treatment comprising administering an anti-ROR1 therapy to a subject having a disease or condition, wherein a tissue or sample of the disease or condition in the subject has been identified as having uniform or homogenous expression of surface-expressed ROR1. In certain embodiments, the disease or condition is a tumor, such as a solid tumor or a hematologic tumor (e.g., the tumor is a CLL, MCL, breast cancer, lung cancer, ovarian cancer, or pancreatic cancer tumor; or the tumor is a lung adenocarcinoma, adenocarcinoma, squamous cell carcinoma, small cell carcinoma, atypical carcinoid, or a triple-negative breast cancer). In certain embodiments, a method of treatment comprises administering to a subject having a disease or condition selected from among lung adenocarcinoma, adenocarcinoma, squamous cell carcinoma, small cell carcinoma, atypical carcinoid, and triple-negative breast cancer. In particular embodiments, the anti-ROR1 therapy comprises an immunotherapy, such as adoptive cell therapy or a cell expressing a chimeric antigen receptor comprising an anti-ROR1 antibody fragment, such as the antibody designated R12 (see Yang et al., PLoSOne 6:e21018, 2011, and Hudecek et al., *Clin. Cancer Res.* 19:3153, 2013, which antibody and antigen-binding fragments thereof are incorporated herein by reference).

In some embodiments, a method of treatment is provided, comprising administering to a subject having a disease or condition an anti-ROR1 therapy, wherein a tissue or sample of the disease or condition in subject has been identified as having uniform or homogenous expression of surface-expressed ROR1. In certain embodiments, the disease or condition is a tumor, which optionally is a solid tumor or a hematologic tumor. In some further embodiments, the tumor is selected from the group consisting of CLL, MCL, breast cancer, lung cancer, ovarian cancer, and pancreatic cancer. In particular embodiments, the tumor is a lung adenocarcinoma, adenocarcinoma, squamous cell carcinoma, small cell carcinoma, atypical carcinoid, or a triple-negative breast cancer. In some embodiments, the anti-ROR1 therapy comprises an immunotherapy, such as an adoptive cell therapy. In some embodiments, the immunotherapy comprises a cell expressing a chimeric antigen receptor comprising an anti-ROR1 antibody fragment. In particular embodiments, the chimeric antigen receptor comprises an anti-ROR1 antibody fragment derived from an antibody designated as R12, an antibody containing the antigen-binding region thereof, or an antibody that competes for binding with the antibody designated as R12. In still further embodiments, the cell expressing a chimeric antigen receptor comprises a T cell or an NK cell. In the aforementioned embodiments, the expression of surface-expressed ROR1 has been determined using the methods disclosed herein.

In another aspect, the present disclosure provides kits comprising materials useful for carrying out diagnostic methods according to the present invention. In certain aspects, a kit comprising a binding protein or immunoglobulin-like binding protein as described herein is provided. In some embodiments, the kit is used for detecting the presence of full-length ROR1 in a cell or tissue sample. In some such embodiments, the kit is used for detecting the presence of full-length ROR1 in a tissue sample, and the tissue sample is formalin fixed and embedded in paraffin. In other embodiments, the tissue sample is frozen and embedded in OCT. In some embodiments, the presence of full-length ROR1 in a tissue sample is detected by immunohistochemistry or immunoblot. In some embodiments, the kit includes a secondary antibody comprising HRP.

In still other aspects, a kit comprising a composition is provided, wherein the composition comprises a binding protein or an immunoglobulin-like binding protein as described herein and a carrier or excipient. In some embodiments, a kit is used for detecting the presence of full-length ROR1 in a cell or tissue sample. In some embodiments, the sample is a tissue sample that is formalin fixed and embedded in paraffin. In other such embodiments, the tissue sample is frozen and embedded in OCT. In some embodiments, the presence of full-length ROR1 in a tissue sample is detected by immunohistochemistry or immunoblot. In some embodiments, the kit includes a secondary antibody comprising HRP.

The methods for identifying the presence of full-length ROR1 described herein may be performed by diagnostic laboratories, experimental laboratories, or practitioners. The invention provides kits, which can be used in these different settings. Materials and reagents for characterizing biological samples and diagnosing a hyperproliferative disease or condition in a subject according to the methods herein may be assembled together in a kit. In certain aspects, a kit comprises a binding protein or an immunoglobulin-like binding protein as described herein, and instructions for using the kit according to a method of this disclosure.

The kits comprising a binding protein or an immunoglobulin-like binding protein as described herein may further comprise one or more substrates to anchor the antigen binding molecules, including microarray slides, beads, plastic tubes, or other surfaces, secondary antibodies, labeling buffer or reagents, wash buffers or reagents, immunodetection buffer or reagents, and detection means. Protocols for using these buffers and reagents for performing different steps of the procedure may be included in the kit. The reagents may be supplied in a solid (e.g., lyophilized) or liquid form. The kits of the present disclosure may optionally comprise different containers (e.g., slide, vial, ampoule, test tube, flask or bottle) for each individual buffer or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, kits of the present disclosure further include control samples, control slides, reference samples, reference slides, or any combination thereof. Instructions for using the kit, according to one or more methods of this disclosure, may comprise instructions for processing the biological sample obtained from a subject, performing the test, or instructions for interpreting the results, or any combination thereof. Kits of the present disclosure may further include as a notice in the form prescribed by a governmental agency (e.g., FDA) regulating the manufacture, use, or sale of pharmaceuticals or biological products.

Nucleic Acids and Host Cells For Anti-ROR1 Binding Protein Production

In another aspect, the present disclosure provides an isolated polynucleotide encoding an immunoglobulin binding domain or an immunoglobulin-like binding protein as described herein. In certain embodiments, polynucleotides encoding immunoglobulin binding domains or proteins may be codon optimized to enhance or maximize expression in certain types of cells (e.g., Scholten et al., *Clin. Immunol.* 119: 135-145, 2006). As used herein a "codon optimized" polynucleotide is a heterologous polypeptide having codons modified with silent mutations corresponding to the abundances of host cell tRNA levels.

In some embodiments, a nucleic acid molecule encodes a binding protein (e.g., an antibody heavy and light chains, or an antibody binding domain comprising a $V_H$ and $V_L$ binding regions) wherein two or more domains are separated by a cleavage site. In certain embodiments, a cleavage site comprises from about 2 to about 20 amino acids amino-terminal to the $V_H$ or $V_L$, from about 2 to about 20 amino acids carboxy-terminal to the $V_H$ or $V_L$, a self-cleaving amino acid sequence, or a combination thereof. In certain embodiments, the cleavage site comprises from about 2 to about 15, about 2 to about 10, or about 2 to about 5 amino acids at the amino-terminal or the carboxy-terminal end of the binding protein domains. In some embodiments, the cleavage site is a self-cleaving amino acid sequence comprising a 2A peptide from porcine teschovirus-1 (P2A) (such as the amino acid sequence set forth in SEQ ID NO.:17), equine rhinitis A virus (E2A) (such as the amino acid sequence set forth in SEQ ID NO.:19), *Thosea asigna* virus (T2A) (such as the amino acid sequence set forth in SEQ ID NO.:18), foot-and-mouth disease virus (F2A) (such as the amino acid sequence set forth in SEQ ID NO.:20), or any combination thereof (see, e.g., Kim et al., *PLOS One* 6:e18556, 2011, which 2A nucleic acid and amino acid sequences are incorporated herein by reference in their entirety).

In yet another aspect, an expression construct comprising a polynucleotide encoding a binding protein or an immunoglobulin-like binding protein as described herein is provided. The disclosure also provides an expression construct comprising a polynucleotide encoding a binding protein or an immunoglobulin-like binding protein, and a peptide tag or protein tag. In some embodiments, a polynucleotide may be operably linked to an expression control sequence. As used herein, "expression construct" refers to a DNA construct containing a nucleic acid molecule that is operably-linked to a suitable control sequence capable of effecting the expression of the nucleic acid molecule in a suitable host. An expression construct may be present in a vector (e.g., a bacterial vector, a viral vector) or may be integrated into a genome. The term "operably linked" refers to the association of two or more polynucleotides on a single polynucleotide fragment so that the function of one is affected by the other. For example, a promoter is operably-linked with a coding sequence when it is capable of affecting the expression of that coding sequence (i.e., the coding sequence is under the transcriptional control of the promoter). The term "expression control sequence" (also called a regulatory sequence) refers to polynucleotide sequences that effect the expression and processing of coding sequences to which they are operably linked. For example, expression control sequences may include transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion.

In some embodiments, an expression construct is present in a vector. A "vector" is a nucleic acid molecule that is capable of transporting another nucleic acid. Vectors may be, for example, plasmids, cosmids, viruses, a RNA vector or a linear or circular DNA or RNA molecule that may include chromosomal, non-chromosomal, semi-synthetic or synthetic nucleic acids. Exemplary vectors are those capable of autonomous replication (episomal vector) or expression of nucleic acids to which they are linked (expression vectors). Exemplary viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996). In some embodiments, a vector is a plasmid. In some other embodiments, a vector is a viral vector. In some such embodiments, the viral vector is a lentiviral vector or a γ-retroviral vector.

In certain other aspects, the disclosure provides a host cell comprising an expression construct or vector, or a polynucleotide provided by an expression construct as described herein. As used herein, the term "host" refers to a cell or microorganism targeted for genetic modification with a heterologous or exogenous nucleic acid molecule to produce a polypeptide of interest (e.g., an anti-ROR1 antibody or antigen-binding fragment thereof). In certain embodiments, a host cell may optionally already possess or be modified to include other genetic modifications that confer desired properties related or unrelated to biosynthesis of the heterologous or exogenous protein (e.g., inclusion of a detectable marker). More than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. When two or more exogenous nucleic acid molecules are introduced into a host cell, it is understood that the two more exogenous nucleic acid molecules can be introduced as a single nucleic acid molecule (e.g., on a single vector), on separate vectors, integrated into the host chromosome at a single site or multiple sites. The number of referenced heterologous nucleic acid molecules or protein activities refers to the number of encoding nucleic acid molecules or the number of protein activities, not the number of separate nucleic acid molecules introduced into a host cell.

In still further aspects, the present disclosure provides a process for making a binding protein or an immunoglobulin-like binding protein as described herein, comprising culturing a host cell comprising an expression construct or vector, or a polynucleotide provided by an expression construct as described herein, under suitable conditions to express the binding protein or immunoglobulin-like binding protein, and optionally isolating the binding protein or immunoglobulin-like binding protein from the culture.

EXAMPLES

Example 1

Tissue Distribution of Ror1 Transcript Expression

Expression of Ror1 transcript was characterized in a panel of various different human and rhesus macaque tissues by quantitative real-time PCR. An RT-qPCR assay was used to determine ROR1 expression in human and macaque tissues. cDNA from most tissues was obtained from BioChain®, and additional cDNA samples were prepared using the SuperScript-III First-Strand-Synthesis Kit starting with RNA (1 µg) from human pancreas and colon (Clontech) and from primary B-CLL cells. cDNA (2 µL) was used in a 10-µL reaction using the Power-SYBR-Green-PCR mix on the 7900HT Fast Real-Time PCR System (Life Technologies). ROR1 expression was normalized to the geometric mean of the housekeeping genes GAPDH and TATA-binding protein (TBP) using gene-specific forward (F) and reverse (R) primers including:

```
human ROR1-F:
                                    [SEQ ID NO.: 39]
    5'-AGCGTGCGATTCAAAGGATT-3', human ROR1-R:
                                    [SEQ ID NO.: 40]
    5'-GACTGGTGCCGACGATGACT-3', human GAPDH-F:
                                    [SEQ ID NO.: 41]
    5'-GAAGGTGAAGGTCGGAGTC-3', human GAPDH-R:
                                    [SEQ ID NO.: 42]
    5'-GAAGATGGTGATGGGATTTC-3', human TBP-F:
                                    [SEQ ID NO.: 43]
    5'-TGCACAGGAGCCAAGAGTGAA-3', human TBP-R:
                                    [SEQ ID NO.: 44]
    5'-CACATCACAGCTCCCCACCA-3', rhesus ROR1-F:
                                    [SEQ ID NO.: 45]
    5'-AGCTTGCGATTCAAAGGATT-3', rhesus ROR1-R:
                                    [SEQ ID NO.: 46]
    5'-GACTGGTGGTGATGATGACT-3', rhesus GAPDH-F:
                                    [SEQ ID NO.: 47]
    5'-GAAGGTGAAGGTCGGAGTC-3', rhesus GAPDH-R:
                                    [SEQ ID NO.: 48]
    5'-GAAGATGGTGATGGGGCTTC-3', rhesus TBP-F:
                                    [SEQ ID NO.: 49]
    5'-TGCACAGGAGCCAAGAGTGAA-3',
and
```

-continued rhesus TBP-R:
[SEQ ID NO.: 50]
5'-CACATCACAGCTCCCCACCA-3'.

Primer efficiency and fold changes were determined using the Pfaffl method (*Nucleic Acids Res.* 29:e45, 2001), and expression was determined relative to primary B-CLL cells.

Figure 2:
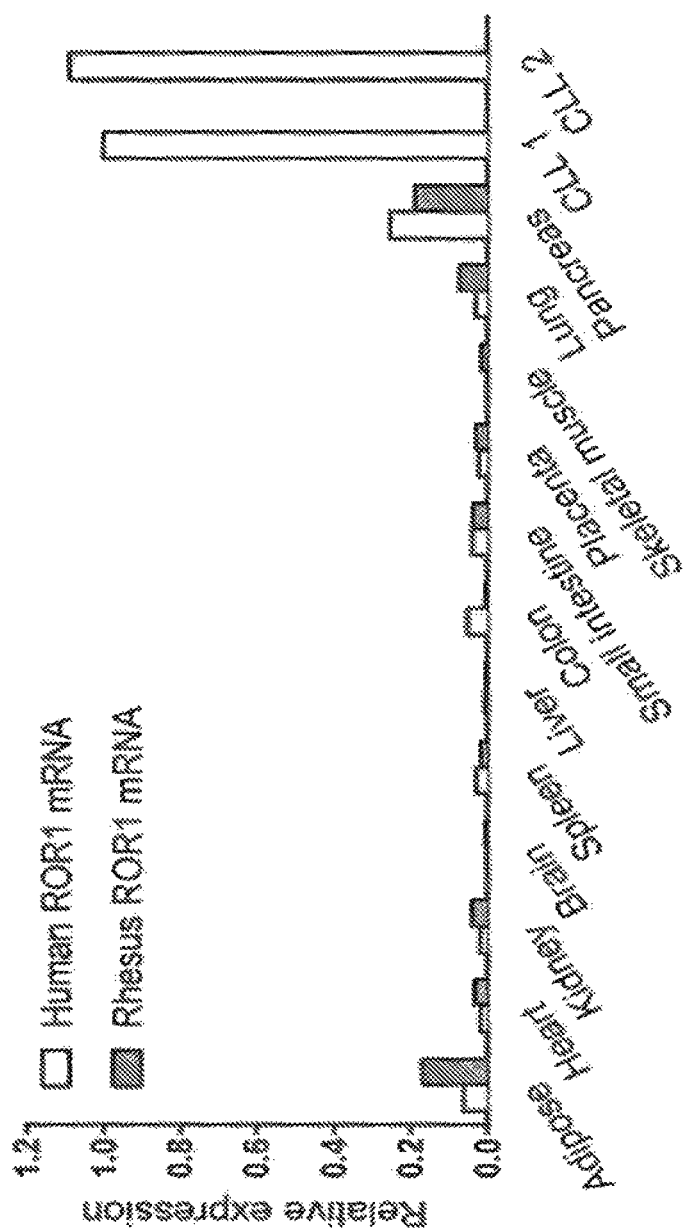
FIG. 2 illustrates expression level of full-length Ror1 transcript in various different tissues from normal human and rhesus macaque measured by real-time PCR. Primary chronic lymphocytic leukemia (CLL) cells from two different donors and known to express high levels of ROR1, were used as a positive control (see Hudecek et al., Blood 116: 4532, 2010).

As shown in FIG. 2, Ror1 transcript expression levels were essentially undetectable in most normal tissues. But, low levels of Ror1 transcript were detectable in adipose and pancreas as compared to CLL cells, which are known to express high levels of ROR1. Therefore, in view of high ROR1 expression is in tumors, while normal tissues show minimal to undetectable ROR1 expression, ROR1 would make a good therapeutic target since it is essentially a tumor-associated antigen and such therapeutics would likely have minimal to undetectable toxicity.

Example 2

Other Anti-ROR1 Antibodies Are Unable to Detect ROR1 Immunohistologically

Several published or commercially available anti-ROR1 antibodies were tested as immunohistochemistry (IHC) reagents on various cell lines and tissues to examine their ability to specifically detect ROR1 expression. IHC assays were performed on formalin-fixed-paraffin-embedded (FFPE) cells and tissues using the specific protocols published for each antibody. The anti-human ROR1 antibodies tested were anti-human ROR1 ab135669 (rabbit polyclonal antibody from abcam®, Cambridge, MA) (Zhang et al., *Sci. Rep.* 24:5811, 2014), anti-human ROR1 (goat polyclonal antibody AF2000 from R&D Systems, Minneapolis, MN) (Dave et al., *PLoS One* 7:e52655, 2012), anti-human ROR1 #4102 (rabbit polyclonal antibody from Cell Signaling Technologies, Danvers, MA) (Yamaguchi et al., *Cancer Cell* 21:348, 2012), anti-human ROR1 4A5 (mouse monoclonal antibody) (Zhang et al., *Am. J. Pathol.* 181:1903, 2012), and anti-human ROR1 2A2 (mouse monoclonal antibody from BioLegend, San Diego, CA).

IHC staining with commercially available ROR1-specific antibodies used published protocols (see Zhang et al., 2014; Dave et al., 2012; Yamaguchi et al., 2012; Zhang et al., 2012). For the 4A5 monoclonal antibody, antigen retrieval (Trilogy-30 minutes, high salt buffer-30 minutes) was followed by primary antibody (8 µg/mL) overnight and either CSA amplification (investigator protocol) or anti-mouse polymer. The staining for all antibodies was visualized with DAB.

Figure 3A:
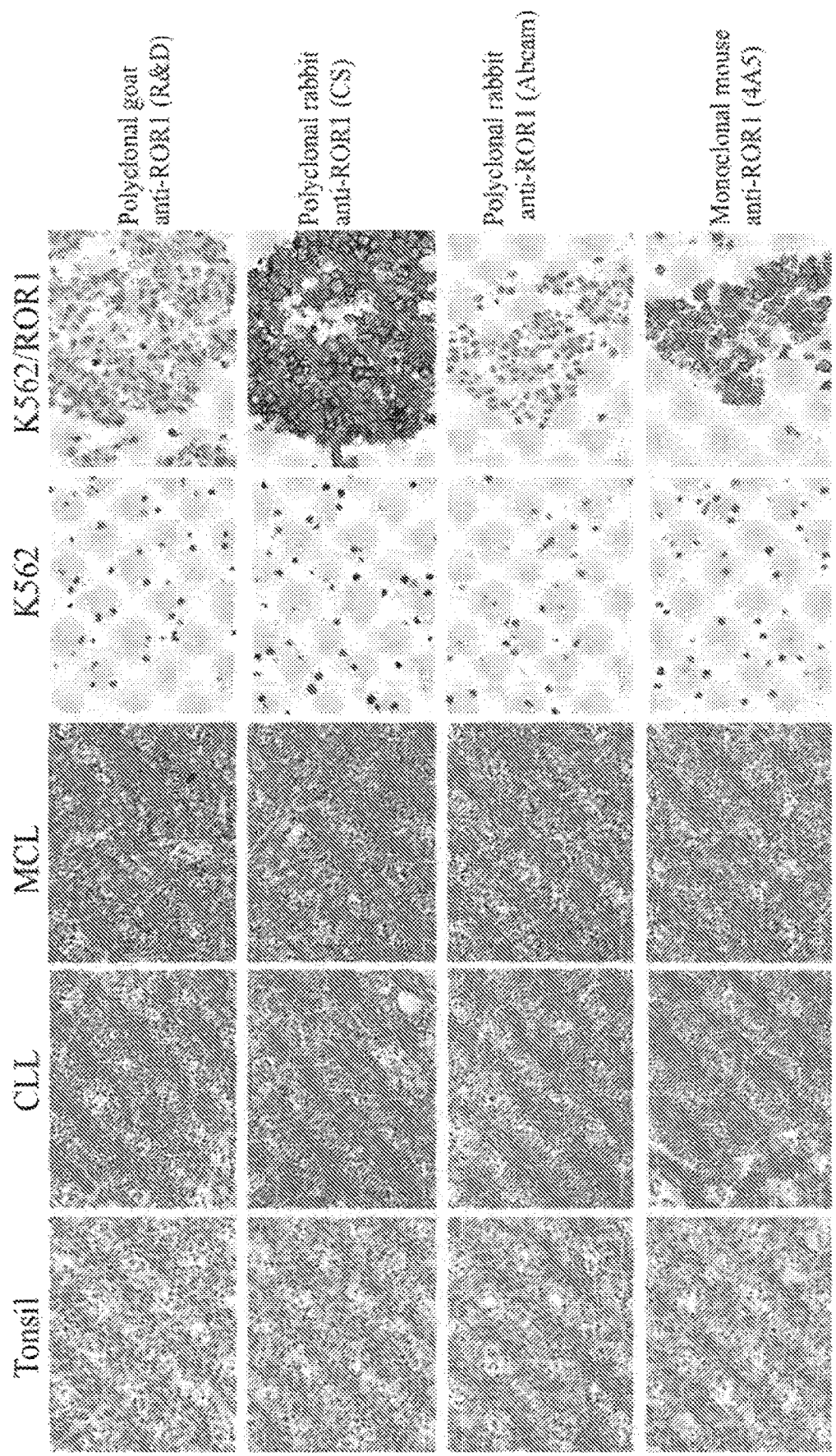
FIGS. 3A and 3B show the results of testing commercially available and published anti-ROR1 antibodies against various tissues by immunohistochemistry (IHC). Staining indicates binding of an anti-ROR1 antibody. (A) Commercially available and published anti-ROR1 antibodies were tested for their ability to specifically bind to ROR1 in normal tonsil tissue (ROR$^-$), CLL and mantle cell lymphoma (MCL) cells (ROR1$^+$, full-length), K562 cells (ROR1$^-$), and K562 cells transfected to overexpress full-length ROR1 (ROR1$^+$, full-length). (B) IHC staining using commercially available and previously published anti-ROR1 antibodies on ROR1-transfected K562 cells, control K562 cells, CLL lymph nodes, and tonsil tissue.

In a first experiment, ROR1 expression was determined in the following cells: (1) K562 (ROR⁻) cells (negative control); (2) tonsil tissue (ROR⁻) (negative control); (3) K562 cells transfected with Ror1, which overexpress full-length ROR1 (ROR1⁺) (positive control); (4) CLL lymph node (ROR1⁺, full-length); and MCL lymph nodes (ROR1⁺, full-length). Several of the published antibodies were able to detect overexpression of full-length ROR1 in K562 cells (evidenced by brown staining), but none of the known antibodies tested was able to detect endogenously expressed full-length ROR1 in CLL and MCL lymph nodes (FIG. 3A).

Figure 3B:
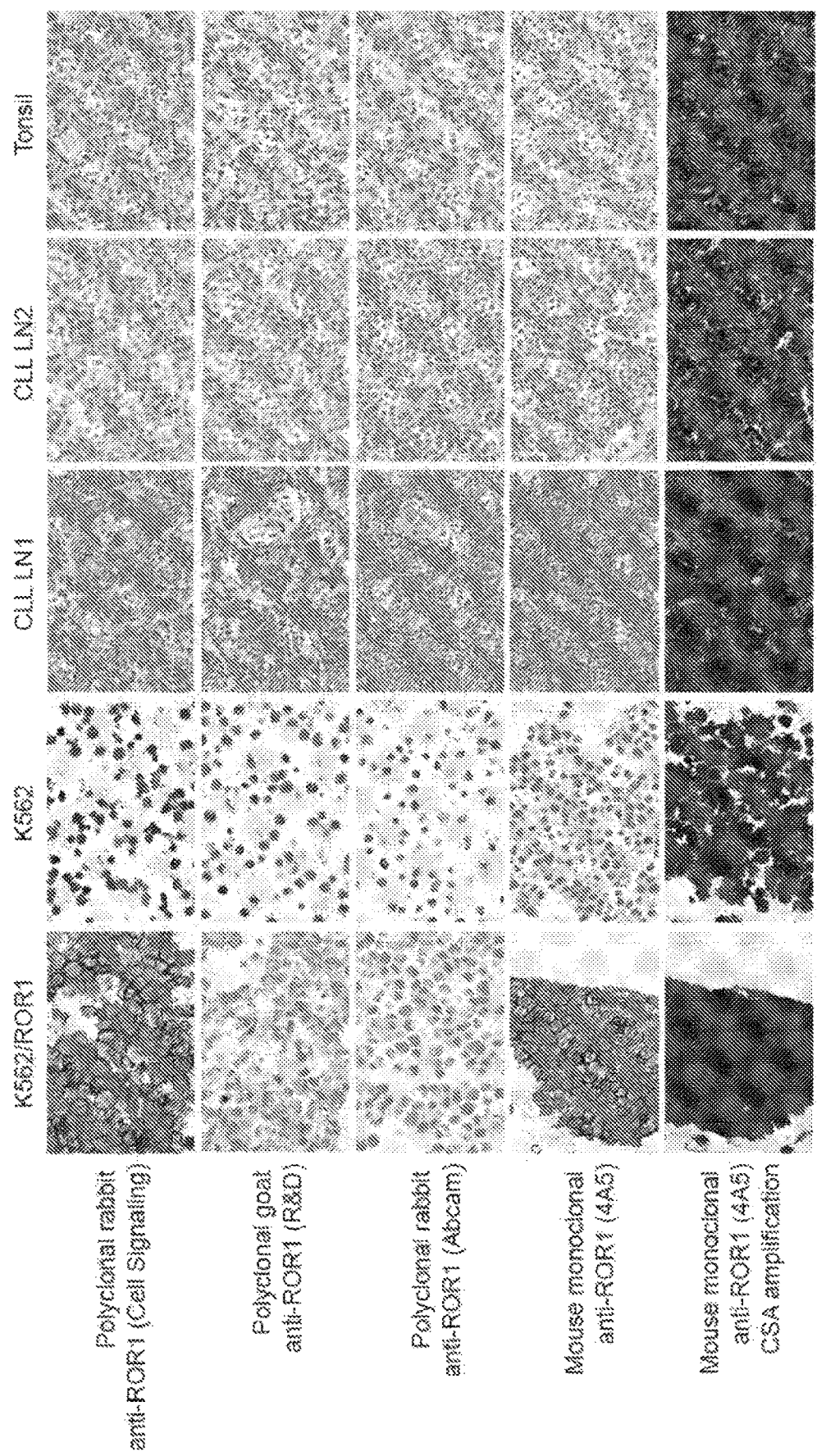

In a second experiment, ROR1 expression was determined in (1) K562 cells transfected with Ror1 (ROR1⁺); (2) K562 (ROR⁻) cells; (3) CLL lymph node tissue (ROR1⁺, full-length); and (4) tonsil tissue (ROR1⁻). Similar to the first experiment, most of the tested anti-ROR1 antibodies stained transduced cells that overexpressed ROR1 but did not stain FFPE CLL lymph node samples (FIG. 3B). Despite attempts using a variety of antigen retrieval and staining conditions, no conditions for reproducible detection of ROR1 in CLL lymph nodes with minimal background on normal tonsil were identified (data not shown).

Figure 4:
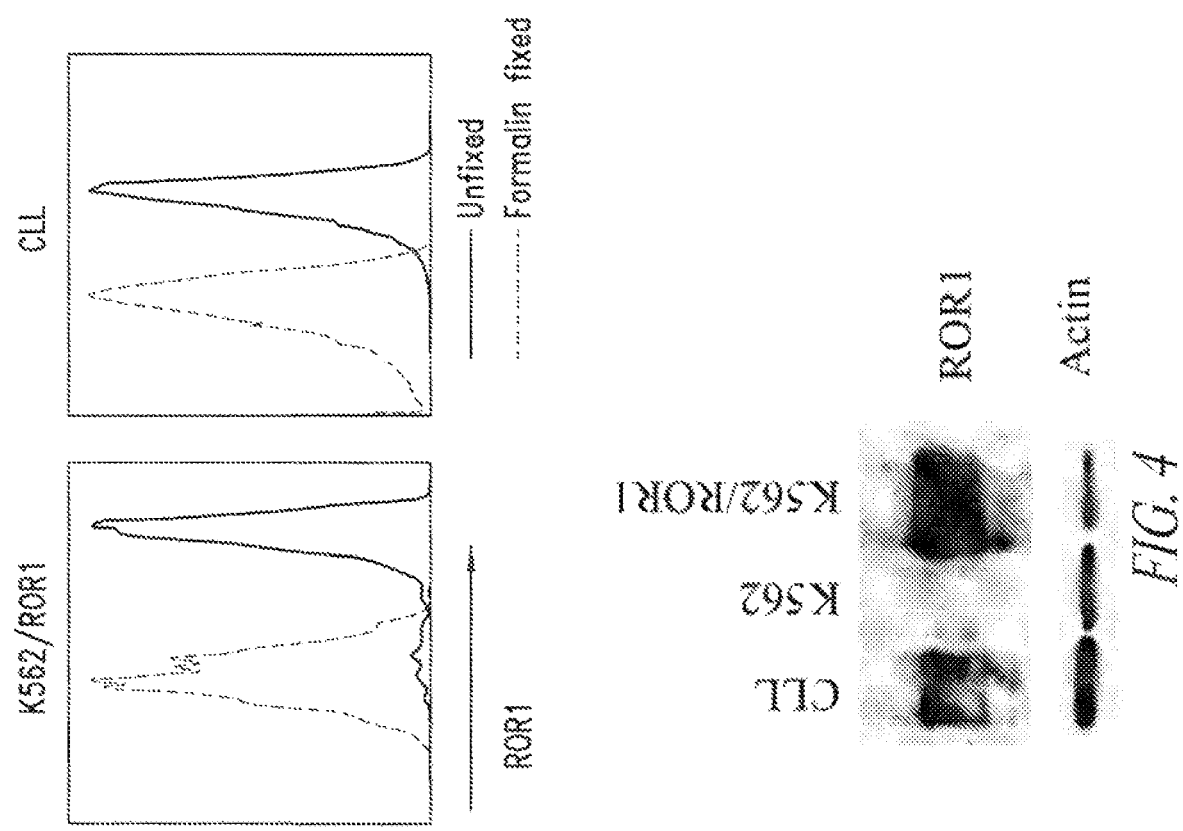
FIG. 4 shows that ROR1 binding by anti-ROR1 monoclonal antibody 2A2 (Biolegend, San Diego, CA) is reduced on formalin fixed tissue samples. ROR1$^+$ cells expressing ROR1 (CLL and K562/ROR1 cells) were formalin fixed overnight. The upper panel illustrates a reduced detection of ROR1 by flow cytometry analysis performed using anti-ROR1 monoclonal antibody 2A2 in formalin fixed ROR1$^+$ cells as compared to unfixed cells. The lower panel demonstrates by immunoblot that K562 cells transfected to overexpress ROR1 express much higher levels of ROR1 protein than endogenously expressed by CLL cells.

The failure of available reagents to stain ROR1 could be due to several reasons. The epitope recognized by antibodies in the N-terminal region in full-length ROR1 may be destroyed by formalin fixation, and antigen retrieval procedures in the IHC step may be unable to recover sufficient epitope for antibody recognition. Consistent with this possibility, formalin fixation of CLL cells or K562 cells transfected to overexpress full-length ROR1 reduced the detection of ROR1 by flow cytometry analysis (FIG. 4, upper panel). Furthermore, much higher levels of ROR1 were detected by immunoblotting K562 cells transfected to overexpress ROR1 as compared to CLL cells (FIG. 4, lower panel). Hence, currently available anti-ROR1 reagents may not be sensitive enough to detect endogenous ROR1 levels expressed in cancer tissue.

Accordingly, certain available anti-ROR1 antibodies are not entirely satisfactory, for example, in the ability to detect endogenous ROR1 expression on tumors and/or other tissues, e.g., in formalin-fixed or other prepared tissues, in an optimally sensitive and specific manner.

Example 3

Antibodies Specific For Full-Length ROR1

Figure 5:
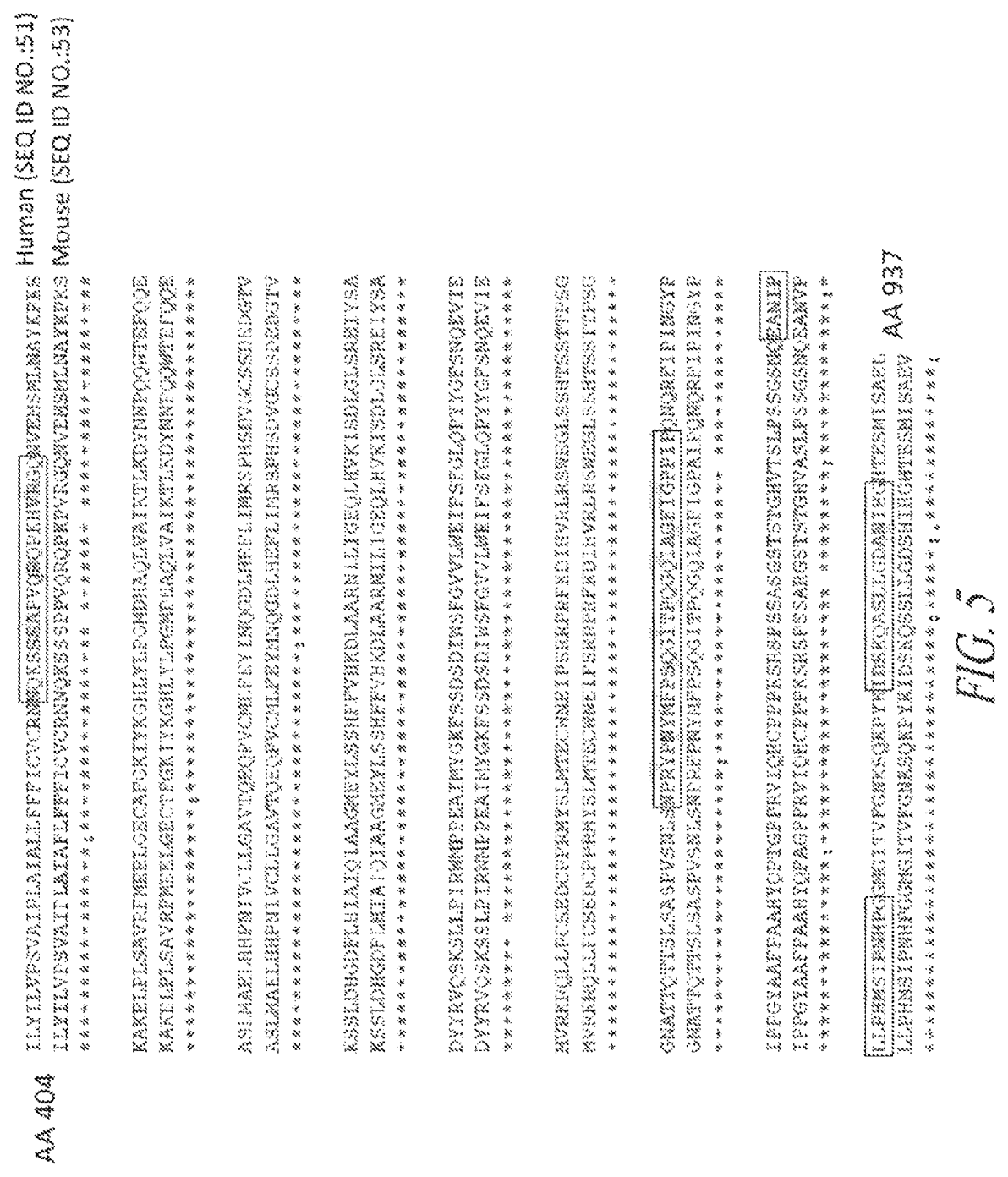

An antibody, which in some aspects is useful as a diagnostic, detection, and/or prognostic reagent, that is capable of detecting endogenous full-length ROR1 (ROR1_v1) while not cross-reacting with the short intracellular ROR1 isoform (ROR1_v2) was generated. In particular, the C-terminal portion of ROR1, which is present only in full-length ROR1 (and generally is the only isoform that localizes to the cell surface of, for example, a cancer cell), was used to generate a panel of antibodies. Briefly, female BALB/c and CD1 mice were immunized with a set of four peptides corresponding to amino acids located in the C-terminal region of human ROR1 (FIG. 5). Because ROR1 is highly conserved between mice and humans (97% amino acid homology), peptides from the intracellular region of ROR1_v1 having the maximum amino acid differences between human and mouse ROR1 (but having minimal homology to other sequences in the human proteome) were chosen to facilitate eliciting an immune response in mice. The four synthetic peptides were coupled to KLH. Polyclonal sera from immunized mice were tested to identify mice with high titer anti-ROR1 antibodies. Polyclonal sera were screened by immunoblotting against ROR1⁺ CLL and K562 ROR1⁻ cell lysates using the WES immunoblot device (ProteinSimple, Bio-Techne). Then, using conventional methods, hybridomas were made from splenocytes of mice having high anti-ROR1 titer to generate monoclonal antibodies, and 1222 clones were selected based on binding to fluorescently-labeled target antigen. Hybridomas were picked and ranked for peptide binding using a cytometric bead array carrying the ROR1 peptide cocktail.

Figure 6A:
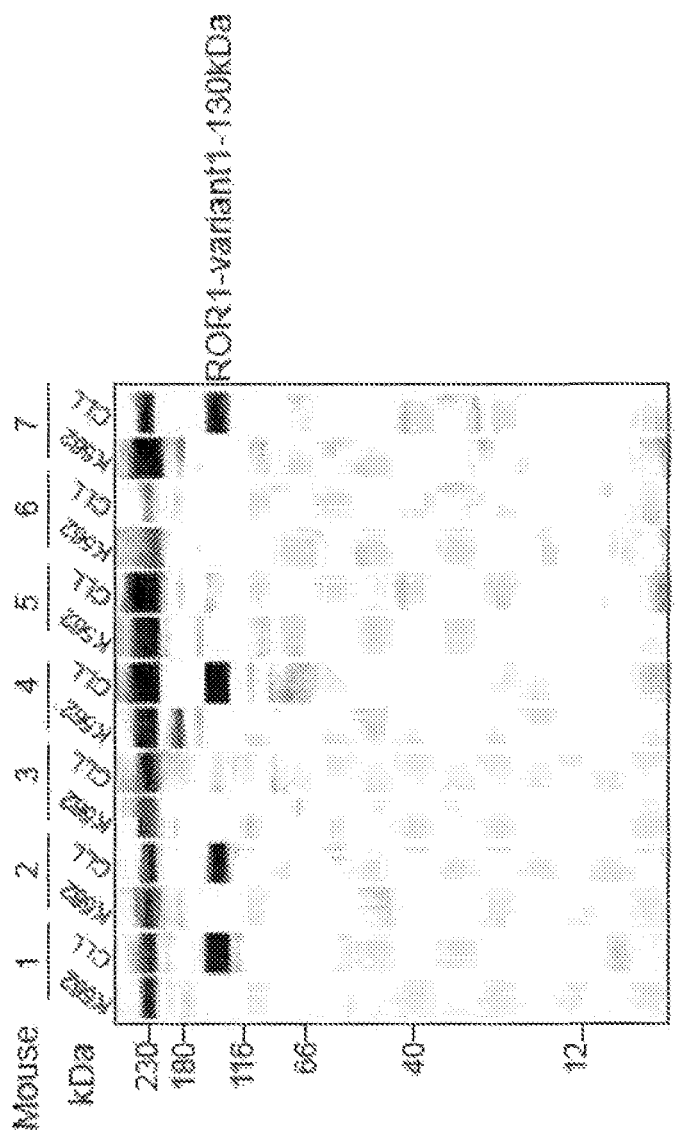
FIGS. 6A and 6B illustrate the screening of polyclonal mouse sera and hybridoma clones for the production of antibodies that bind to the C-terminal portion of ROR1. (A) Screening of multiple polyclonal mouse sera against ROR1$^-$ K562 cells and ROR1$^+$ CLL cell lysate by immunoblot analysis to detect 130 kDa ROR1 protein. (B) Results of screening hybridoma clones by immunoblot analysis for production of antibodies that would be capable of binding only full-length ROR1 expressed in CLL cells. Clones that produce anti-ROR1 antibodies were detected by the presence of a 130 kDa band in a CLL cell lysate. Anti-ROR1 monoclonal antibody clone 6D4 (lane indicated by the arrow) shows a strong 130 kDa band in the CLL cell lysate. Clone 4A11 also shows a strong 130 kDa band.
Figure 6B:
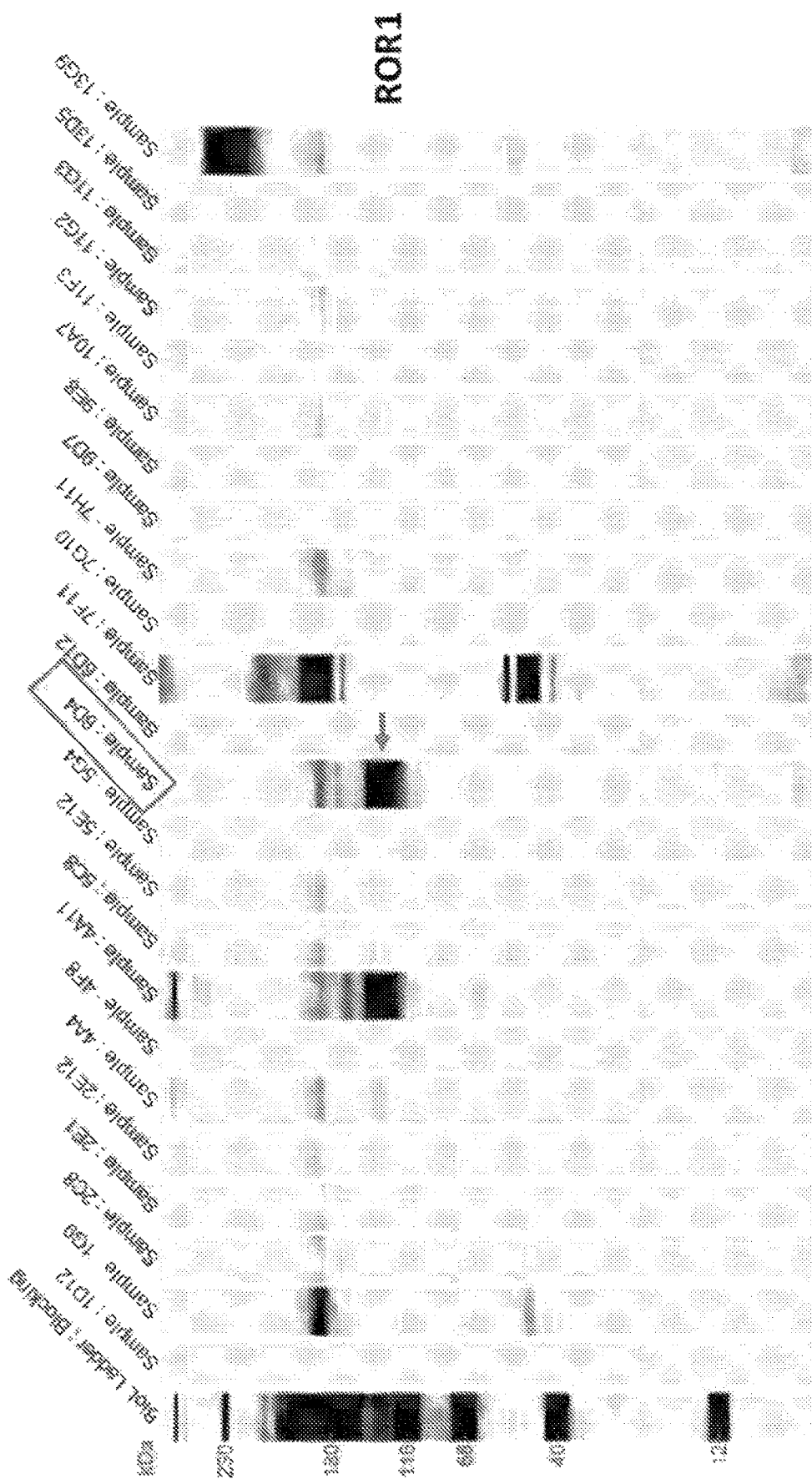

Supernatants from the top 133 hybridoma clones were screened using immunoblot and immunohistochemistry (IHC) analysis. Immunoblot analysis was used in the initial screening of supernatants for antibodies specific for ROR1. Total cell lysates were prepared using lysis buffer [10 mM Tris-HCl (pH 8.0), 130 mM NaCl, 1% (v/v) Triton X-100, 5 mM EDTA, and protease inhibitor cocktail (Roche)]. The cell pellets were resuspended in lysis buffer at 1×10⁷ cells/ml and incubated for 10 minutes on ice, followed by centrifugation at 13,000 rpm and 4° C. for 15 minutes. The protein concentration in the supernatant was determined using the BCA Protein Assay kit (Thermo Scientific Pierce). Cell lysates from CLL cells were run on the WES immunoblot system (Altogen Labs, Austin, TX) using standard protocols, and visualized with anti-mouse HRP. Polyclonal sera from immunized mice were screened by immunoblot against lysates from primary CLL cells (ROR1⁺) and ROR1⁻ K562 cells, to identify sera that detected a 130 kDa band corresponding to full-length ROR1 (FIG. 6A). Several clones that recognized the 130 kDa ROR1 band (ROR1_v1) in lysates of CLL cells were identified (FIG. 6B). Clone 6D4 specifically detected a clear 130 kDa ROR1 band by immunoblotting (FIG. 6B). Hybridoma 6D4 underwent two subsequent rounds of subcloning with repeated validation for peptide binding.

Clones that detected ROR1_v1 were then tested against a panel of different FFPE tissues (K562/ROR1⁺ cell lines, K562 cells, CLL lymph nodes, and multiple normal tonsil tissues) by IHC analysis. Four-micron sections of tissue were cut and stained with the Leica Bond Rx (Leica Biosystems, Buffalo Grove, IL). Slides were pretreated with H2 buffer for 20 minutes. Endogenous peroxidase was blocked with 3% hydrogen peroxide for 5 minutes. A protein block was applied for 10 minutes (15% goat serum, 5% human serum in antibody diluent). For mouse anti-ROR1 6D4 monoclonal antibody, the antibody was used at a 1:50 dilution and applied to the tissue for 30 minutes, and any bound 6D4 antibody was then detected using Leica PowerVision HRP mouse-specific polymer (PV6110) for 12 minutes and staining was visualized with Refine DAB (Leica Biosystems) and a hematoxylin counterstain. Isotype control (IgG) slides were included for each run (Jackson ImmunoResearch Laboratories). Specific binding was indicated by the brown color of the DAB substrate.

Figure 7:
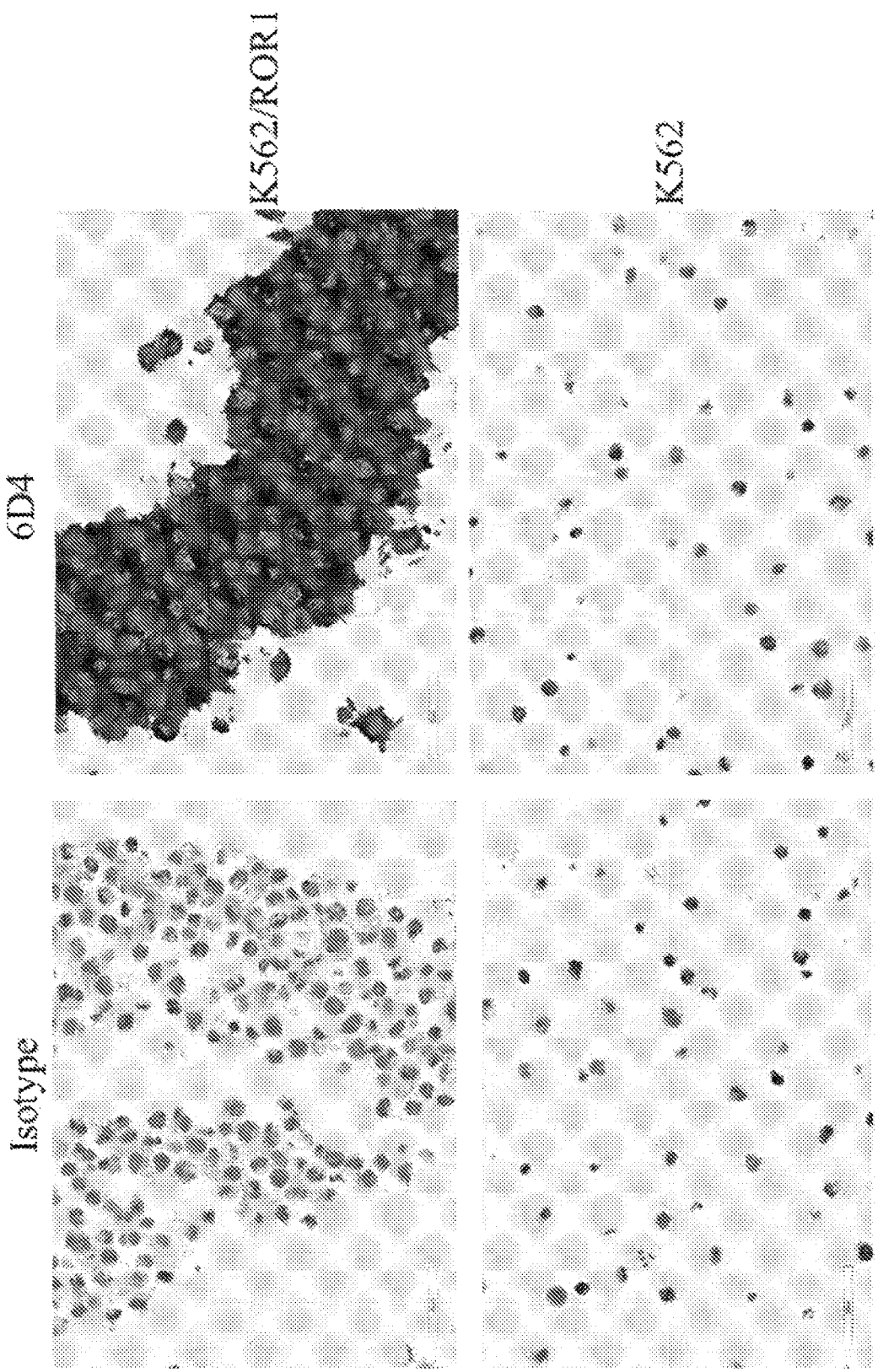
FIG. 7 shows the results of testing anti-ROR1 monoclonal antibody 6D4 for ROR1 specificity by IHC, using full-length ROR1 overexpressing cells (K562/ROR1$^+$ cells) and cells that do not express ROR1 (K562 cells, referred to as ROR1$^-$). Antibody 6D4 showed clear, high cell surface staining of overexpressed full-length ROR1 in K562/ROR1$^+$ cells with minimal background staining in K562 cells (ROR1$^-$).
Figure 8:
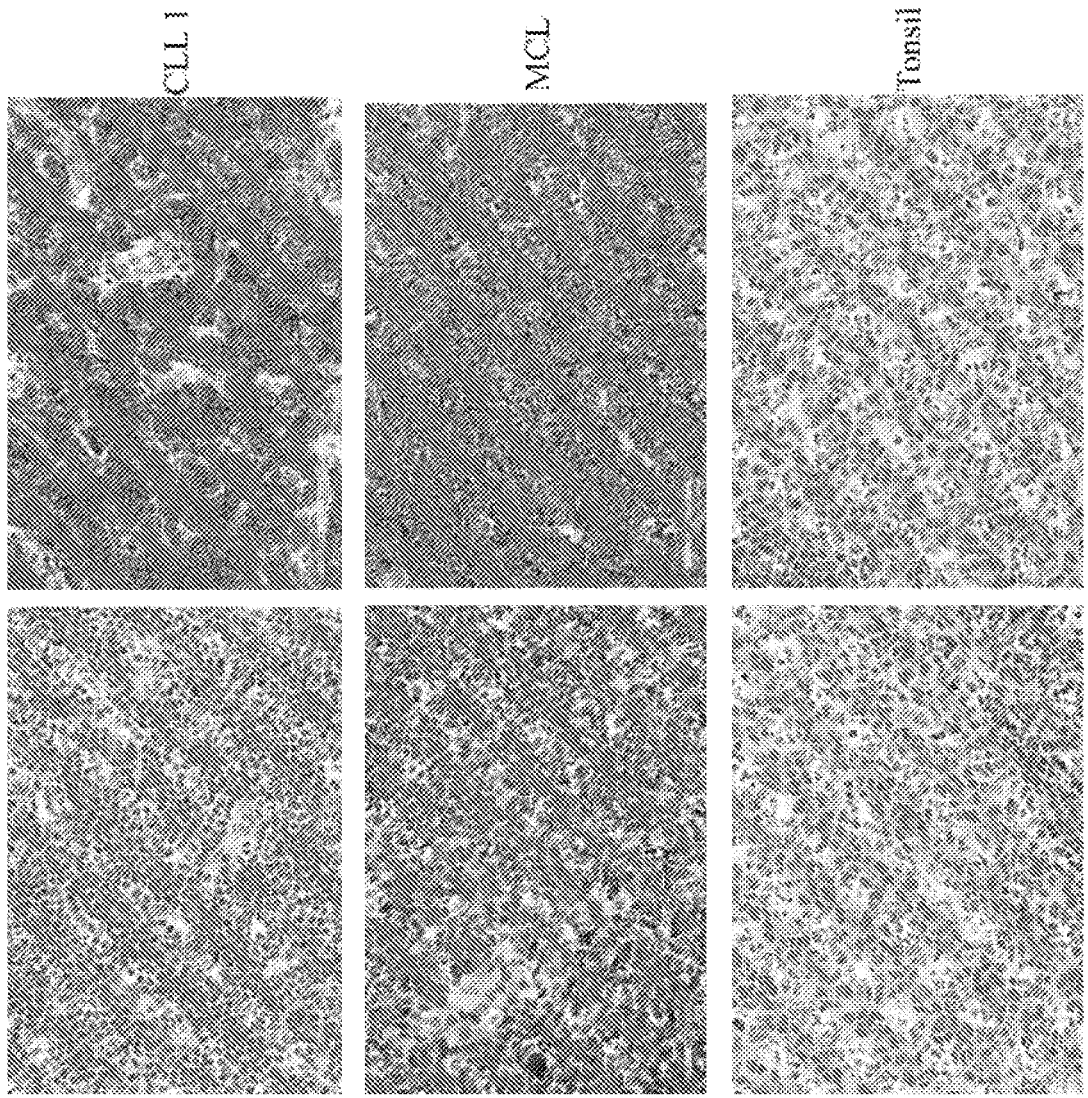
FIG. 8 shows the results of testing anti-ROR1 monoclonal antibody 6D4 (right panels) on ROR1+ (CLL and MCL lymph nodes) and ROR1− (tonsil) tissues by IHC. Antibody 6D4 showed clear cell surface staining of endogenous full-length ROR1 in CLL and MCL tumor lymph nodes, which was not detectable in normal tonsil tissue.

Purified monoclonal antibody from clone 6D4 was tested against FFPE specimens of the following cell types: (1) K562 cells (ROR⁻); and (2) K562 cells transfected to overexpress full-length ROR1 (K562/ROR1⁺). Anti-ROR1 monoclonal antibody 6D4 demonstrated clear membrane staining at high levels against K562/ROR1⁺ and no background staining in ROR1⁻ K562 cells (FIG. 7). The anti-human ROR1 6D4 antibody was also tested against a panel of primary human CLL and MCL tumor lymph nodes to determine whether it could detect endogenous full-length ROR1 expression, with normal human tonsil tissue (ROR1⁻) as a negative control. Anti-ROR1 monoclonal 6D4 demonstrated clear specific membrane staining in CLL and MCL tumor cells with no background staining on normal tonsil tissue (FIG. 8). These results demonstrate that in addition to detecting ROR1 overexpression in transfected cells, purified monoclonal anti-ROR1 6D4 antibody is able to sensitively detect endogenously expressed ROR1 in at least two different tumor types.

Figure 9A:
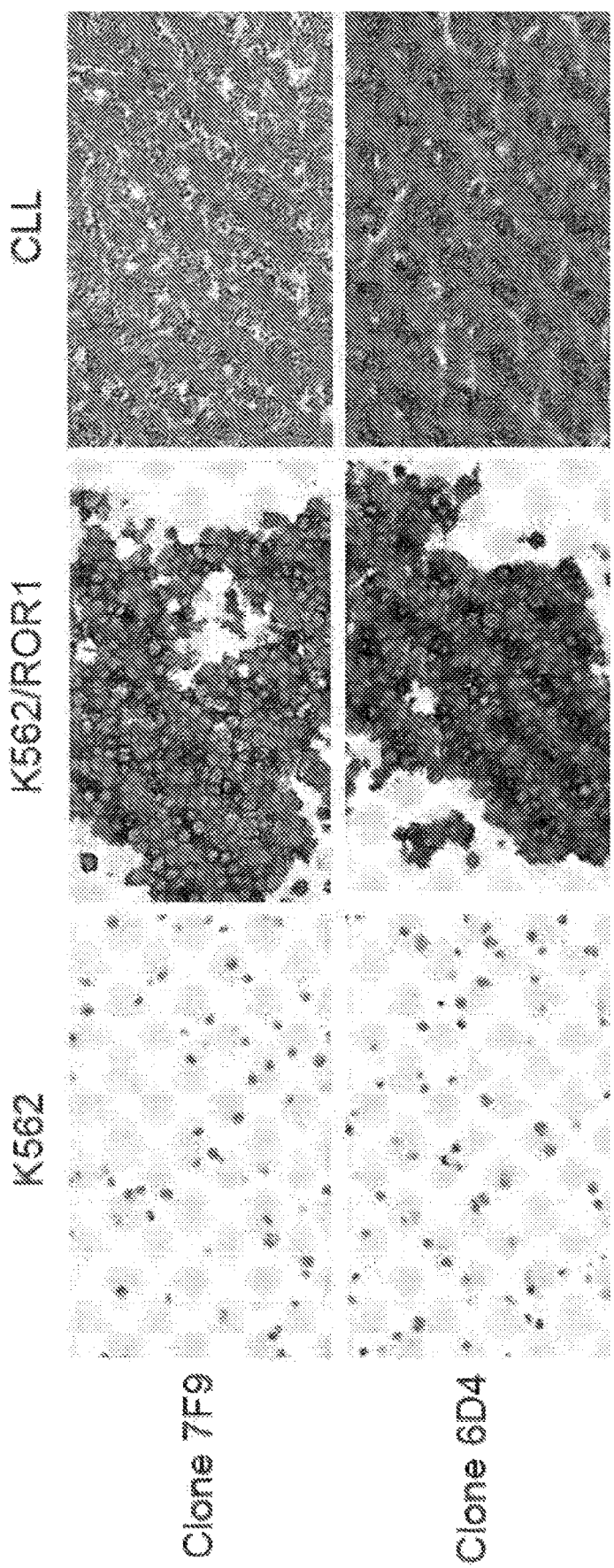
FIGS. 9A and 9B shows IHC staining of FFPE cells for the monoclonal antibody (mAb) 6D4 compared to monoclonal antibodies derived from other clones. (A) Representative clones from IHC screening of concentrated hybridoma supernatants against control K562 cells, ROR1-transfected K562 cells, and CLL lymph nodes. (B) Paired IHC staining of FFPE processed CLL PBMC (n=2) with 6D4 mAb and flow cytometry staining with anti-ROR1 mAb 2A2.
Figure 9B:
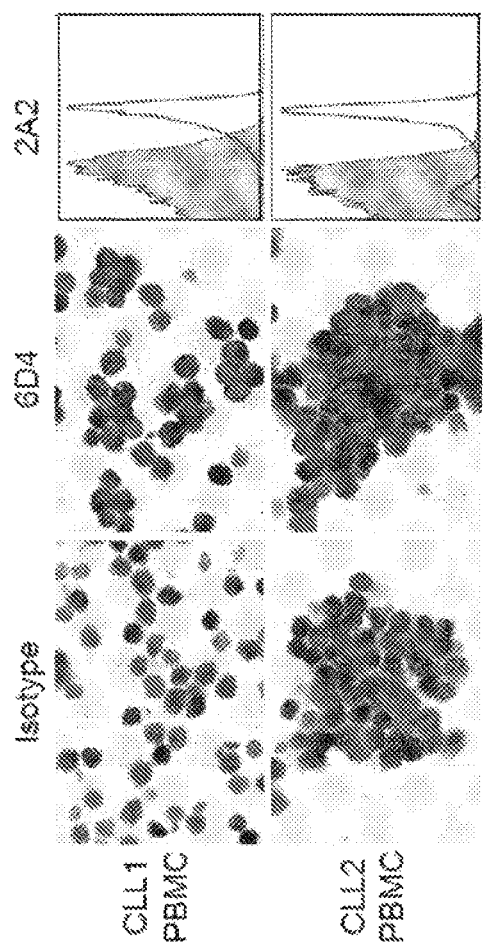

In contrast, supernatants from many other clones stained K562 cells that overexpressed ROR1 but failed to detect endogenous ROR1 in FFPE CLL lymph node (FIGS. 9A and 9B).

From the mixture of four different ROR1 peptides that was used to immunize mice, one ROR1 peptide fragment was specifically bound by anti-ROR1 monoclonal antibody clone 6D4. Anti-ROR1 monoclonal antibody 6D4 was found to bind to an epitope within the human ROR1 peptide 786-NPRYPNYMFPSQGITPQGQIAGFIGPPIP-814 (SEQ ID NO.:3), which is located in the C-terminal region of full-length ROR1 (ROR1_v1) (see FIG. 5). The epitope was mapped using a cytometric bead array (CBA) for secondary target deconvolution (BD™ Elispot, San Jose, CA).

Taken together, these studies demonstrate that anti-ROR1 monoclonal antibody 6D4 can specifically and sensitively detect full-length ROR1 expressed endogenously in human cells and tissues, such as in cancer.

Example 4

Validating Specificity of Monoclonal Antibody 6D4

Purified 6D4 monoclonal antibody was further evaluated for binding to ROR1 and ROR2. Briefly, nucleic acid molecules encoding human ROR1_v1 (NP_005003.2), and ROR2 (pDOMR223-ROR2-Addgene) were cloned into a retroviral vector as described by Leisegang et al. (*J. Mol. Med.* 86:573, 2008). Cell lines K562, JeKo-1, MDA-MB-231, NCI-H1975, and 293T were obtained from ATCC. K562 cells were transduced with retroviral vectors expressing human ROR1_v1, human ROR2 (SEQ ID NO.:56), and rhesus ROR1_v1 (SEQ ID NO.: 58) peptides. Flow staining was performed with anti-ROR1 (Clone 2A2-Miltenyi) and anti-ROR2 (R&D Biosystems-FAB20641G) or isotypes as previously described (see Berger et al., *Cancer Immunol. Res.* 3:206, 2015).

Figure 10A:
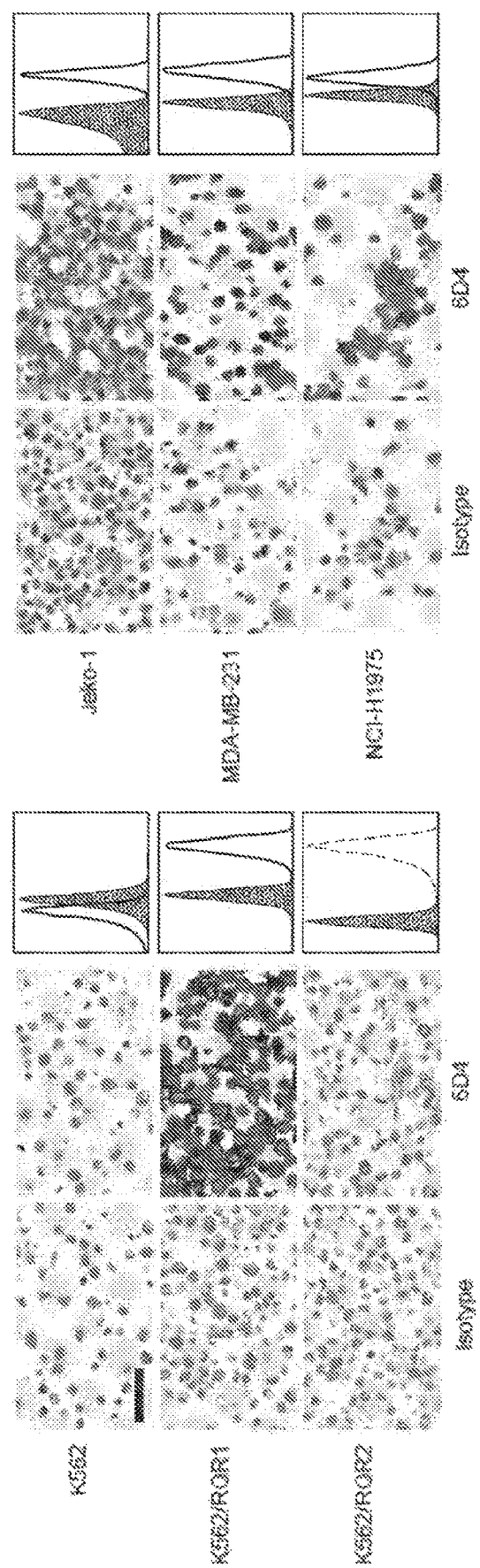
FIGS. 10A through 10C further illustrate IHC staining of FFPE cells by mAb 6D4 and isotype, and immunoblot analysis of cell lysates for ROR1 expression. (A) IHC staining of FFPE ROR1-transfected and control cell lines (left panels), and ROR1+ tumor cell lines (right panels), with 6D4 mAb. Scale bar represents 50 μm. Paired flow cytometry staining with anti-ROR1 6D4 mAb (solid line), anti-ROR2 (R&D Biosystems-FAB20641G) (dashed line), and isotype (shaded grey) antibodies. (B) Staining of FFPE tonsil tissue and CLL and MCL lymph nodes by 6D4 mAb relative to isotype. (C) Immunoblot analysis of ROR1− and ROR1+ cell lines with the 6D4 mAb. Full-length ROR1 is expressed as a 130 kDa protein.
Figure 10B:
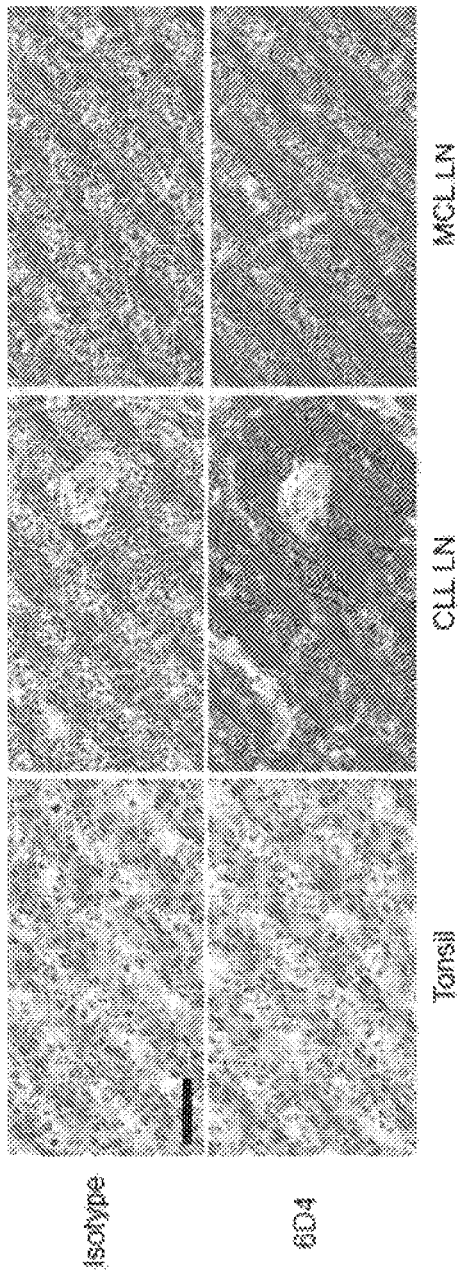
Figure 10C:
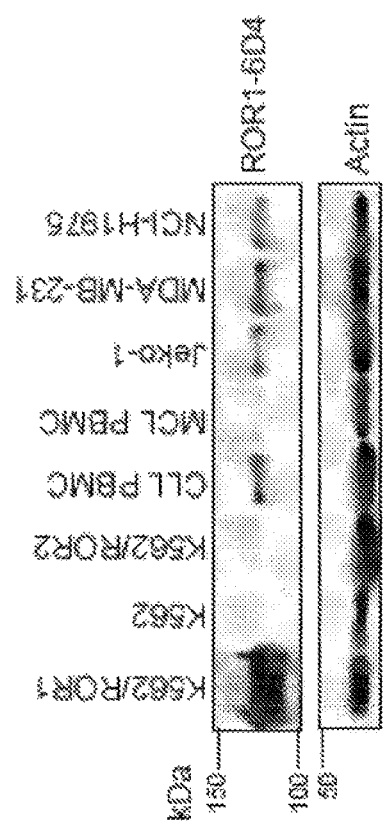

Antibody 6D4 stained K562/ROR1 with minimal background against untransduced K562 cells or K562 expressing human ROR2, and stained hematopoietic and epithelial tumor cell lines, including JeKo-1, MDA-MB-231, and NCI-H1975, which also show cell-surface ROR1 staining by flow cytometry using the well-characterized clone 2A2 (FIG. 10A). No staining was observed in K562 cells expressing human ROR2 (FIG. 10A, bottom left). Purified 6D4 was also tested for staining CLL and MCL lymph nodes and PBMC, and uniform membrane staining with minimal background on normal human tonsil was observed (FIG. 10B). Immunoblot of lysates from K562/ROR1, primary CLL and MCL cells, and ROR1⁺ tumor lines with 6D4 detected a 130 kDa band consistent with full-length ROR1 (FIG. 10C).

These results demonstrate that the 6D4 monoclonal antibody specifically detects endogenous cell-surface expression of full-length ROR1 on primary tumors with greater sensitivity than previous reagents and without cross-reactivity against ROR2.

Example 5

Use of Anti-ROR1 Monoclonal Antibody 6D4 to Identify Solid Tumors Expressing ROR1

To determine whether anti-ROR1 monoclonal antibody 6D4 could detect endogenous ROR1 in tissues such as diseased tissues, such as ROR1 cell surface expression in solid tumors, purified anti-ROR1 monoclonal antibody 6D4 was used in immunohistochemistry (IHC) assays on formalin-fixed-paraffin-embedded (FFPE) samples of breast cancer, lung cancer, ovarian cancer, and pancreatic cancer.

Figure 11:
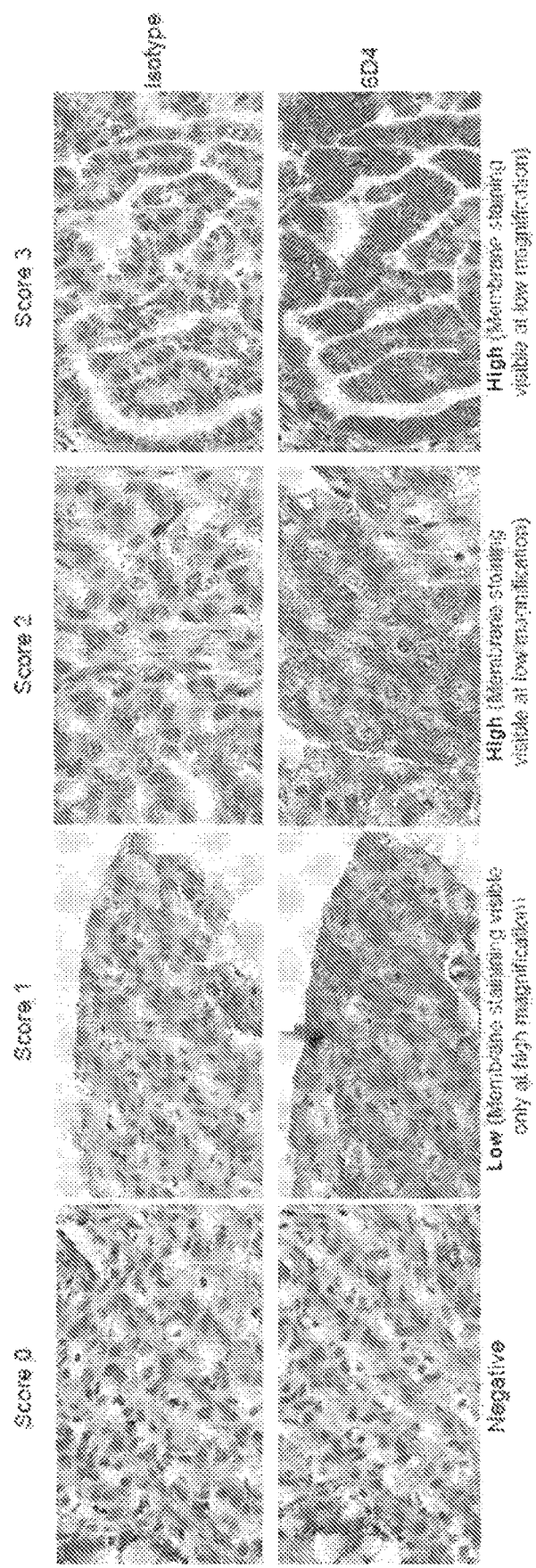
FIG. 11 shows representative images of IHC scoring of ROR1+ tumors. 'Score 0' indicates absent staining. 'Score 1' indicates low level staining with membrane staining visible at high magnification. 'Score 2' and 'Score 3' indicate high membrane staining visible at low magnification.

IHC samples were prepared as described above in Example 3. Tumor tissues were scored for cell-surface ROR1 by two independent board certified pathologists and the scores averaged. Tissues were scored as '0-Negative,' '1-Low membrane staining with antibody,' '2 or 3-High membrane staining with antibody' (FIG. 11). Homogenous and focal staining were defined as staining on greater than 50% and less than 30% of tumor cells, respectively.

6D4 Antibody Sensitivity and Specificity For Epithelial Cancer Tumor Cells

Figure 12:
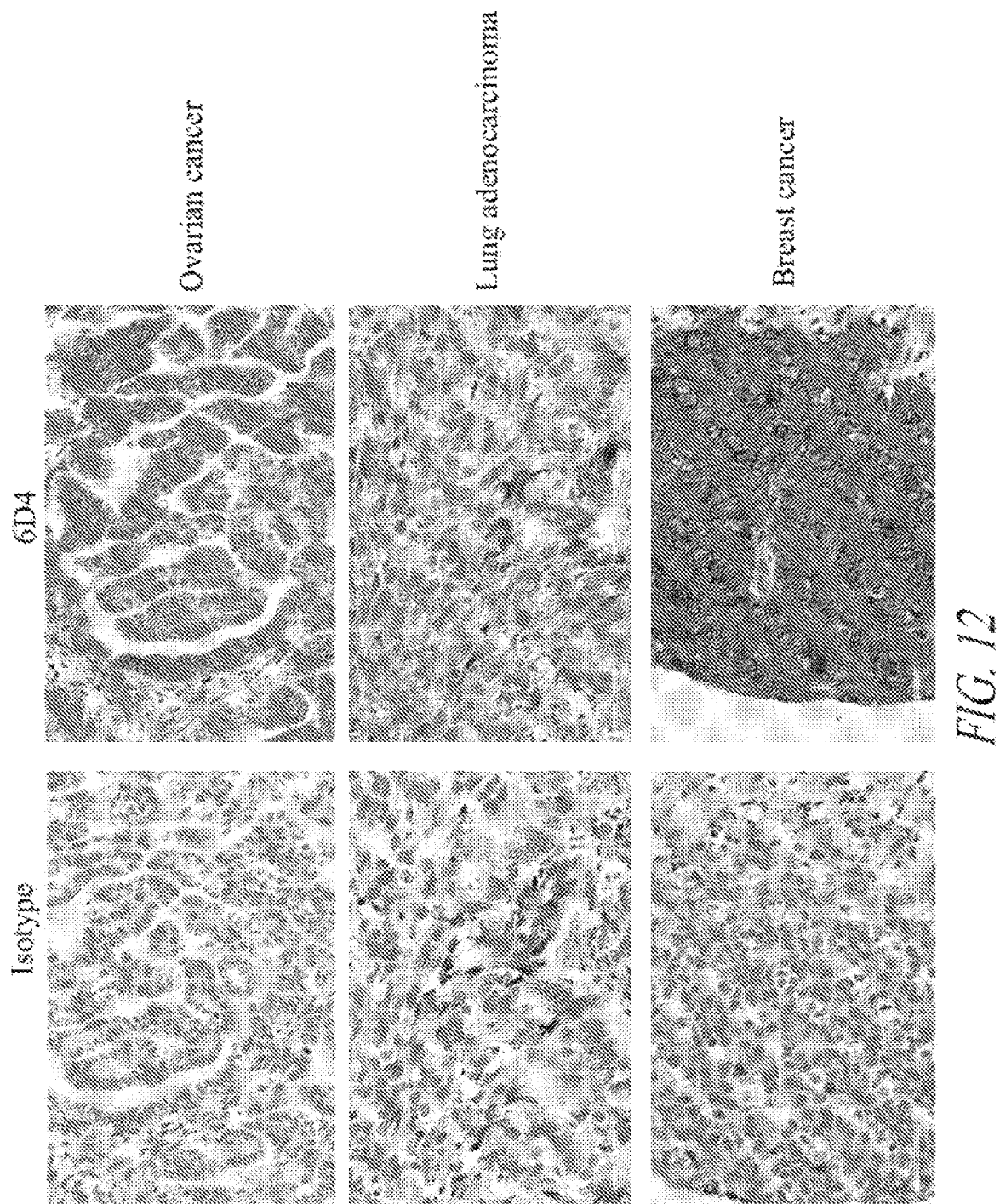
FIG. 12 shows expression of full-length ROR1 in epithelial cancers, as analyzed by IHC with anti-ROR1 monoclonal antibody 6D4. Clear cell surface staining was observed in ovarian cancer, lung adenocarcinomas, and triple-negative breast cancer.
Figure 13:
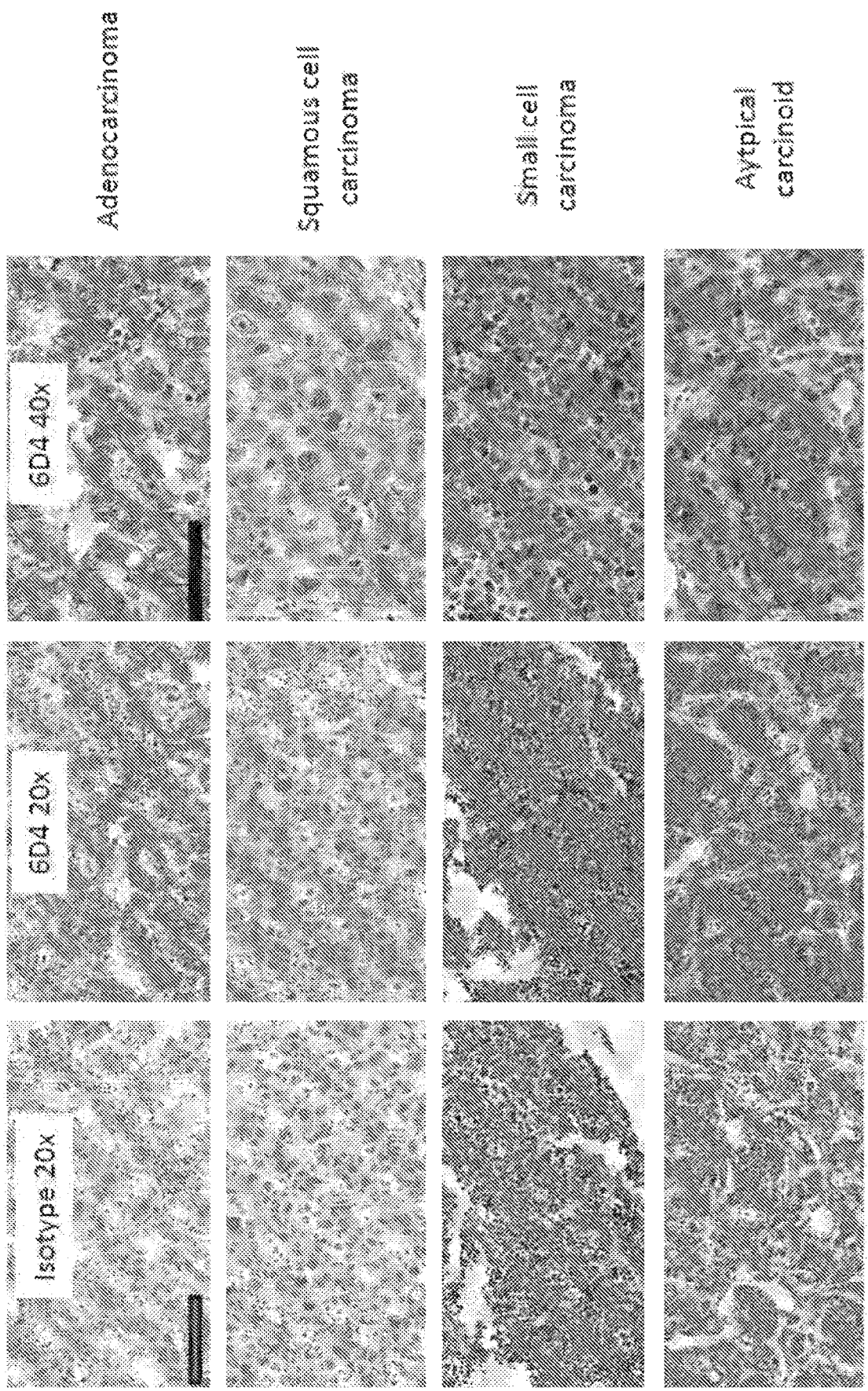
FIG. 13 shows ROR1 expression, as detected by the antibody 6D4, in lung cancer sub-types (adenocarcinoma, squamous cell carcinoma, small cell carcinoma, and atypical carcinoid). ROR1 staining was observed with this antibody in each of these cancer types, as compared to staining with the isotype control antibody.
Figure 14:
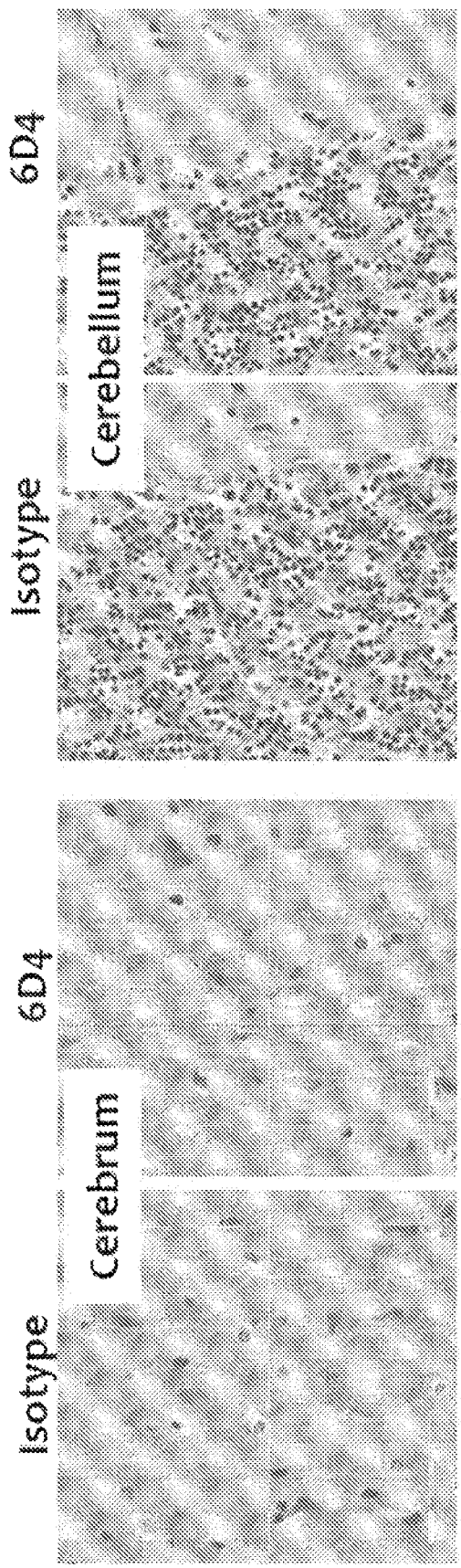
FIG. 14 shows results of staining using the antibody 6D4 and an isotype control on tissue sections derived from vital normal human tissues.
Figure 14:
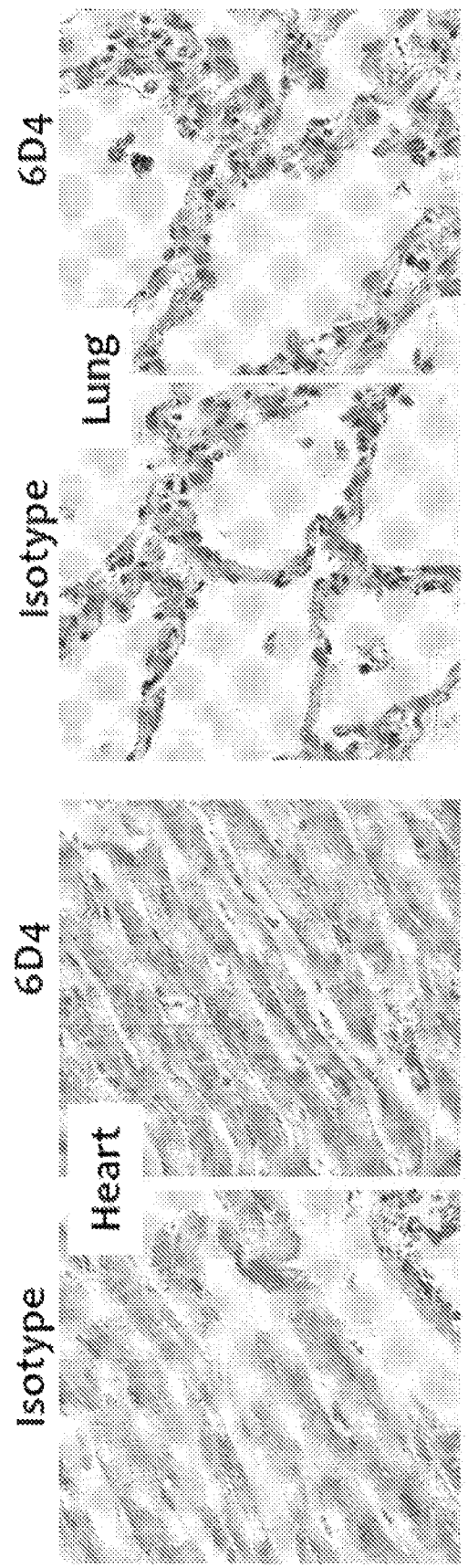
Figure 15:
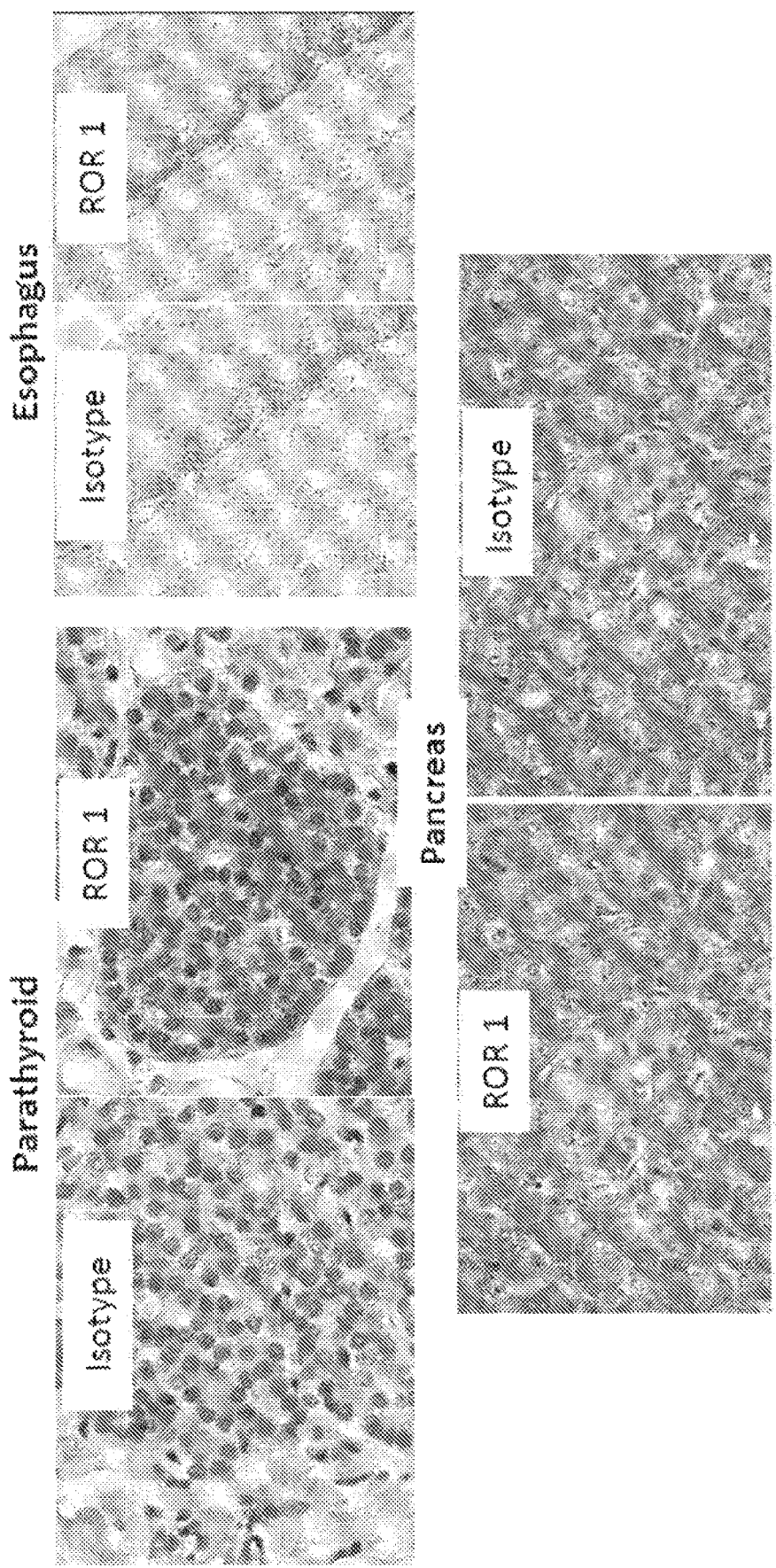
FIG. 15 shows expression of ROR1 on a subset of normal human tissues (parathyroid, esophagus, pancreas) as detected using the antibody 6D4.

In a first study, anti-ROR1 monoclonal antibody 6D4 was found to be capable of sensitively and specifically binding to tumor cells expressing full-length ROR1, as compared to isotype control. In particular, ROR1 was found to be highly expressed in a subset of patients with triple negative breast cancer, lung adenocarcinoma, and ovarian cancer tissues (FIG. 12). In this study, 50%, 75% and 50% of ovarian cancers, lung adenocarcinomas, and triple negative breast cancers, respectively, were observed to have homogenous ROR1 expression. As shown in FIG. 13, staining also was observed in various lung cancer types, including adenocarcinoma, squamous cell carcinoma, small cell carcinoma, and atypical carcinoid. As shown in FIGS. 14 and 15, the antibody detected low levels of ROR1 in only a subset of normal human tissues (including parathyroid, pancreatic islets, and regions of the esophagus).

ROR1 Expression in Epithelial Cancers a. Ovarian Cancer

In a previously published study, approximately 50% of ovarian cancers were found to express Ror1 transcripts, and patients with tumors that had high Ror1 transcript levels had an unfavorable disease-free and metastases-free survival (Zhang et al., *Scientific Reports* 4:5811, 2014). However, in that study, the IHC analysis of ROR1 localized the staining primarily to the tumor cell cytoplasm and nucleus, which was distinct from the cell-surface expression of full-length ROR1_v1 on tumor cell lines.

Figure 16A:
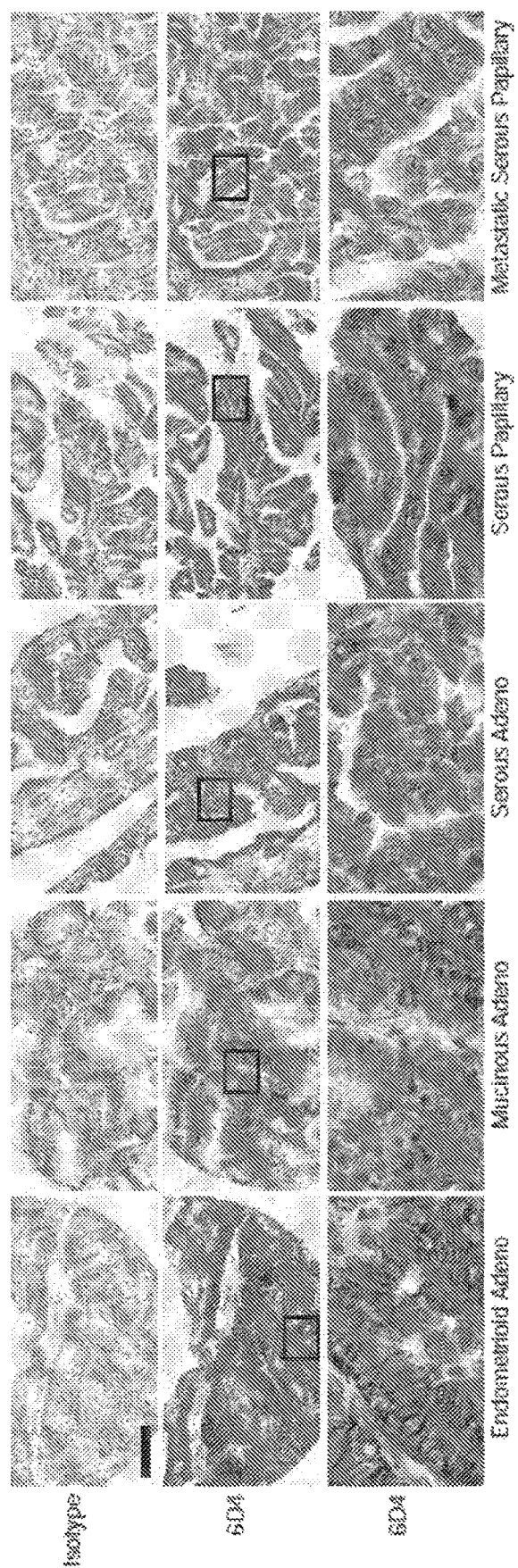
FIGS. 16A through 16C show membrane ROR1 staining in ovarian cancer using the 6D4 mAb. (A) Representative IHC images of subtypes of ovarian cancer samples stained with the 6D4 mAb. Scale bar represents 100 μm. Regions in squares in middle panels are magnified 10× in bottom panels. (B) Percent of ROR1+ tumors in different subtypes of ovarian cancer. (C) Percent of ROR1$^{high}$ and ROR1$^{low}$ tumors in the ROR1+ ovarian cancer subset.
Figure 16B:
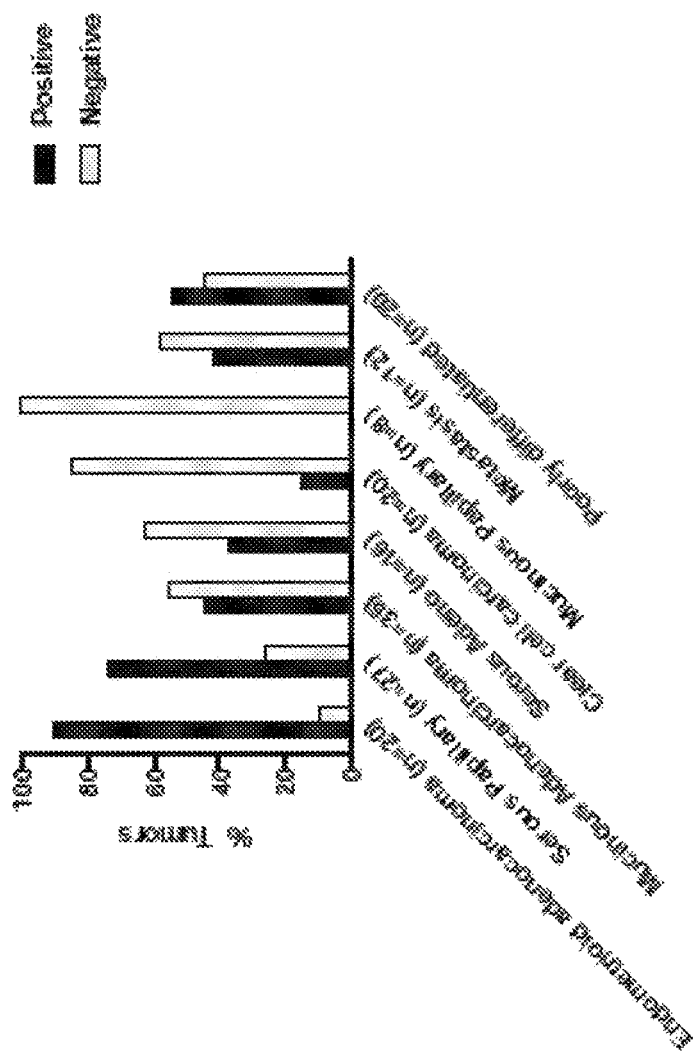
Figure 16C:
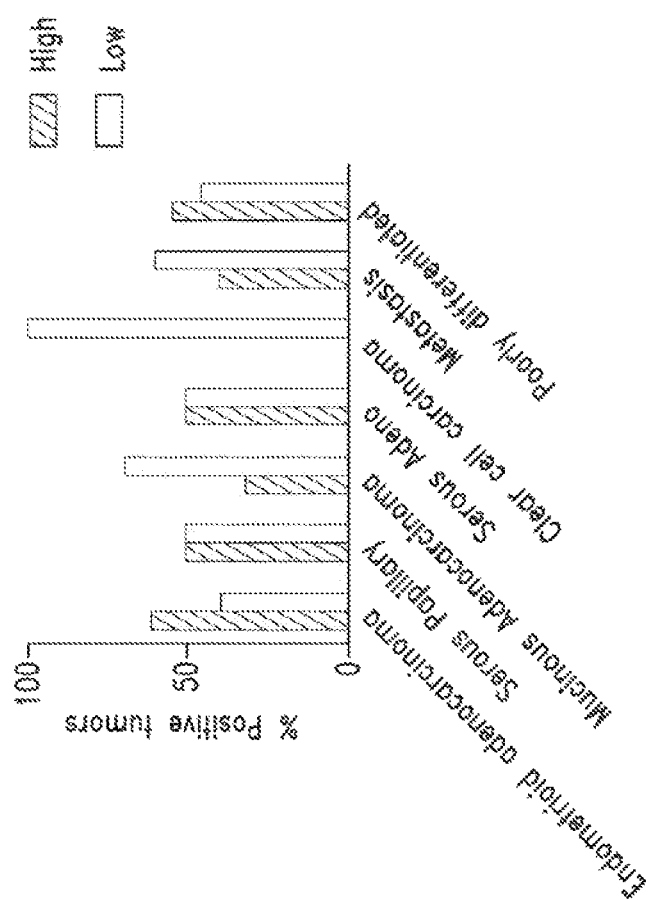

Therefore, two tissue microarrays comprised of 159 ovarian cancers of a variety of histologies were examined using the 6D4 monoclonal antibodies in IHC. Fifty percent (50%) of the ovarian cancers showed predominantly membrane and cytoplasmic staining with 6D4 (FIG. 16A). In 92% of tumors, ROR1 was expressed homogeneously, defined as definite membranous staining of greater than 50% of cells, and the staining intensity in positive tumors could be classified as high or low based on the intensity of cell-surface staining (FIG. 11). When grouped into histologic subtypes, approximately 90% of endometrioid adenocarcinomas were ROR1$^+$ and 60% of positive tumors were ROR1$^{high}$, 74% of serous papillary carcinomas were ROR1$^+$ with 50% graded ROR1$^{high}$, 44% of mucinous adenocarcinomas were ROR1$^+$ (31% ROR1$^{high}$); and 37% of serous adenocarcinomas were ROR1$^+$ (50% ROR1$^{high}$) (FIGS. 16B, 16C). Cell-surface ROR1 was low or absent in certain subtypes of ovarian cancer such as clear cell carcinomas and mucinous papillary adenocarcinoma. A small number of metastatic samples (1 clear cell, 4 serous papillary, and 7 serous adenocarcinomas) were examined and 75% of the metastatic serous papillary and 40% of the serous adenocarcinomas were ROR1$^+$. These results demonstrate that the 6D4 mAb detects cell-surface, full-length ROR1 in a large fraction of ovarian cancers, and may be useful both to determine prognostic implications of ROR1 expression and identify patients eligible for ROR1 targeted therapies.

b. Breast Cancer

ROR1 gene expression was previously examined in breast cancer using publically available GEO datasets, and high ROR1 expression correlated with an epithelial-mesenchymal transition (EMT) gene signature and lower metastasis-free survival (Zhang et al., *PloS One* 7:e31127, 2012; Cui et al., *Cancer Research* 73:3649, 2013). One of these reports observed ROR1 protein expression in 70% of primary cancers by IHC (75% of lobular breast and 70% of ductal breast were ROR1$^+$) although staining with the reagent used in that study was localized to the nucleus and cytoplasm, suggesting the protein detected may not be the cell-surface, full-length variant of ROR1 (Zhang et al., 2012). An independent group examined ROR1 by IHC in triple negative breast cancer (TNBC) and found that 22% were ROR1$^+$ and these patients had a shorter disease-free survival (Chien et al., *Virchows Archiv* 468:589, 2016)

Figure 17A:
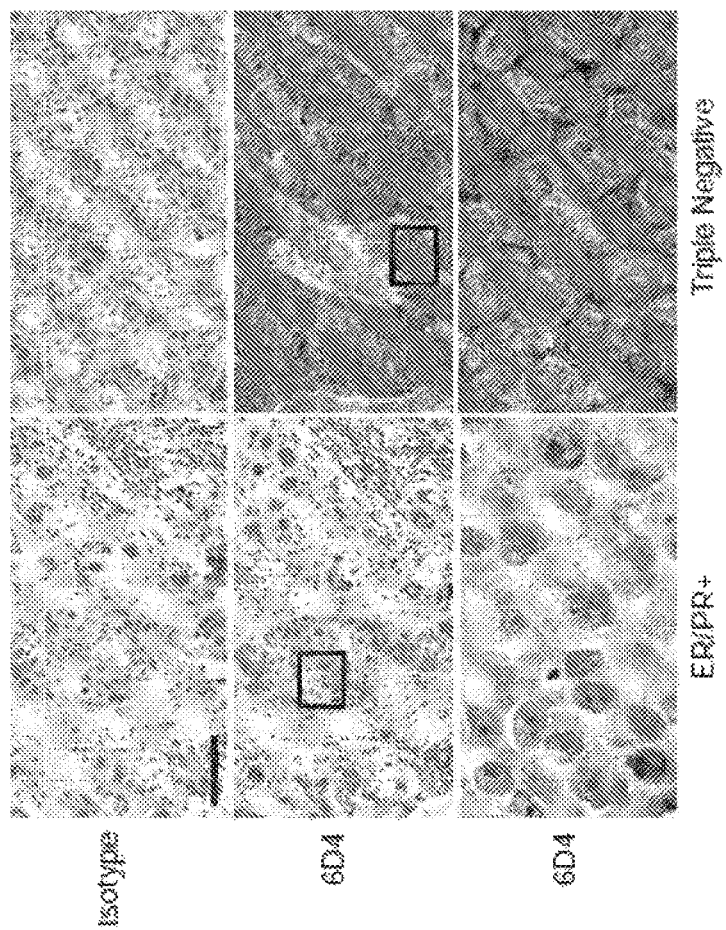
FIGS. 17A through 17C show membrane ROR1 staining in breast cancer using the 6D4 mAb. (A) Representative IHC images of subtypes of breast cancer tissue samples stained with the 6D4 mAb. Scale bar represents 100 μm. Regions in squares in middle panels are magnified 10× in bottom panels. (B) Percent of ROR1+ tumors in different subtypes of breast cancer. (C) Percent of ROR1$^{high}$ and ROR1$^{low}$ tumors in the ROR1+ breast cancer subset.
Figure 17B:
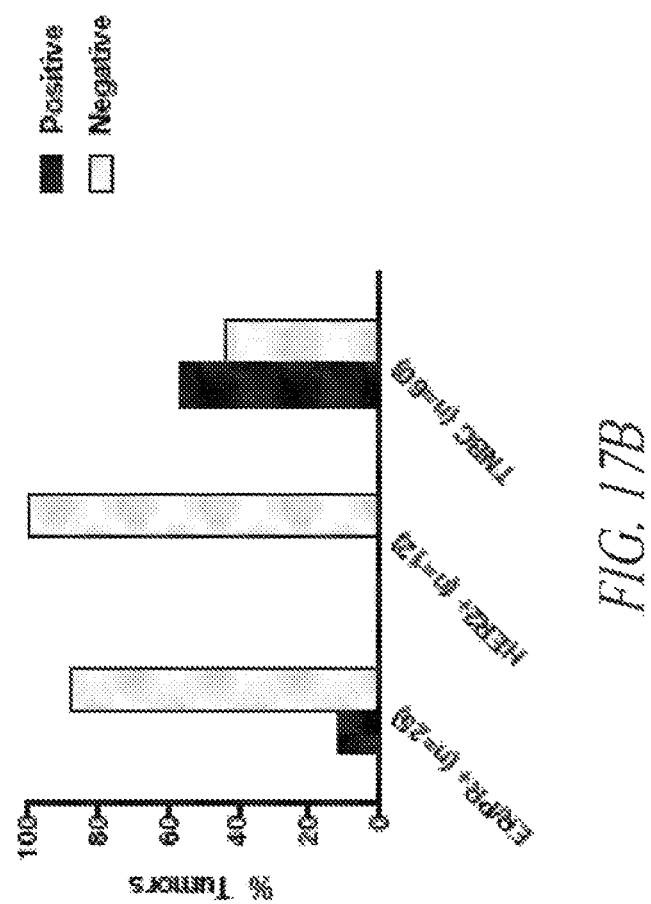
Figure 17C:
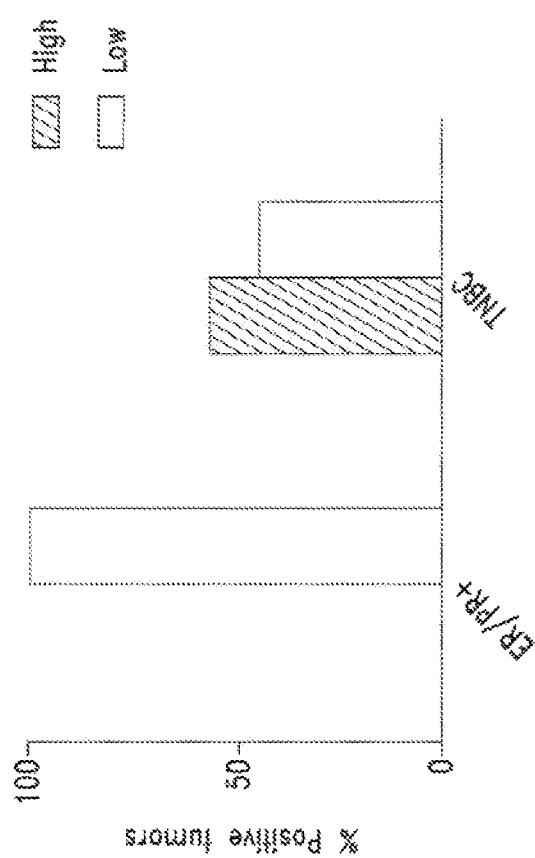

In this study, 24 ER/PR$^+$, 12 Her2$^+$ and 60 TNBC samples were analyzed for ROR1 using the 6D4 mAb (FIGS. 17A-17C). Low ROR1 staining was observed in a small percentage of the ER/PR$^+$ (12% ROR1$^+$) and no ROR1 expression was observed in HER2$^+$ tumors. However, ROR1 was highly expressed in TNBC, where 57% of samples were ROR1$^+$ with 56% graded as ROR1$^{high}$ and 74% showing homogenous staining (FIGS. 17B-17C).

c. Lung Cancer

In earlier studies, Ror1 transcripts were identified in non-small cell lung cancer by microarray and PCR (Yamaguchi et al., *Cancer Cell* 21:348, 2012; Karachaliou et al., *Translational Lung Cancer Research* 3:122, 2014). IHC with different polyclonal and monoclonal antibodies showed ROR1 staining in 24-90% of lung adenocarcinomas, which constitute 40% of all lung cancers (Zhang et al., *The American Journal of Pathology* 181:1903, 2012; Yamaguchi et al., *Cancer Cell* 21:348, 2012; Liu et al., *PloS One* 10:e0127092, 2015). ROR1 expression in other lung cancer subtypes has not been well characterized.

Figure 18A:
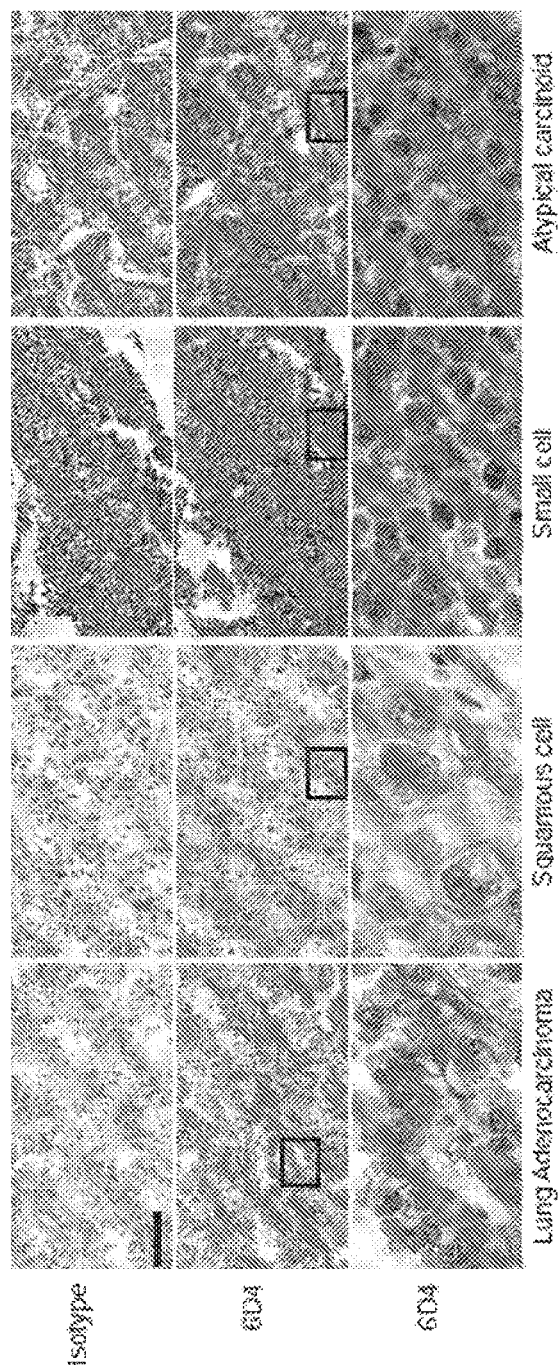
FIGS. 18A through 18D show membrane ROR1 staining in lung cancer using the 6D4 mAb. (A) Representative IHC images of ROR1 expression in subtypes of lung cancer samples stained with the 6D4 mAb. Scale bar represents 100 μm. Regions in squares in middle panels are magnified 10× in bottom panels. (B) Percent of ROR1+ tumors in different subtypes of lung cancer. (C) Percent of ROR1$^{high}$ and ROR1$^{low}$ tumors in the ROR1+ lung cancer subset. (D) Representative IHC images of ROR1 expression in primary and matched metastatic lymph nodes of ROR1+ lung adenocarcinomas. Scale bar represents 50 μm.
Figure 18B:
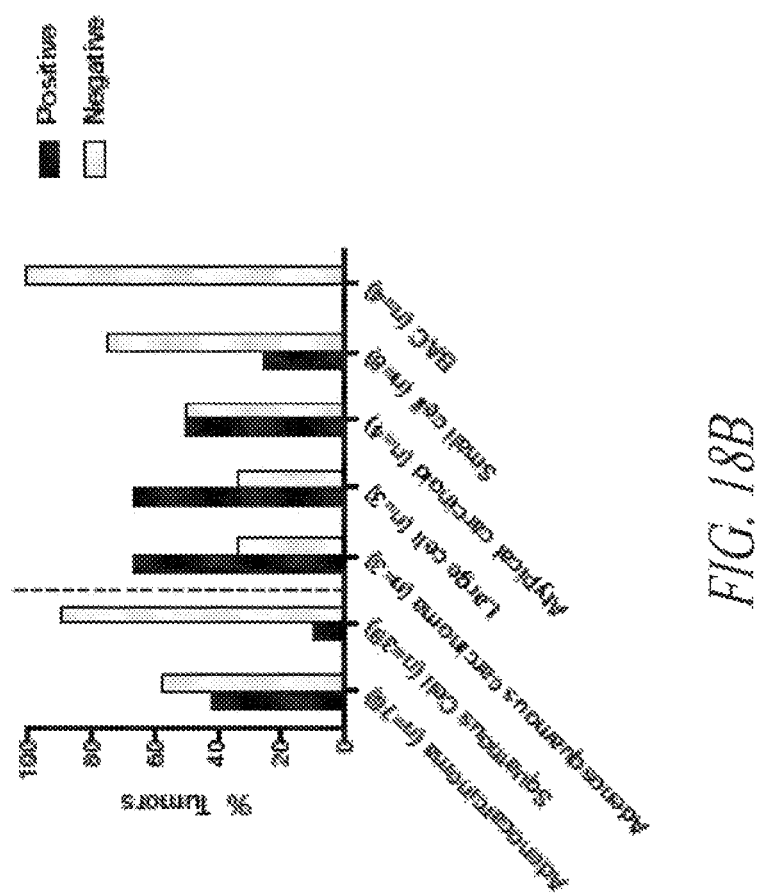
Figure 18C:
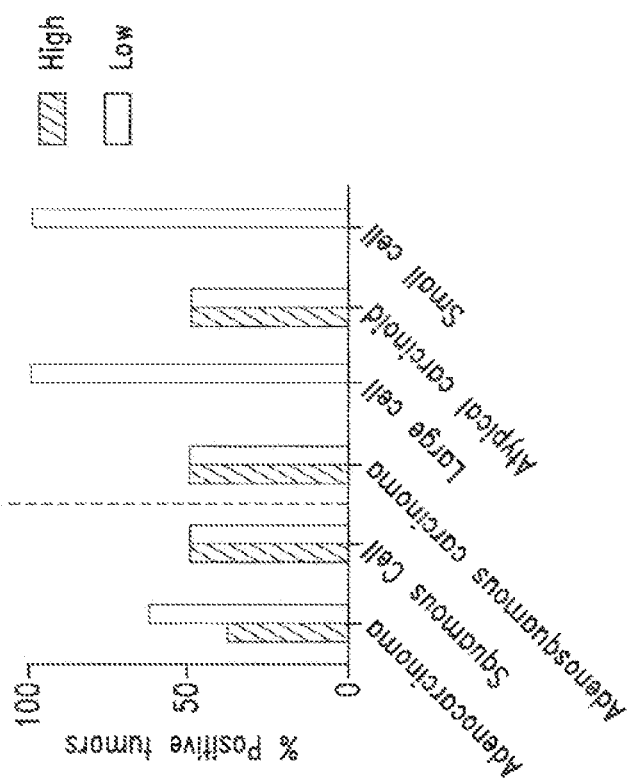

ROR1 expression was examined in 137 primary lung cancers of different histologic types using the 6D4 mAb. ROR1 expression was most frequent in lung adenocarcinomas (42% were ROR1$^+$ with 38% graded ROR1$^{high}$) with a minority (12%) of squamous cell carcinomas staining ROR1$^+$ (FIGS. 18A-18C). We also observed ROR1 staining in adenosquamous carcinomas, large cell carcinomas, small cell carcinomas, and atypical carcinoid tumors, although too few of these tumors were examined for an accurate estimate of the frequency of positivity (FIGS. 18B-18C). All ROR1$^+$ lung tumors exhibited homogeneous staining.

Figure 18D:
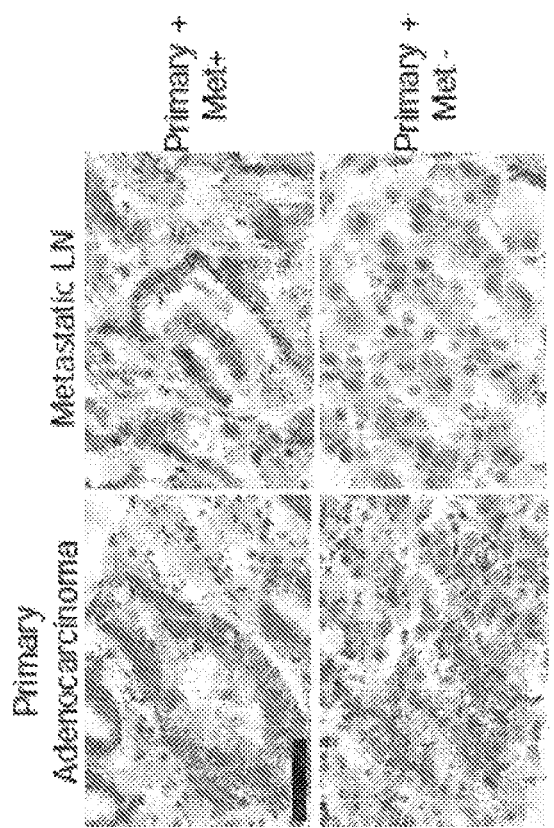

Because ROR1 has been reported to play a role in EMT and tumor migration, we ROR1 expression in matched metastatic lesions was evaluated to determine whether ROR1 expression in primary tumors was maintained. ROR1 expression was examined in 30 primary and matched metastatic lymph nodes from patients with lung adenocarcinoma, 50% of whom had ROR1$^+$ tumors. In patients with ROR1$^+$ primary tumors, 60% of the matched metastatic lymph nodes remained ROR1$^+$, and 40% were ROR1$^-$ (FIG. 18D). In two patients, the primary tumor was ROR1$^-$ but the metastatic lymph nodes were ROR1$^+$. These results suggest that there may not be a direct correlation between increased ROR1 expression and metastatic potential in lung adenocarcinomas, or that maintenance of ROR1 expression may not be required for tumor growth at a distant metastatic site.

d. Pancreatic Cancer

Pancreatic adenocarcinoma has been previously reported in one study to frequently (83%) express ROR1 (Zhang et al., *The American Journal of Pathology* 181:1903, 2012).

Figure 19A:
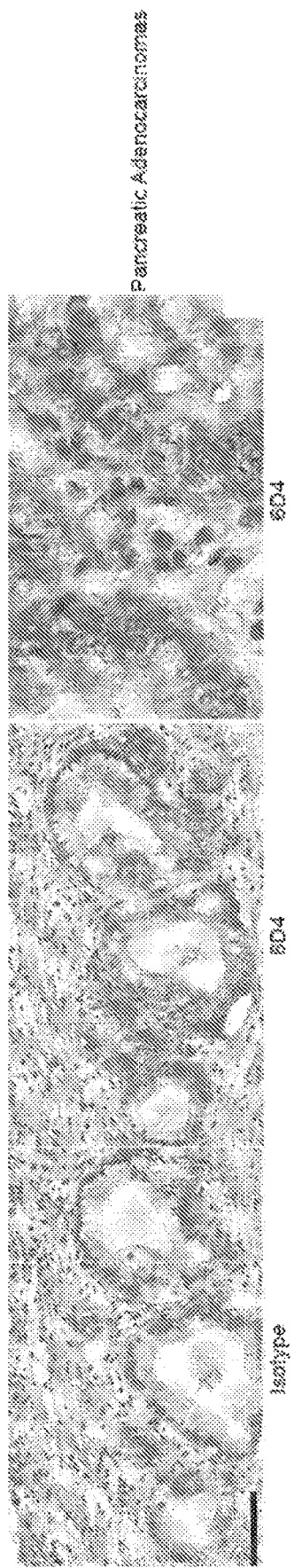
FIGS. 19A and 19B show ROR1 expression in pancreatic adenocarcinomas using mAb 6D4. (a) Representative IHC images of ROR1 staining in pancreatic adenocarcinoma. Scale bar represents 100 μm. The panel on the far right is a magnified image of the middle panel. (B) Percent of ROR1+ tumors in pancreatic adenocarcinomas.
Figure 19B:
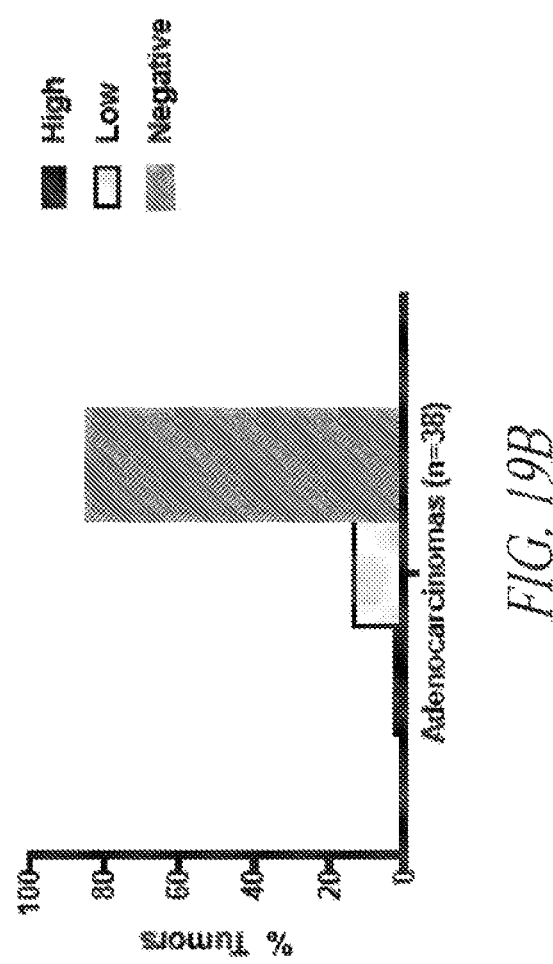

Cell-surface ROR1 expression was determined in 38 cases of pancreatic adenocarcinoma using the 6D4 mAb (FIG. 19A). Surprisingly, we found ROR1 expressed at low levels in a small fraction of tumors (15%) (FIG. 19B).

Summary

Overall, the present analysis of common epithelial cancers shows that high levels of cell-surface-expressed, full-length ROR1 are present in a significant fraction of ovarian cancers, TNBC, and lung adenocarcinomas. ROR1 staining is typically homogeneous, suggesting that the vast majority of such tumor cells may be susceptible to ROR1-targeted therapies.

These results support the utility of ROR1 as a tumor-associated antigen target, to be targeted with ROR1-specific therapies, such as immunotherapies, including immune cells expressing anti-ROR1 chimeric antigen receptors (CAR) on their cell surfaces, including in hematologic or solid tumors expressing ROR1 on their surfaces. Moreover, anti-ROR1 monoclonal antibody 6D4 is useful as a sensitive and specific diagnostic reagent or as a companion diagnostic for ROR1 specific therapies.

Example 6

ROR1 Expression in Normal Rhesus and Human Tissues

Human

A concern for antibody or adoptive T cell therapies targeting ROR1 is the potential for on-target, off-tumor toxicities due to expression of ROR1 on normal tissues (Morgan et al., *Molecular Therapy* 18:843, 2010; Lamers et al., *Molecular Therapy* 21:904, 2013; Hassan et al., *Clinical Cancer Research* 13:5144, 2007). Prior studies that have analyzed ROR1 expression in normal tissues by real time PCR or immunoblot of whole tissue lysates found that ROR1 is absent or expressed at low levels in most normal tissues (Baskar et al., *Clinical Cancer Research* 14:396, 2008; Hudecek et al., *Blood* 116:4532, 2010; Dave et al., *PloS One* 7:e52655, 2012; Fukuda et al., *PNAS* 105:3047, 2008). Whole tissue cDNA pools or lysates are an important first step in detecting ROR1, but can fail to detect expression if it is localized to a minority of cells or a region of the tissue. Flow cytometry has been used to show that cell-surface-expressed, full-length ROR1 is present on adipocytes differentiated from adipocyte precursors in vitro, and at an early stage of normal B cell differentiation in the bone marrow (Hudecek et al., 2010). Several studies have examined ROR1 expression in normal tissues using IHC with previously available antibody reagents but have not reported cell-surface-expressed ROR1 in normal tissues, except for adipocytes (Dave et al., 2012; Choi et al., *Clinical Lymphoma, Myeloma & Leukemia* 15 Suppl: S167, 2015).

Figure 20A:
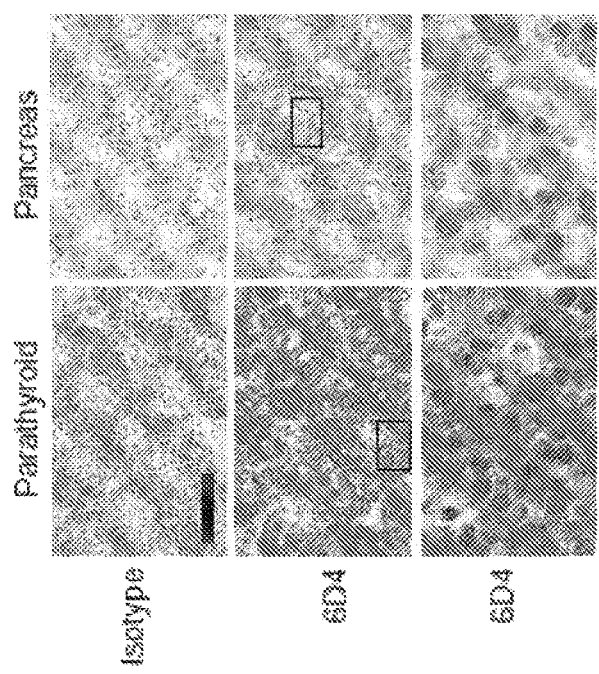
FIGS. 20A through 20F show ROR1 expression in normal human tissues as indicated by IHC staining with mAb 6D4, followed by immunoblot validation. (A) Membrane ROR1 staining in human parathyroid and pancreatic islets with the 6D4 mAb. Scale bar represents 100 μm. Regions in squares in middle panels are magnified 10× in bottom panels. (B) ROR1 expression in different regions of the human gastrointestinal tract. Scale bar represents 100 μm. Regions in squares in middle panels are magnified 10× in bottom panels. (C) ROR1 staining is absent in normal human cerebrum, cerebellum, heart, lung, spleen, and liver. Scale bar represents 100 μm. (D) Immunoblot analysis of ROR1 in normal tissues using 6D4 mAb. (E) Immunoblot of analysis of ROR1$^{high}$ normal tissues using polyclonal anti-ROR1. (F) Immunoblot validation of ROR1 expression in normal tissues, where tissue lysates have been treated with PNGase F to remove N-linked glycosylation. Deglycosylated ROR1 runs at 100 kDa.
Figure 20B:
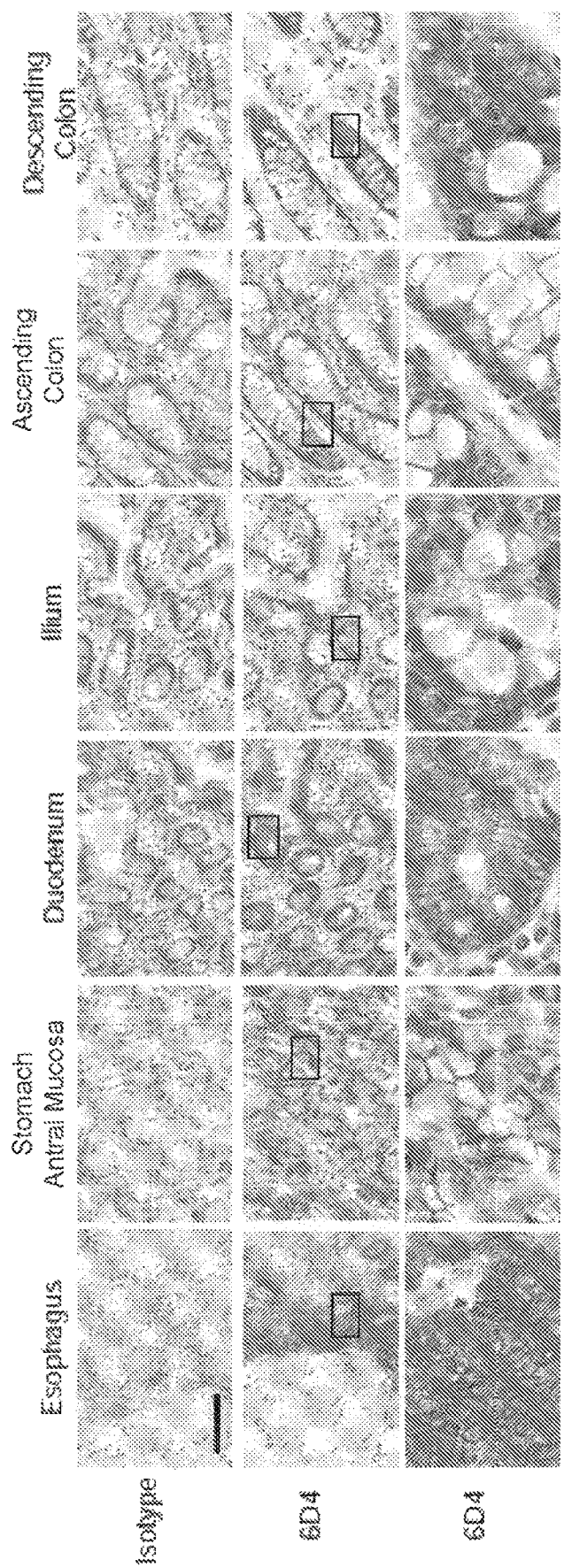
Figure 20C:
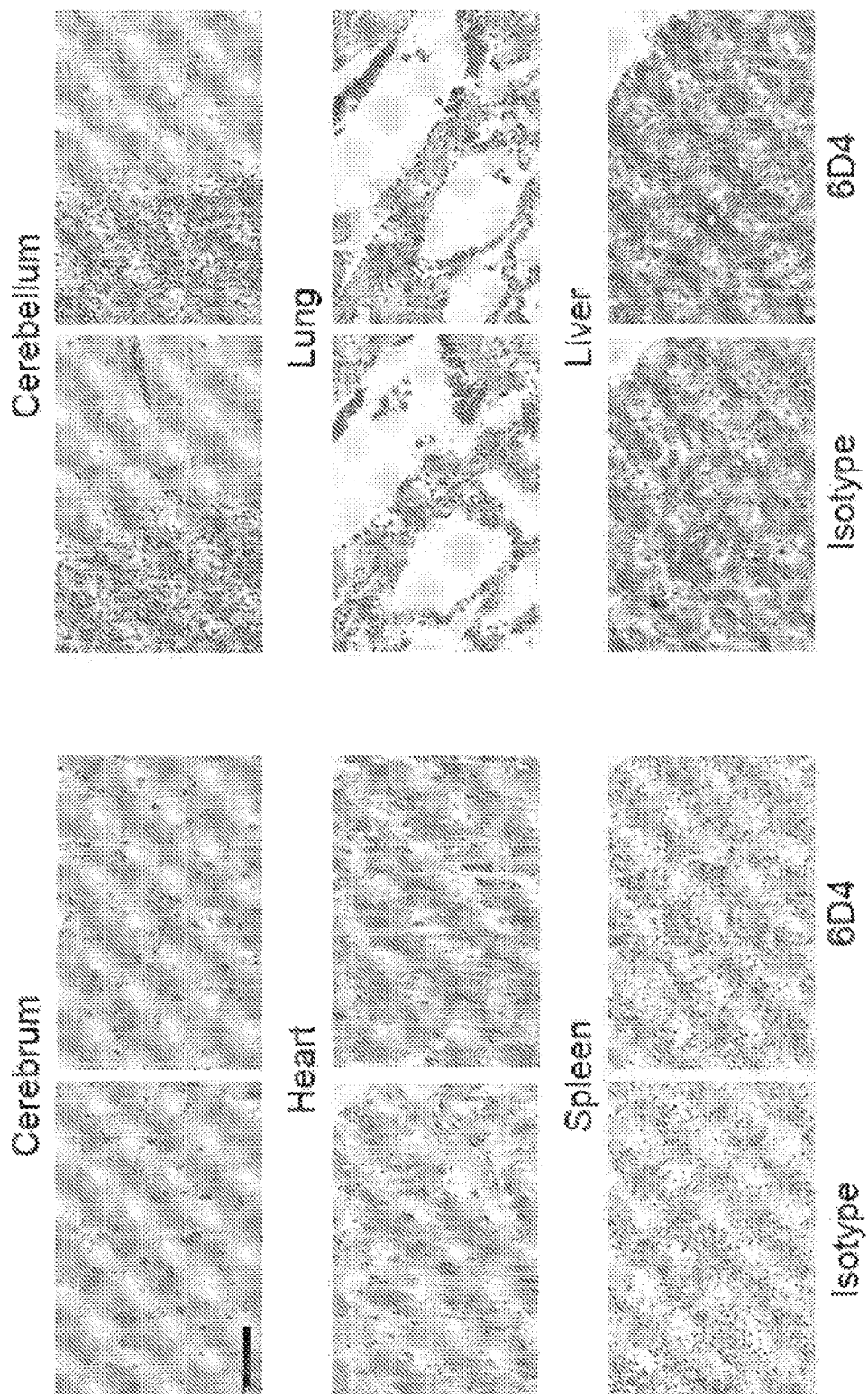

The 6D4 mAb is sensitive and specific for ROR1 and might detect ROR1 on normal tissues that were previously thought to be ROR1 negative when tested with other antibodies. Therefore, ROR1 expression was assessed by IHC using two human multi-organ normal tissue microarray panels. ROR1 was absent in brain, heart, lung, and liver, but significant cell-surface staining was detected in normal parathyroid, pancreatic islet cells, and multiple regions of the gastrointestinal tract (FIGS. 20A-20C). Cell-surface ROR1 was expressed in basal epithelial lining of the esophagus, in the surface and foveolar epithelial cells of the gastric antral mucosa, and in the duodenal mucosa (absorptive cells, goblet cells and crypt epithelium) (FIG. 20B). ROR1 expression on gut mucosa appeared to be higher on luminal epithelium and between cell-cell junctions (FIG. 20B). Cell-surface ROR1 was not seen in the jejunum or ileum and low levels were observed in the surface and crypt epithelium of the ascending and descending colon (FIG. 20B).

Figure 20D:
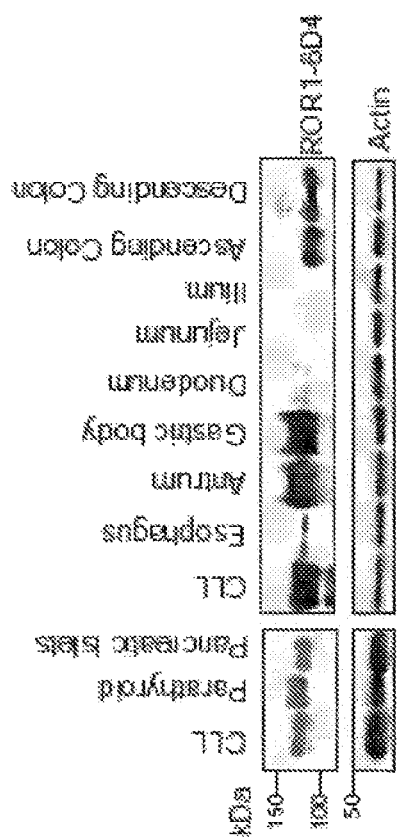
Figure 20E:
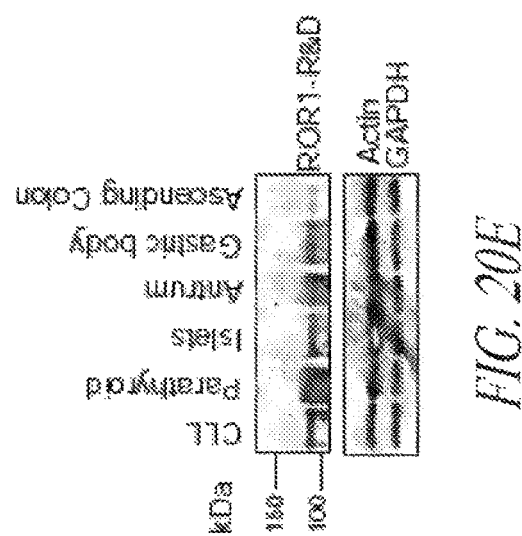
Figure 20F:
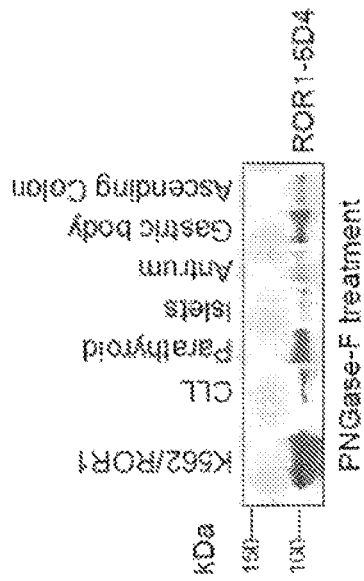
Figure 21:
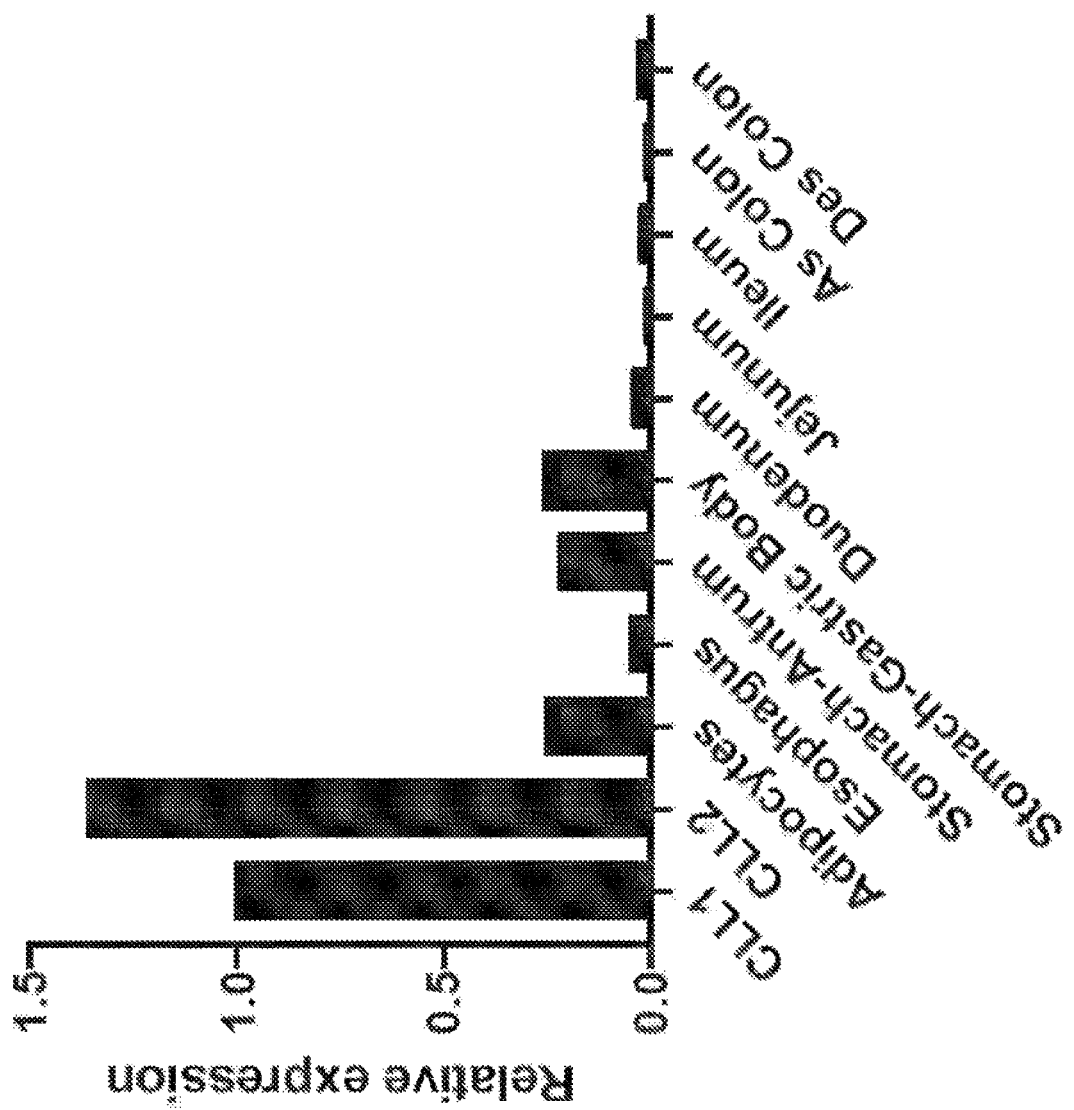
FIG. 21 shows transcript expression of Ror1 (encoding full-length ROR1, ROR1_v1) in CLL PBMC, differentiated adipocytes, and normal human gastrointestinal tissues.

In view of the fact that prior studies had not detected ROR1 in normal tissues by IHC, an immunoblot analysis was conducted to confirm that cell-surface staining observed with 6D4 did not reflect cross reactivity with another protein. Flash frozen samples of the positive tissues were obtained and cell lysates were prepared for immunoblot analysis with 6D4 and the previously published polyclonal goat anti-ROR1 antibody (Dave et al., 2012). Additionally, cDNA was prepared for real time PCR with primers specific for ROR1_v1 (Berger et al., *Cancer Immunology Research* 3:206, 2015). A band consistent with the 130 kDa full-length ROR1 protein was detected by immunoblot in lysates from CLL cells and in lysates from parathyroid, pancreatic islets, stomach antrum and gastric body, esophagus, duodenum, and colon, using both 6D4 and the polyclonal goat anti-ROR1 antibody (FIGS. 20D and 20E). The ROR1 band was slightly higher molecular weight in lysates from tissues such as the parathyroid compared to CLL, possibly due to differences in post translational modifications such as N-linked glycosylation (FIG. 20D). On treating the lysates with PNGaseF, which removes N-linked glycosylation, a deglycosylated ROR1 protein band of 100 kDa was detected in positive tissues as previously reported by Kaucka et al. (*Acta Physiologica* 203:351, 2011) (FIG. 20F). Measuring Ror1_v1 transcripts in human gut tissues by real-time PCR revealed significant Ror1 transcripts in stomach and adipocytes, although transcript levels these tissues were lower than in peripheral blood samples from CLL patients (FIG. 21).

These studies show that antibody 6D4 was sensitive enough to detect cell-surface-expressed, full-length ROR1 in several normal adult tissues. Other than adipocytes (see U.S. Pat. No. 9,163,258), prior reports did not detect ROR1 in parathyroid, pancreatic islets, and regions of the gastrointestinal tract (including the esophagus, stomach, and duodenum).

Rhesus

Despite the above noted findings in human tissue, the safety of ROR1-CAR T cells has been previously demonstrated in a preclinical rhesus macaque (*Macacca mulatta*) model, which was believed to be suitable because the epitope recognized by the ROR1 CAR is conserved, and normal macaque tissues expressed similar levels of Ror1 transcripts (Berger et al., *Cancer Immunology Research* 3:206, 2015). No toxicities were seen in macaques even with infusion of very high doses of functional CAR-T cells (Berger et al., 2015).

Figure 23B:
Figure 23B:
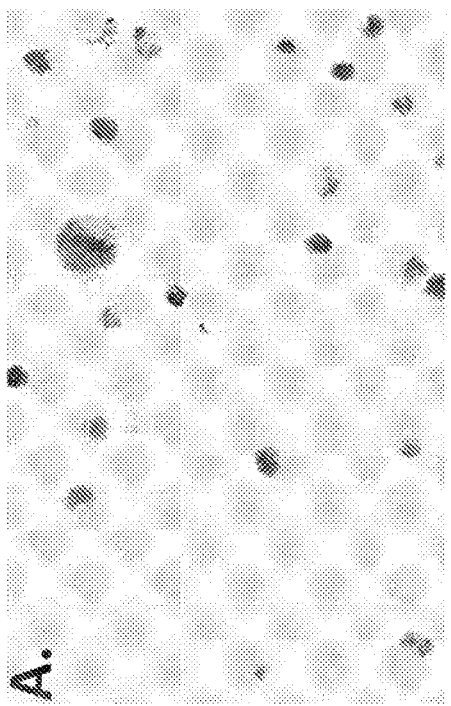
Figure 23B:
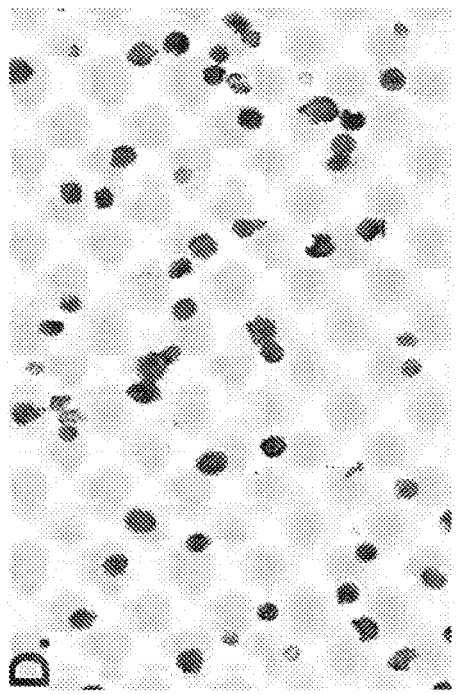
Figure 23B:
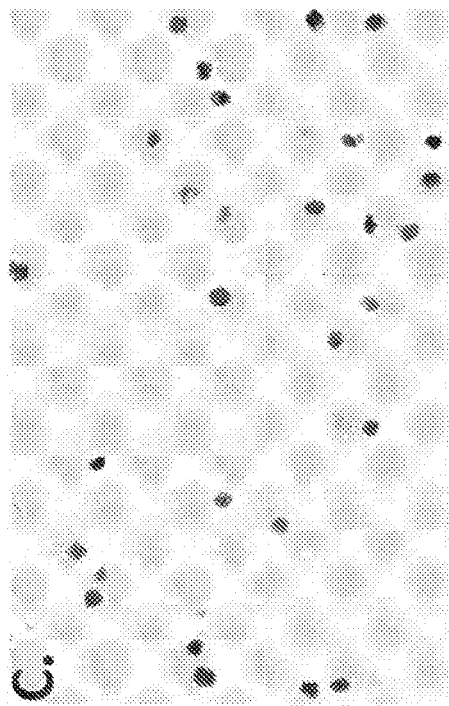
Figure 23C:
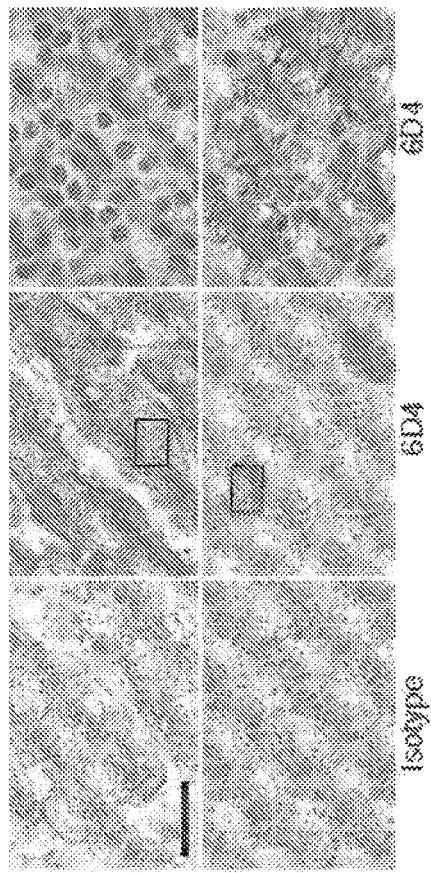
Figure 23D:
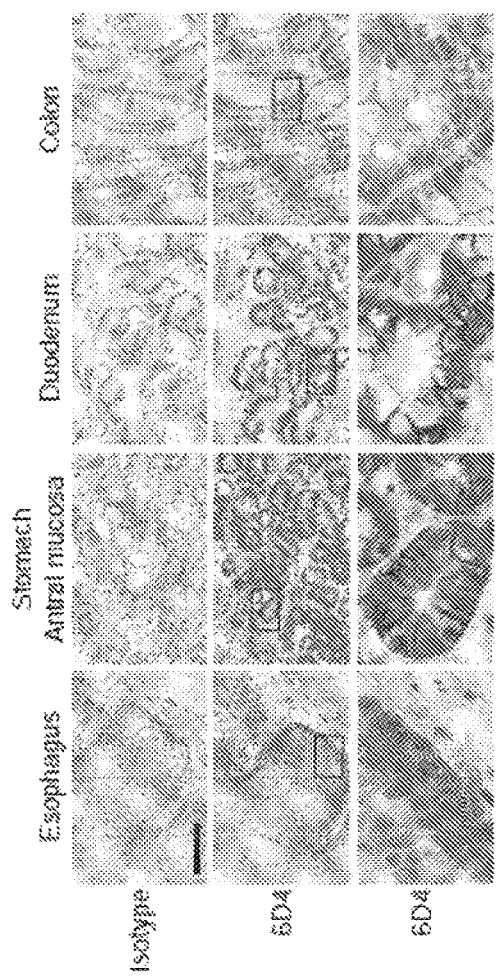

To further evaluate whether ROR1 protein is expressed in the same normal tissues in macaques as in humans, the ability of 6D4 mAb to recognize rhesus ROR1 (e.g., SEQ ID NO.:58) was tested. The rhesus ROR1 epitope corresponding to SEQ ID NO.:59 differs by 1 amino acid from the corresponding sequence in human ROR1 (FIG. 23A). First, K562 and rhesus T cells were transduced with rhesus ROR1 (XP_014996735) as described in Berger et al. (2015), and stained with the 6D4 mAb. The cells transduced to express rhesus ROR1 exhibited brown staining, indicating binding of the 6D4 antibody (FIG. 23B). Additionally, IHC was conducted on a normal rhesus tissue panel and showed cell-surface ROR1 in the same tissues as was observed in human tissues, including parathyroid, pancreatic islets, and gastrointestinal tract including basal esophagus epithelium, foveolar epithelial cells of the stomach antral mucosa, and the intestinal glands of the duodenal mucosa (FIGS. 23C and 23D). However, ROR1 was not detected in the rhesus colon, in contrast to the low levels detected in human colon.

These results indicate the expression pattern of ROR1 is highly similar in rhesus and human tissues. The lack of clinical, biochemical, or histologic evidence of toxicity after infusing ROR1 CAR-T cells in macaques observed in Berger et al. (2015) indicates that trafficking of ROR1-CAR T cells to uninflamed normal tissues may be too low to cause toxicity, or the levels of antigen may be insufficient in those tissues for CAR-T cell recognition in vivo.

Example 7

ROR1-Specific Cars Target Cells Proportional to ROR1 Expression

To determine whether the levels of ROR1 detected by the 6D4 mAb is sufficient for recognition by T cells that express a ROR1-specific CAR, we co-cultured primary human differentiated adipocytes, pancreatic islet cells, and acinar cells with ROR1-CAR T cells and measured cytokines in the culture supernatant. Primary adipocytes were differentiated from human white preadipocytes (Promo Cell) (Hudecek et al., *Blood* 116:4532, 2010). 2000 islet equivalent of primary human islets, acinar cells, and media for islet culture were procured from Prodo labs. Human T cells were transduced with a ROR1 CAR lentivirus to express the ROR1-specific R12scFv CAR, as described in Hudecek et al. (*Clinical Cancer Research* 19:3153, 2013). Primary adipocytes, islets, and acinar cells were co-cultured at a T cell:target ratio of 2:1 with untransduced and ROR1-CAR T cells prepared from two independent donors. Supernatants were harvested after 24 hours of coculture and cytokine production was assayed by multiplex immunoassay (Luminex). Target killing was performed at T cell:target ratio of 5:1 using carboxyfluorescein succinimidyl ester (CFSE) to label target cells and propidium iodide (PI) to score percentage of dead target cells after 24 hours of incubation (see Zaritskaya et al., *Expert Review of Vaccines* 9:601, 2010).

Figure 22A:
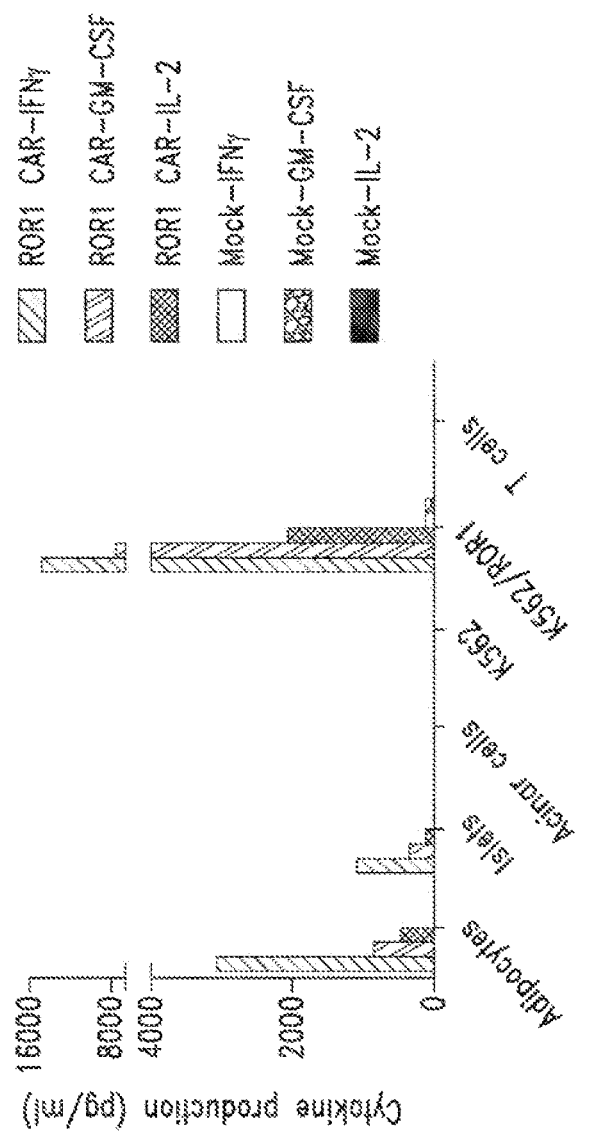
FIGS. 22A through 22D illustrates the relationship between ROR1-CAR T cell activity and ROR1 expression. (A) Cytokine production (IFN-γ, GM-CSF, and IL-2) by ROR1-CAR T cells or mock-transduced T cells after 24 hours of culture with different target cells at a T cell:target ratio of 2:1 (data averaged over 2 independent experiments). (B) ROR1 staining with 6D4 mAb of mature adipocytes in vitro differentiated from preadipocytes. (C) IFN-γ production by ROR1-CAR T cells or mock-transduced T cells from 2 different donors after 24 hours of culture with adipocytes, pancreatic islet cells, or pancreatic acinar cells at a T cell:target ratio of 2:1. (D) ROR1-CAR T cells or mock-transduced T cells were incubated with CFSE labeled targets at a T cell:target ratio of 5:1. Percentage of cells with high levels of propidium iodide (PI$^{high}$) target cells was measured after 24 hours.
Figure 22B:
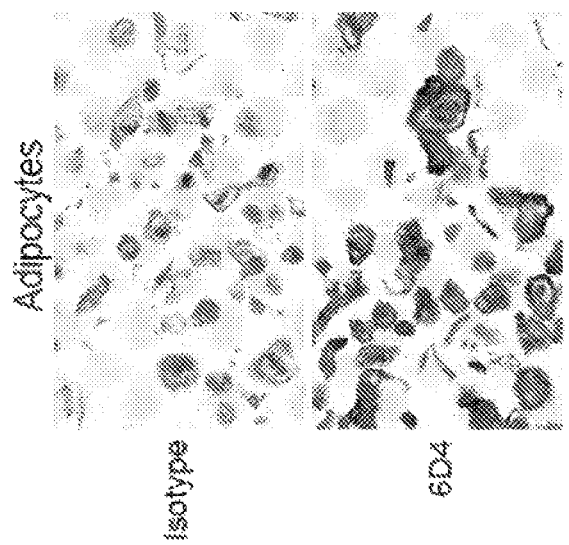
Figure 22C:
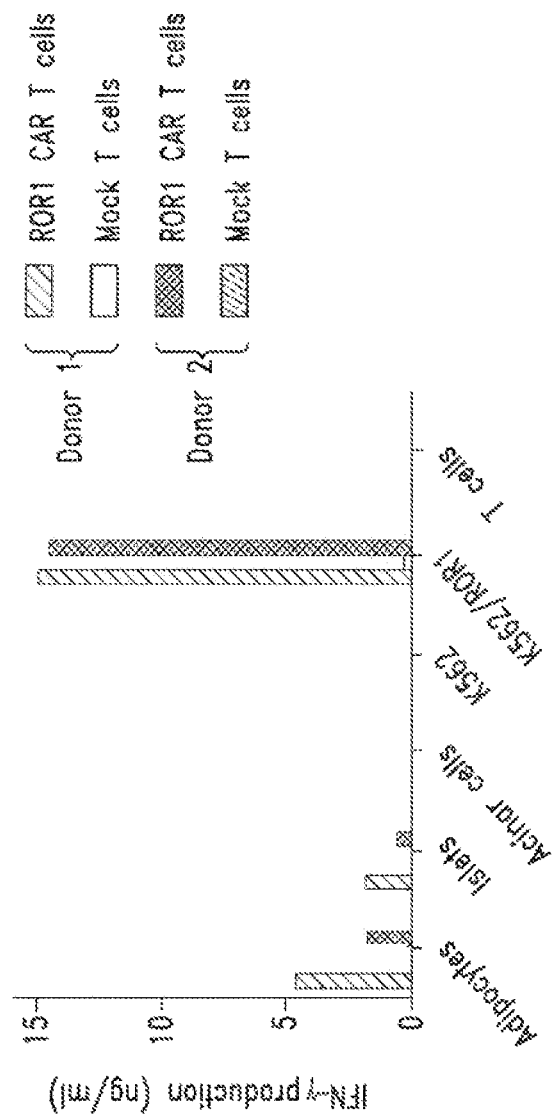
Figure 22D:
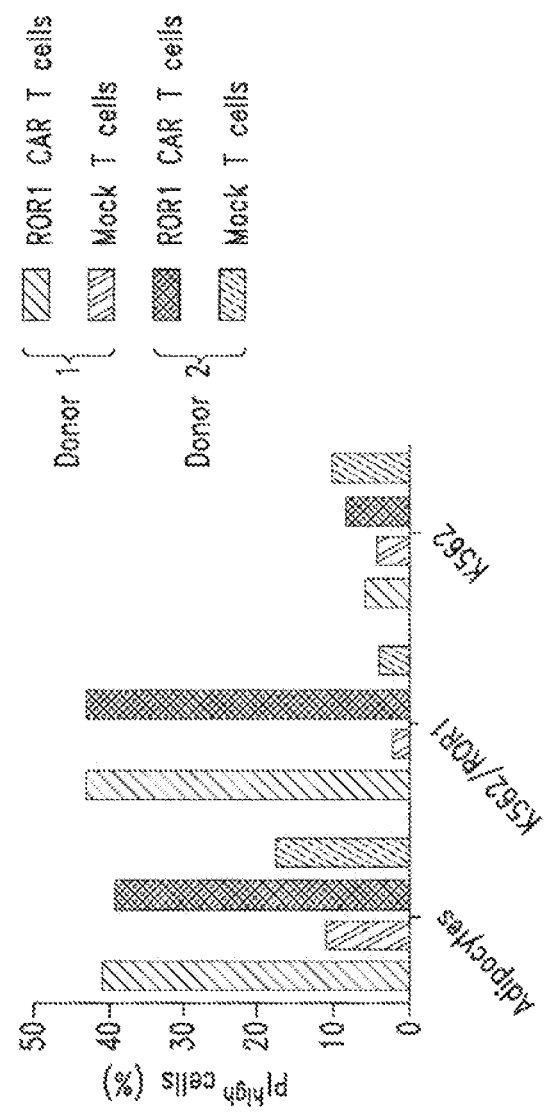

ROR1-CAR T cells, but not mock T cells from the same donors, secreted interferon-γ, GM-CSF, and IL-2 when incubated with primary adipocytes and islet cells (FIGS. 22A-22C). The levels of cytokine secretion during in vitro culture were proportional to ROR1 expression on targets. Additionally, ROR1-CAR T cells lysed ROR1$^+$ K562/ROR1 cells and differentiated adipocytes, but not K562 cells (FIG. 22D).

These findings support the conclusion that the ROR1-CAR T cells target cells proportional to ROR1 expression as indicated by mAb 6D4.

All of the U.S. patents, U.S. patent application publications, U.S. patent applications, foreign patents, foreign patent applications and non-patent publications referred to in this specification, and/or listed in the Application Data Sheet, including U.S. Provisional Patent Application No. 62/290,337 filed Feb. 2, 2016, U.S. Provisional Patent Application 62/324,876 filed Apr. 19, 2016, PCT Application No. PCT/US2017/016300 filed Feb. 2, 2017, and U.S. patent application Ser. No. 16/074,737 filed Aug. 1, 2018, are incorporated herein by reference, in their entirety. The various embodiments described above can be combined to provide further embodiments. Aspects of the embodiments can be modified, if necessary to employ concepts of the various patents, applications and publications to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of detecting a receptor tyrosine kinase-like orphan receptor 1 (ROR1) protein in a biological sample, the method comprising:
   (a) contacting a biological sample with a binding protein, wherein the biological sample is from a human subject and wherein the binding protein comprises an antibody or a binding fragment thereof comprising:
      (1) a heavy chain comprising CDR sequences set forth as SEQ ID NOs.:21, 25, and 29 and a light chain comprising CDR sequences set forth as SEQ ID NOs.:31, 33 and 35;
      (2) a heavy chain comprising CDR sequences set forth as SEQ ID NOs.:22, 26, and 29 and a light chain comprising CDR sequences set forth as SEQ ID NOs.:31, 33, and 35;
      (3) a heavy chain comprising CDR sequences set forth as SEQ ID NOs.:23, 27, and 29 and a light chain comprising CDR sequences as set forth as SEQ ID NOs.:31, 33, and 35; or
      (4) a heavy chain comprising CDR sequences set forth as SEQ ID NOs.:24, 28, and 30 and a light chain comprising CDR sequences set forth as SEQ ID NOs.:32, 34, and 36; and
   (b) detecting the specific binding between the binding protein and the ROR1 protein in the biological sample, or lack thereof, wherein the method detects the presence or absence of the ROR1 protein in the biological sample.

2. The method of claim 1, wherein the method further comprises comparing a level of the specific binding detected in (b) to a reference level, wherein an increased level of binding as compared to the reference level indicates the presence of the ROR1 protein in the biological sample.

3. The method of claim 1, wherein the sample:
   (a) comprises a tissue section and/or a cell;
   (b) comprises a formalin-fixed or frozen tissue section and/or permeabilized cell; and/or
   (c) comprises a formalin-fixed-paraffin-embedded (FFPE) cell or tissue sample or wherein the biological sample is frozen and embedded in Optimal Cutting Temperature compound.

4. The method of claim 3, wherein the sample is derived from a tumor, which tumor is selected from the group consisting of a hematologic malignancy and a solid tumor.

5. The method of claim 3, wherein the sample is derived from a normal tissue.

6. The method of claim 1, wherein:
   the heavy chain comprises SEQ ID NO:37 or a sequence having at least 95% identity to SEQ ID NO:37; and
   the light chain comprises SEQ ID NO:38 or a sequence having at least 95% identity to SEQ ID NO:38.

7. The method of claim 6, wherein the heavy chain comprises SEQ ID NO:37 and the light chain comprises SEQ ID NO:38.

8. The method of claim 1, wherein:
   the heavy chain comprises SEQ ID NO: 12, 13, or 14 or a sequence having at least 95% identity to SEQ ID NO:12, 13 or 14; and
   the light chain comprises SEQ ID NO: 15 or 16 or a sequence having at least 95% identity to SEQ ID NO:15 or 16.

9. The method of claim 1, wherein the binding protein specifically binds to an epitope comprising SEQ ID NO:3.

10. The method claim 1, wherein the ROR1 protein is human ROR1.

11. The method of claim 1, wherein the binding protein is a monoclonal antibody or an antigen binding fragment thereof.

12. The method of claim 1, wherein the detecting in step (b) is by immunohistochemistry.

13. The method of claim 1, wherein the binding protein comprises a marker selected from the group consisting of an enzyme, a dye, a fluorescent label, a DNA barcode, and a tag.

14. The method of claim 13, wherein the marker is a chromogenic reporter enzyme.

15. The method of claim 14, wherein the chromogenic reporter enzyme is horseradish peroxidase (HRP) or alkaline phosphatase (AP).

16. The method of claim 1, wherein the method is carried out with a kit comprising the binding protein.

17. The method of claim 1, wherein the method is carried out with a kit comprising a second binding protein which is a secondary antibody comprising horseradish peroxidase (HRP).

18. The method of claim 1, wherein the binding protein specifically binds to a full-length ROR1 protein.

19. A method for:
(a) identifying the presence of a receptor tyrosine kinase-like orphan receptor 1 (ROR1) protein in a tissue sample, comprising contacting a tissue sample with a binding protein, wherein the binding protein comprises an antibody or a binding fragment thereof comprising:
  (1) a heavy chain comprising CDR sequences set forth as SEQ ID NOs.:21, 25, and 29 and a light chain comprising CDR sequences set forth as SEQ ID NOs.:31, 33, and 35;
  (2) a heavy chain comprising CDR sequences set forth as SEQ ID NOs.:22, 26, and 29 and a light chain comprising CDR sequences set forth as SEQ ID NOs.:31, 33, and 35;
  (3) a heavy chain comprising CDR sequences set forth as SEQ ID NOs.:23, 27, and 29 and a light chain comprising CDR sequences as set forth as SEQ ID NOs.:31, 33, and 35; or
  (4) a heavy chain comprising CDR sequences set forth as SEQ ID NOs.:24, 28, and 30 and a light chain comprising CDR sequences set forth as SEQ ID NOs.:32, 34, and 36; and
(b) detecting specific binding of the binding protein to the tissue, thereby identifying tissue that expresses the ROR1 protein.

20. The method of claim 19, wherein:
the heavy chain comprises SEQ ID NO:37 or a sequence having at least 95% identity to SEQ ID NO:37; and
the light chain comprises SEQ ID NO:38 or a sequence having at least 95% identity to SEQ ID NO:38.

21. The method of claim 20, wherein the heavy chain comprises SEQ ID NO:37 and the light chain comprises SEQ ID NO:38.

22. The method of claim 19, wherein:
the heavy chain comprises SEQ ID NO: 12, 13, or 14 or a sequence having at least 95% identity to SEQ ID NO:12, 13 or 14; and
the light chain comprises SEQ ID NO: 15 or 16 or a sequence having at least 95% identity to SEQ ID NO:15 or 16.

23. The method of claim 19, wherein the binding protein specifically binds to an epitope comprising SEQ ID NO:3.

24. The method claim 19, wherein the ROR1 protein is human ROR1.

25. The method of claim 19, wherein the binding protein is a monoclonal antibody or an antigen binding fragment thereof.

26. The method of claim 19, wherein the detecting in step (b) is by immunohistochemistry.

27. The method of claim 19, wherein the binding protein comprises a marker selected from the group consisting of an enzyme, a dye, a fluorescent label, a DNA barcode, and a tag.

28. The method of claim 27, wherein the marker is a chromogenic reporter enzyme.

29. The method of claim 28, wherein the chromogenic reporter enzyme is horseradish peroxidase (HRP) or alkaline phosphatase (AP).

30. The method of claim 19, wherein the method is carried out with a kit comprising the binding protein.

31. The method of claim 19, wherein the method is carried out with a kit comprising a second binding protein which is a secondary antibody comprising horseradish peroxidase (HRP).

32. The method of claim 19, wherein the detection method further comprises comparing a level of the specific binding detected in (b) to a reference level, wherein an increased level of binding as compared to the reference level indicates the presence of the ROR1 protein in the sample.

33. The method of claim 19, wherein the binding protein specifically binds to a full-length ROR1.

* * * * *

UNITED STATES PATENT AND TRADEMARK OFFICE
CERTIFICATE OF CORRECTION

PATENT NO. : 11,932,691 B2
APPLICATION NO. : 17/157810
DATED : March 19, 2024
INVENTOR(S) : Ashwini Balakrishnan et al.

It is certified that error appears in the above-identified patent and that said Letters Patent is hereby corrected as shown below:

In the Claims

Column 87, Claim 3, Line 60:
"The method of claim 1, wherein the sample:"
Should read:
--The method of claim 1, wherein the biological sample:--

Column 88, Claim 4, Line 24:
"The method of claim 3, wherein the sample is derived"
Should read:
--The method of claim 3, wherein the biological sample is derived--

Column 88, Claim 5, Line 27:
"The method of claim 3, wherein the sample is derived"
Should read:
--The method of claim 3, wherein the biological sample is derived--

Column 88, Claim 10, Line 46:
"The method claim 1,"
Should read:
--The method of claim 1,--

Column 89, Claim 19, Line 27:
"tissue, thereby identifying"
Should read:
--tissue sample, thereby identifying--

Column 90, Claim 32, Line 34:
"the presence of the RORI protein in the sample."

Signed and Sealed this
Twenty-sixth Day of November, 2024

Katherine Kelly Vidal
*Director of the United States Patent and Trademark Office*

Should read:
--the presence of the RORI protein in the tissue sample.--